US011253510B2

(12) United States Patent
Puyo et al.

(10) Patent No.: US 11,253,510 B2
(45) Date of Patent: Feb. 22, 2022

(54) ANTI-NEUTROPHIL ACTIVITY ON INNATE IMMUNE RESPONSE

(71) Applicant: Washington University, St. Louis, MO (US)

(72) Inventors: Carlos A. Puyo, St. Louis, MO (US); Andrew Gelman, St. Louis, MO (US)

(73) Assignee: Washington University, St. Louis, MO (US)

( * ) Notice: Subject to any disclaimer, the term of this patent is extended or adjusted under 35 U.S.C. 154(b) by 76 days.

(21) Appl. No.: 16/072,074

(22) PCT Filed: Jan. 23, 2017

(86) PCT No.: PCT/US2017/014612
§ 371 (c)(1),
(2) Date: Jul. 23, 2018

(87) PCT Pub. No.: WO2017/127830
PCT Pub. Date: Jul. 27, 2017

(65) Prior Publication Data
US 2019/0038616 A1 Feb. 7, 2019

Related U.S. Application Data

(60) Provisional application No. 62/281,936, filed on Jan. 22, 2016.

(51) Int. Cl.
*A61K 31/4706* (2006.01)
*A61K 38/46* (2006.01)
*A61K 31/198* (2006.01)
*A61L 31/10* (2006.01)
*A61L 17/14* (2006.01)
*A61L 27/54* (2006.01)
*A61L 17/00* (2006.01)
*A61L 27/34* (2006.01)
*A61L 29/16* (2006.01)
*A61L 29/08* (2006.01)
*A61L 31/16* (2006.01)
*A61P 31/00* (2006.01)
*A61P 29/00* (2006.01)
*A61M 25/00* (2006.01)

(52) U.S. Cl.
CPC ........ *A61K 31/4706* (2013.01); *A61K 31/198* (2013.01); *A61K 38/465* (2013.01); *A61L 17/005* (2013.01); *A61L 17/145* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *A61M 25/0045* (2013.01); *A61P 29/00* (2018.01); *A61P 31/00* (2018.01); *C12Y 301/21001* (2013.01); *A61K 2300/00* (2013.01); *A61M 2205/0238* (2013.01)

(58) Field of Classification Search
None
See application file for complete search history.

(56) References Cited

U.S. PATENT DOCUMENTS

| | | | |
|---|---|---|---|
| 6,475,434 B1 * | 11/2002 | Darouiche | A61L 2/0082 422/28 |
| 6,620,853 B1 * | 9/2003 | Shift | A61K 31/606 514/708 |
| 8,617,542 B2 | 12/2013 | Madhyastha et al. | |
| 9,415,046 B2 * | 8/2016 | Mehal | A61K 31/612 |
| 2003/0177819 A1 * | 9/2003 | Maale | A61L 2/28 73/105 |
| 2005/0208470 A1 * | 9/2005 | Latz | A61K 49/0008 435/4 |
| 2005/0281813 A1 * | 12/2005 | Dedera | A61K 38/177 424/143.1 |
| 2007/0182055 A1 | 8/2007 | Eells et al. | |
| 2009/0304769 A1 * | 12/2009 | Kunkel | A61K 31/13 424/423 |
| 2012/0263736 A1 | 10/2012 | Hauser | |
| 2014/0356334 A1 | 12/2014 | McCord | |
| 2015/0164830 A1 | 6/2015 | Goldstein | |

FOREIGN PATENT DOCUMENTS

WO 2011041311 A2 4/2011

OTHER PUBLICATIONS

Tobudic et al. Mycoses (2012) 55: 199-204 (Year: 2012).*
Venkatesh et al. J. Med. Microbiol. (2009) 58: 936-944 (Year: 2009).*
Shinde et al. J. Gen. Appl. Microbiol. (2013) 59: 167-170 (Year: 2013).*
El-Rehewy et al. Clinical Med: Urology (2009) 3: 1-8 (Year: 2009).*
Yang et al. Acta Oto-Lanygolocica (2009) 129:10: 1036-1042 (Year: 2009).*
Abolyosr et al., Effect of Oral Ciprofloxacin And N-Acetylcysteine On Biofilm Formation On Indwelling Ureteral Stents; 1-page, J. Urology (2009) 181(4, Supplement): 453.
Pugach et al., Antibiotic Hydrogel Coated Foley Catheters For Prevention of Urinary Tract Infection In a Rabbit Model; The Journal of Urology; 1999, vol. 162, pp. 883-887.

(Continued)

Primary Examiner — Susan M Hanley
(74) Attorney, Agent, or Firm — Stinson LLP

(57) ABSTRACT

Disclosed are compositions, medical devices and methods for ameliorating sterile injury due object use in a subject in need thereof. More particularly, the present disclosure relates to compositions including N-Acetylcysteine and an aminoquinoline. The present disclosure also relates to compositions including an endonuclease and an aminoquinoline. The present disclosure also relates to medical devices including a coating comprising N-Acetylcysteine, an aminoquinoline, an endonuclease, and combinations thereof.

9 Claims, 41 Drawing Sheets

(56) References Cited

OTHER PUBLICATIONS

Saivisveswar et al., Efficacy of Chloroquine against *Escherichia coli* and Proteus vulgaris: An in vitro Study; Scholars Journal of Applied Medical Sciences (SJAMS); 6-pages.
Chen et al., Sterile inflammation: sensing and reacting to damage; Nat Rev Immunol., 2010, vol. 10, No. 12, pp. 826-837.
Jhunijunwala et al., Neutrophil Responses to Sterile Implant Materials; PLOA/one; 2010; pp. 1-16.
Menezes et al., Sensing sterile injury: Opportunities for pharmacological control; Pharmacology & Therapeutics; 2011, vol. 132, pp. 204-214.
SHEN et al., Processes of Sterile Inflammation; J Immunol., 2013, vol. 191, No. 6, pp. 1-15.
Talati et al., Role of baqcterial DNA in macrophage activation by group B streptococci; Microbes and Infection, 2008, vol. 10, pp. 1106-1113.

\* cited by examiner

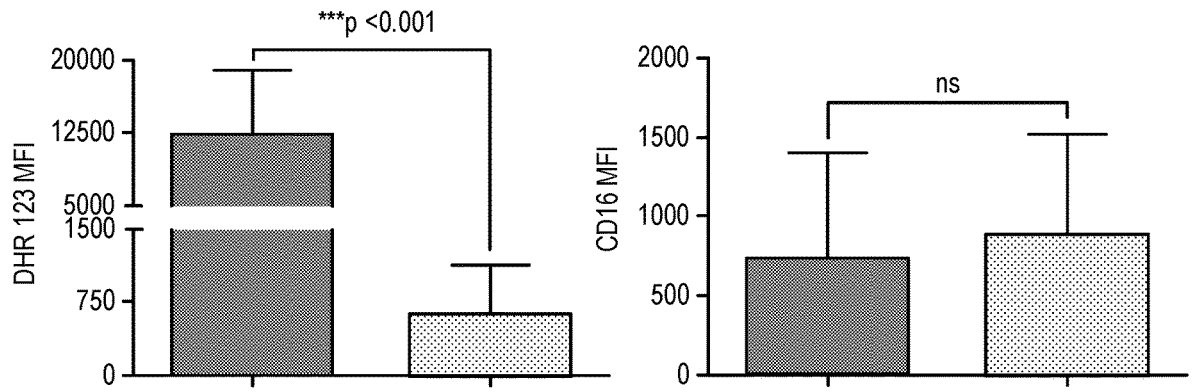
FIG. 10A
FIG. 10B
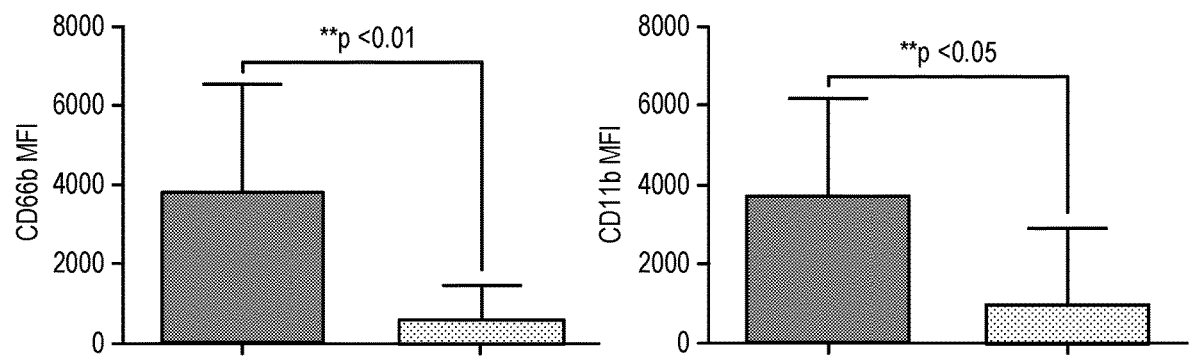
FIG. 10C
FIG. 10D
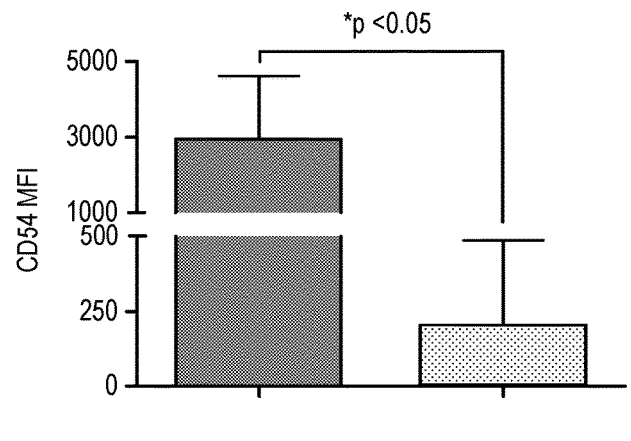
FIG. 10E

■ Sore Throat TLF  ▨ No Sore Throat TLF

■ Sore Throat TLF  ▨ No Sore Throat TLF 21A  21B 21C  21D 21E  21F

■ Untreated    ▨ Treated

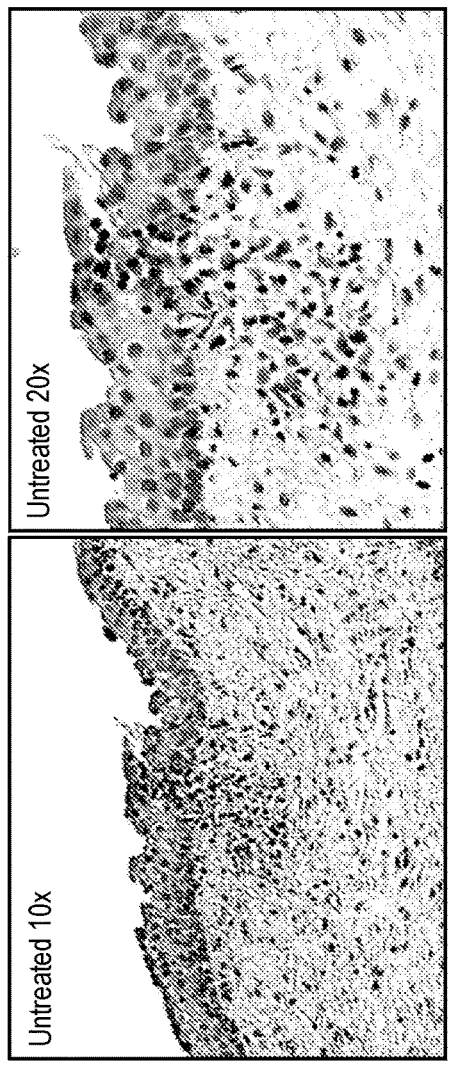
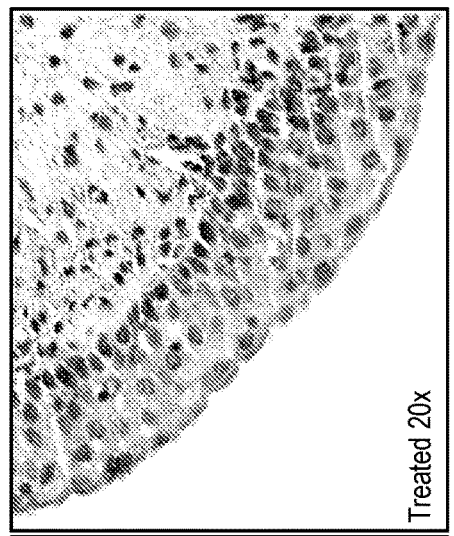
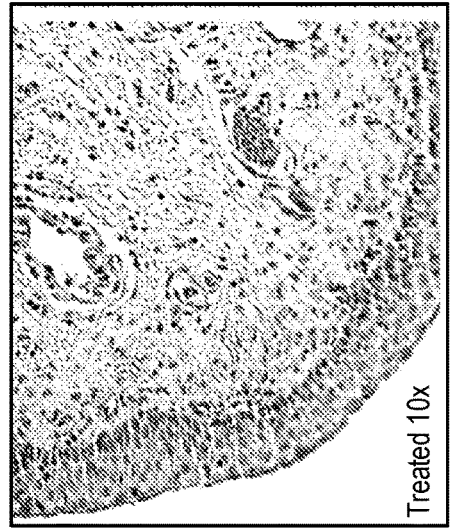
FIG. 30A  FIG. 30B  FIG. 30C  FIG. 30D

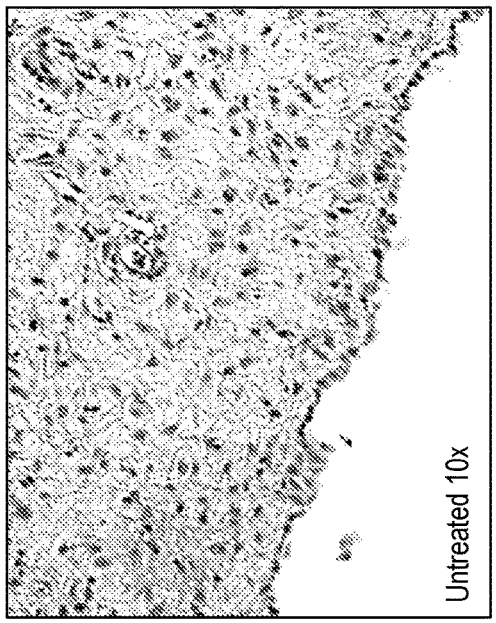
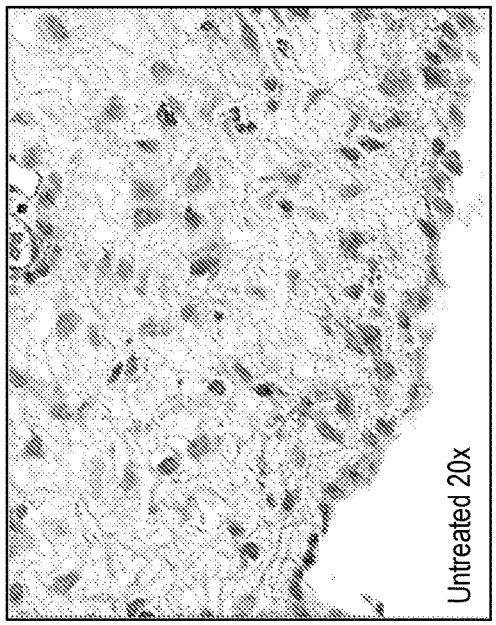
FIG. 32A  FIG. 32B
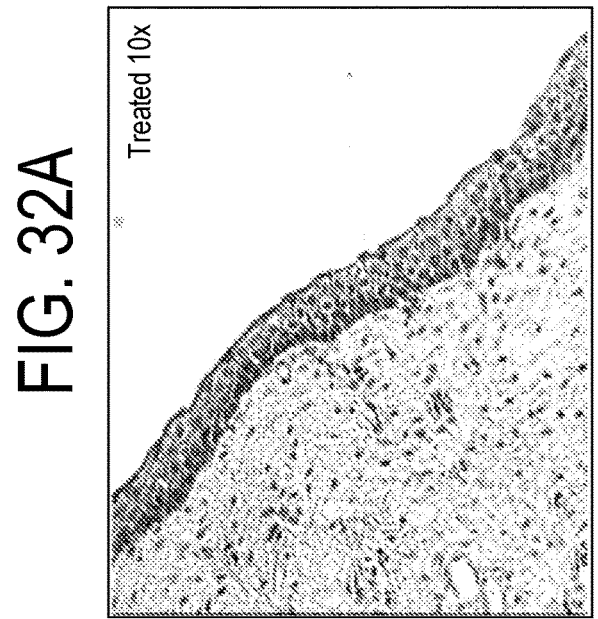
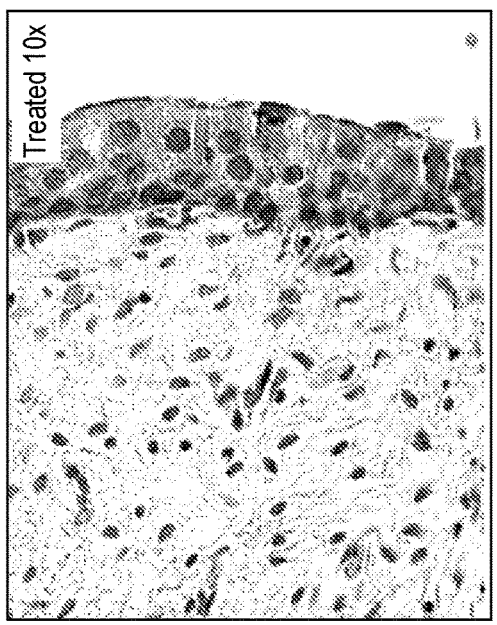
FIG. 32C  FIG. 32D

ANTI-NEUTROPHIL ACTIVITY ON INNATE IMMUNE RESPONSE

CROSS REFERENCE TO RELATED APPLICATIONS

This application claims priority to International Publication Number WO 2017/127830, filed on Jan. 23, 2017, which claims priority to U.S. Provisional Patent Application Ser. No. 62/281,936, filed on Jan. 22, 2016, the disclosures of which are hereby expressly incorporated by reference in their entireties.

BACKGROUND OF THE DISCLOSURE

The present disclosure relates generally to compositions and methods for ameliorating injury due to foreign object use. More particularly, the present disclosure is directed to a composition comprising: N-Acetylcysteine and an aminoquinoline. The present disclosure further relates to methods for treating sterile injury due to foreign object use in a subject in need thereof by administering compositions including N-Acetylcysteine and an aminoquinoline. The present disclosure also relates to compositions including an endonuclease and an aminoquinoline. The present disclosure further relates to methods for treating sterile injury due to foreign object use in a subject in need thereof by administering compositions including an endonuclease and an aminoquinoline. The present disclosure further relates to medical devices coated with a composition comprising: N-Acetylcysteine, an aminoquinoline, an endonuclease, and combinations thereof. The present disclosure further relates to methods for diagnosing sterile injury due to foreign object use in a subject in need thereof.

Placement of foreign objects such as endotracheal tubes (ETT) and catheters as part of standard medical care is commonly performed, but can result in a local or systemic inflammatory response. Endotracheal tube (ETT) placement is commonly associated with postoperative sore throat (POST) pain. Incidence of POST has been reported between 20-50% following ETT placement, and is linked with symptoms of upper airway discomfort like tracheitis, hoarseness, and dysphagia, which may delay patient recovery after surgery. Several factors are implicated in POST including ETT materials, cuff pressure, airway instrumentation, and pharmacological agents. ETT placement is also associated with the development of pneumonia in infectious and non-infectious settings. However, in the absence of infection the underlying mechanisms that contribute to POST remain unclear. Local mechanical trauma results in cellular injury that is responsible for release of innate immune activators such as mitochondrial DNA. Tracheal injury following endotracheal intubation results in neutrophil activation and sore throat. Excessive reactive oxygen species (ROS) activity promotes tissue damage and cytokine activity.

Short-term ETT placement results in mechanically mediated tissue injury and induces the influx of neutrophils. Studies have demonstrated the link between neutrophil activation and neuropathic pain. For example, animal studies have highlighted the importance of neutrophil elastase release in the induction of acute pain. Neutrophils also release other pro-algesic mediators, including reactive oxygen species (ROS), IL-1$\beta$, and TNF-$\alpha$.

Local mechanical trauma results in cellular injury that is responsible for release of innate immune activators and inflammation. Tracheal associated inflammation resulting from endotracheal tube use can cause inflammation, subglottic stenosis (narrowing or occlusion of the airway) and has a 10-20% mortality and 20-50% morbidity. Catheter associated use can cause inflammatory damage of the urinary tract and lead to urinary tract infections. Catheter-associated urinary tract infection (CAUTI) is the most common hospital-acquired infection, occurring in up to 25% of patients requiring catheterization for longer than 7 days. Ischemia reperfusion injury causes inflammation that can result in interference with the blood supply causing tissue damage, ulcers, organ transplantation failure, stroke, and cardiac arrest. Implanted glucose monitoring systems often malfunction as a result of multiple factors, including inflammation at the site of implantation and bio-fouling. Use of stents in angioplasty can result in restenosis.

Approximately 100 million Foley catheters are sold annually worldwide with 25% of sales occurring in the United States. 25% of patients admitted to hospitals will have an indwelling catheter and 7% of nursing home residents are managed by long-term catheterization. Foley catheter associated bladder injury is associated with pain, spasms urinary urgency and progression to urinary tract infection (CAUTI). CAUTI is the most common hospital acquired infection (40%) in hospitals and nursing homes. There is a 7% daily risk of acquiring CAUTI and over 1 million cases are reported annually. The cost to treat a simple CAUTI has been estimated at $675 per case whereas the cost of treating bacteremia (blood infection) is $3,800 per patient. The total healthcare burden is estimated at $830 million dollars per year. Currently available antibiotic and silver coated catheters are marketed for approximately $10 above the non-antimicrobial equivalent. Despite efforts to provide pain, inflammation and infection relief for patients with Foley catheters, there is currently no universally accepted therapy.

Evolution of the immune system has enabled the human body to recognize self and non-self protein-based patterns known as pathogen associated molecular patterns (PAMP), used to discriminate between bacterial and non-bacterial molecules. One molecular pattern that originates from aseptic material (mtDNA) released during local cellular injury may result in neutrophil cell activation mediated by TLR-9 expression.

TLR-9 is a transmembrane protein preserved throughout evolution from insects to mammals and has characteristic leucine-rich repeats (LRR) located extracellularly and an intracellular domain known as Toll/Interleukin-1 Receptor (TIR). Neutrophil activation mediated by TLR-9 involves several steps such as endocytosis of unmethylated bacterial CpG-DNA, acidification of the endosome, and recognition of CpG motifs at the endolysosomes, resulting in NF-$\kappa\beta$ activation. NF-$\kappa\beta$ regulates pro-inflammatory and anti-inflammatory cytokine production.

Neutrophil cells are the first cells to arrive at a site of tissue injury as mediators of the innate immune response. Although initial neutrophil activity is intended to defend and prevent further tissue damage, uncontrolled activity can inflict tissue damage (scar, tissue overgrowth) and infection. Under normal conditions neutrophil cells will die following an apoptotic pathway with minimal immunological consequence. However, neutrophil injury mediated by mitochondria DNA may lead to persistent inflammation and delayed apoptosis resulting in further tissue damage as a result of Toll-Like Receptor 9 (TLR-9) expression. Neutrophils can be activated by damage associated molecular patterns (DAMPs) released by cells injured during stress such as crush trauma. DAMPs are recognized by pattern recognition receptors (PRRs), which trigger inflammatory signaling pathways inducing gene expression. Neutrophils express all major classes of PRRs including toll-like (TLR), scavenger and complement receptors. In particular, TLR-9 recognizes hypomethylated CpG DNA motifs within the bacterial genome. Consistent with the bacterial ancestry of mitochondria, recent work has demonstrated TLR-9-dependent neutrophil activation in response to mitochondrial DNA (mtDNA) released by injured cells.

Strategies aimed at preventing tracheal injury secondary to the ETT have included antibiotics, steroids, non-steroidal anti-inflammatories, local anesthetics, water-base lubricants, and many other interventions that have not shown consistent benefit.

Accordingly, there exists a need for compositions and methods for ameliorating injury and pain due to foreign object placement such as tracheal injury (sore throat, tracheomalasia) and catheter injury.

BRIEF DESCRIPTION OF THE DISCLOSURE

The present disclosure relates generally to compositions and methods for ameliorating injury due to foreign object use. More particularly, the present disclosure is directed to a composition comprising: N-Acetylcysteine and an aminoquinoline. The present disclosure further relates to methods for treating sterile injury due to foreign object use in a subject in need thereof by administering compositions including N-Acetylcysteine and an aminoquinoline. The present disclosure also relates to compositions including an endonuclease and an aminoquinoline. The present disclosure further relates to methods for treating sterile injury due to foreign object use in a subject in need thereof by administering compositions including an endonuclease and an aminoquinoline. The present disclosure further relates to medical devices coated with a composition comprising: N-Acetylcysteine, an aminoquinoline, an endonuclease, and combinations thereof. The present disclosure further relates to methods for diagnosing sterile injury due to foreign object use in a subject in need thereof.

In one aspect, the present disclosure is directed to a composition comprising: N-Acetylcysteine and an aminoquinoline.

In one aspect, the present disclosure is directed to a method for ameliorating sterile injury due to foreign object use in a subject in need thereof, the method comprising: administering a composition comprising N-Acetylcysteine and an aminoquinoline.

In one aspect, the present disclosure is directed to a composition comprising: an endonuclease and an aminoquinoline.

In one aspect, the present disclosure is directed to a method for ameliorating sterile injury due to foreign object use in a subject in need thereof, the method comprising: administering a composition comprising: an endonuclease and an aminoquinoline.

In one aspect, the present disclosure is directed to a method for diagnosing sterile injury due to foreign object use in a subject in need thereof. The method includes: determining mtDNA in a sample from the subject.

In one aspect, the present disclosure is directed to a method for reducing neutrophil-mediated inflammation in a subject in need thereof. The method includes administering to the subject a composition comprising: N-Acetylcysteine and an aminoquinoline.

In one aspect, the present disclosure is directed to a method for reducing neutrophil-mediated inflammation in a subject in need thereof. The method includes administering to the subject a composition comprising: an endonuclease and an aminoquinoline.

In one aspect, the present disclosure is directed to a medical device coated with a composition comprising N-Acetylcysteine, an aminoquinoline, an endonuclease, and combinations thereof.

BRIEF DESCRIPTION OF THE DRAWINGS

The disclosure will be better understood, and features, aspects and advantages other than those set forth above will become apparent when consideration is given to the following detailed description thereof, Such detailed description makes reference to the following drawings, wherein:

FIGS. 10A-10E are graphs depicting a distinct activation phenotype in Sore throat TLF neutrophils. TLF neutrophils were identified by FACS analysis on a SCC$^{hi}$ CD66b$^{lo-hi}$ CD16$^{lo-hi}$ gate and evaluated for (FIG. 10A) ROS production with DHR-123 dye and plasma membrane expression of CD16b (FIG. 10B), CD66b (FIG. 10C), CD11b (FIG. 10D), and CD54 (FIG. 10E) using appropriate antibodies. Data (left panel) is a representative overlaid histogram result from a sore throat and a non-sore throat patient where solid lines represent indicated antibodies and dotted lines show respective isotype antibody controls. Mean results (right panel) are shown as the mean fluorescence intensity (MFI)±SD derived from sore patients (N=13) and non-sore throat (N=18) patients.

FIG. 11A depicts mitochondrial DNA (mtDNA) TLF and serum concentrations determined by real time quantitative polymerase chain reaction (qPCR) analysis using cytochrome b primers and a cytochrome b standard prepared from human lung mitochondria. FIG. 11B depicts bacterial 16S rRNA DNA levels measured by qPCR where the quantitation cycle number (Cq) represents DNA levels. FIG. 11C depicts representative TLF neutrophil TLR-9 levels shown as an overlaid histogram from a sore throat and a non-sore throat patient where solid lines represent TLR-9 staining and dotted lines represent isotype control staining. Data for FIGS. 11A & 11B is a representative result of at least three independent experiments. Results in (FIGS. 11A, & 11C) are shown as indicated mean values±SD for sore patients (N=13) and non-sore throat (N=18) patients.

FIGS. 30A-30D are microscopic images of the urethra at point of contact with untreated Foley catheters (FIGS. 30A & 30B) and treated Foley catheters (FIGS. 30C & 30D). FIGS. 30A & 30C at 10× magnification; FIGS. 30B & 30D at 20× magnification.

FIGS. 31A & 31C at 10× magnification; FIGS. 31B & 31D at 20× magnification.

FIGS. 32A-32D are of the upper half of the bladder in animals with untreated Foley catheters (FIGS. 32A & 32B) and treated Foley catheters (FIGS. 32C & 32D). FIGS. 32A & 32C at 10× magnification; FIGS. 32B & 32D at 20× magnification.

Figure 1:
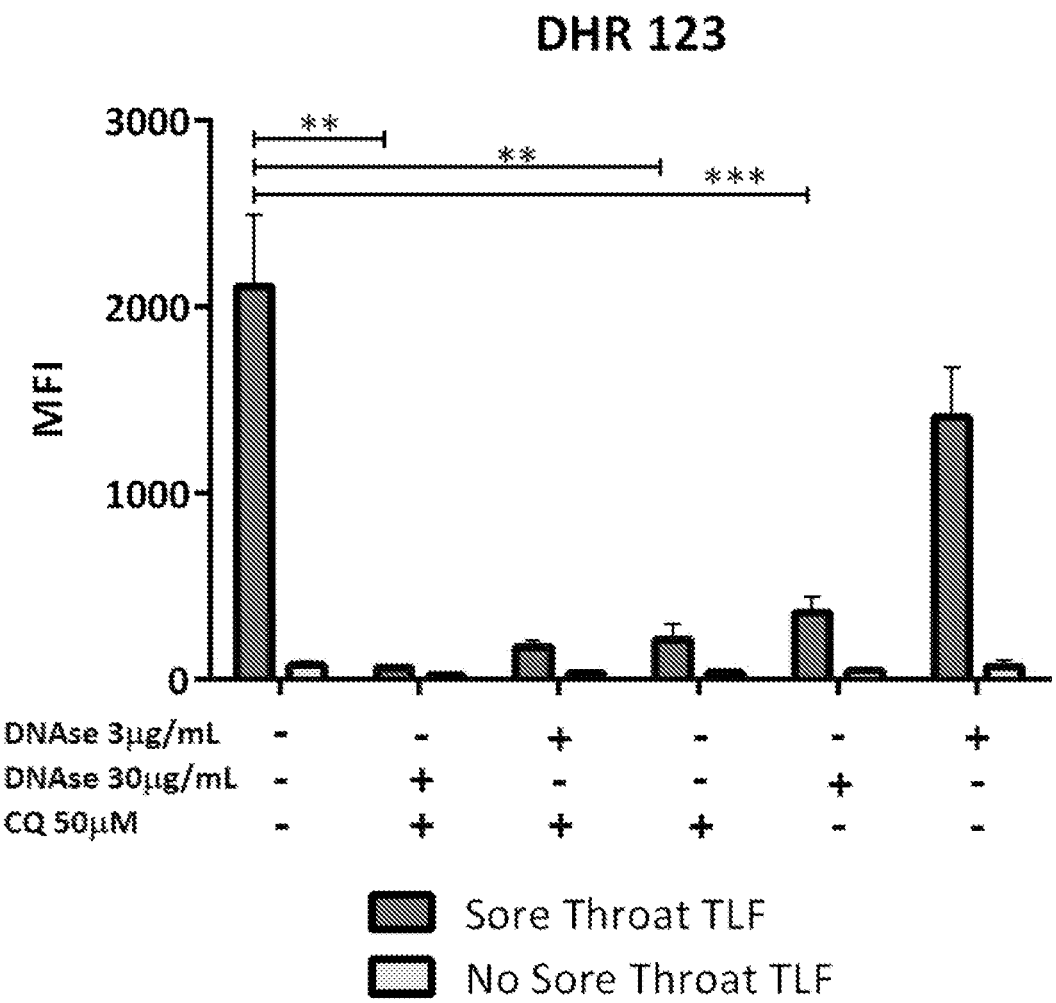
FIG. 1 is a graph depicting assessment of Dihydroxyrhodamine 123 (DHR-123) in subjects administered DNase I and chloroquine (CQ) as discussed in Example 2.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the scope of the disclosure as defined by the appended claims

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As disclosed herein, contact between human mucosal surfaces (e.g., trachea, bladder, rectum, ear drum, membranes, and eyes) with a foreign body (e.g., medical devices) results in inflammation and pain. If not treated, this inflammation can progress to tissue necrosis and infection. The compositions and methods disclosed herein can be used to treat mucosal injury, and thus, prevent pain and infections at an early stage of development.

As used herein, sterile injury refers to inflammation, necrosis and pain resulting from trauma and chemically induced injury that can occur in the absence of any microorganism in subjects where foreign objects such as medical devices are used.

As used herein, "a subject in need thereof" (also used interchangeably herein with "a patient in need thereof") refers to a subject susceptible to or at risk of a specified disease, disorder, or condition. The methods disclosed herein can be used with a subset of subjects who are susceptible to or at elevated risk of sterile injury due to foreign object use. The methods of reducing neutrophil extracellular traps (NET) formation during bacterial biofilm infection can be used with a subset of subjects who are susceptible to or at elevated risk of sterile injury due to foreign object use. The methods of reducing biofilm formation on a device can be used with a subset of subjects who are subjected to procedures using devices wherein the devices contact and/or come in close contact to mucosal tissues. The methods of promoting neutrophil phagocytosis of bacteria in response to mtDNA can be used with a subset of subjects who are susceptible to or at elevated risk of sterile injury due to foreign object use. The methods of reducing reactive oxygen species (ROS) production by a neutrophil can be used with a subset of subjects who are susceptible to or at elevated risk of sterile injury due to foreign object use. The methods of reducing pro-inflammatory protein production by a neutrophil can be used with a subset of subjects who are susceptible to or at elevated risk of sterile injury due to foreign object use.

Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

As used herein, "a subject" (also interchangeably referred to as "an individual" and "a patient") refers to animals including humans and non-human animals. Accordingly, the compositions, devices and methods disclosed herein can be used for human and veterinarian applications, particularly human and veterinarian medical applications.

The compositions of the present disclosure can be administered to animals, preferably to mammals, and in particular to humans as therapeutics per se, as mixtures with one another or in the form of pharmaceutical preparations, and which as active constituent contains an effective dose of the compositions, in addition to customary pharmaceutically innocuous excipients and additives. The active agents described herein can also be administered in form of salts, which are obtainable by reacting the respective active agents with physiologically acceptable acids and bases. It is preferred to introduce the active ingredients, optionally in the form of a physiologically acceptable salt, in a pharmaceutical composition together with one or more adjuvants, excipients, carriers, buffers, diluents, and/or other customary pharmaceutical auxiliaries. Pharmaceutically acceptable carriers, and, optionally, other therapeutic and/or prophylactic ingredients must be "acceptable" in the sense of being compatible with the other ingredients of the formulation and not harmful to the recipient thereof.

A medicament of the present disclosure can be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compositions of the present disclosure, which matrices can be in form of shaped articles, e.g. films or microcapsules.

The compositions of the present disclosure together with a conventional adjuvant, carrier, or diluent, can thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms can contain any suitable effective amount of the active ingredient commensurate with the intended daily dosage range to be employed. Pharmaceutically acceptable carriers can be either solid or liquid. Solid form preparations include powders, tablets, pills, capsules, cachets, lozenges, suppositories, and dispersible granules. A solid carrier can be one or more substances which may also act as diluents, flavoring agents, solubilizers, lubricants, suspending agents, binders, preservatives, tablet disintegrating agents, or an encapsulating material. Formulations for parenteral administration (e.g. by injection, for example bolus injection or continuous infusion) can be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use. Formulations can contain, in addition to the active component, colorants, flavors, stabilizers, buffers, artificial and natural sweeteners, dispersants, thickeners, solubilizing agents, and the like. Compositions of the present disclosure can be in the form of an ointment, a gel, a plaster, an emulsion, a lotion, a foam, a cream of a mixed phase or amphiphilic emulsion system (oil/water-water/oil mixed phase), a liposome, a transfersome, a paste or a powder. Solutions or suspensions can be applied directly by conventional means, for example with a dropper, pipette or spray.

As used herein, the terms "control", "control cohort", "reference sample", and "control sample" refer to a sample obtained from a source that is known, or believed, to not be afflicted with the disease or condition for which a method or composition of the present disclosure is being used to identify. The control can include one control or multiple controls. In one embodiment, a reference sample or control sample is obtained from an individual who is not the subject or patient in whom a disease or condition is being identified using a composition or method of the disclosure. In another embodiment, the reference sample or control sample is obtained from the same individual in whom a disease or condition is being identified using a composition or method of the present disclosure at a separate time period (e.g., 1 week earlier, 2 weeks earlier, 1 month earlier, 1 year earlier, and the like) as the test sample.

As used herein, "susceptible" and "at risk" refer to having little resistance to a certain disease, disorder or condition, including being genetically predisposed, having a family history of, and/or having symptoms of the disease, disorder or condition.

As used herein, "expression level" of a protein refers to the process by which a gene product is synthesized from a gene encoding the gene product as known by those skilled in the art. The gene product can be, for example, DNA (deoxyribonucleic acid), RNA (ribonucleic acid) and protein. Expression level can be quantitatively measured by methods known by those skilled in the art such as, for example, northern blotting, amplification, polymerase chain reaction, microarray analysis, tag-based technologies (e.g., serial analysis of gene expression and next generation sequencing such as whole transcriptome shotgun sequencing or RNA-Seq), Western blotting, enzyme linked immunosorbent assay (ELISA), and combinations thereof.

In one aspect, the present disclosure is directed to a composition for treating sterile injury due to foreign object use. The composition includes: N-Acetylcysteine and an aminoquinoline. The two active agents of the composition work synergistically to mitigate local activity of neutrophil cells during exposure of the human body to a foreign material (plastic, metal, animal tissues and other materials).

N-Acetylcysteine ("NAC"; (2R)-2-acetamido-3-sulfanylpropanoic acid) increases the intracellular concentration of glutathione by reducing outside cystine to cysteine, thus providing a substrate for GSH synthesis. NAC directly scavenges reactive radicals such as HOC1 and reduces HO and $H_2O_2$ and indirectly provides a substrate for detoxification of peroxides. NAC is known to inhibit NF-κβ activation. NAC shows a low toxicity, augments neutrophil capacity for phagocytosis, and scavenges toxic oxygen radicals (ROS).

Suitable aminoquinolines include 4-amino quinoline (quinolin-4-amine), chloroquine ((RS)—N'-(7-chloroquinolin-4-yl)-N,N-diethyl-pentane-1,4-diamine), amodiaquine (4-[(7-chloroquinolin-4-yl)amino]-2-[(diethylamino)methyl]phenol), and hydroxychloroquine ((RS)-2-[{4-[(7-chloroquinolin-4-yl)amino]pentyl}(ethyl)amino]ethanol). A particularly suitable aminoquinoline is chloroquine.

Chloroquine ("CQ") is an alkylated 4-amino quinoline, water-soluble compound that readily crosses cell membranes and decrease cytokine activity by interfering with mRNA and DNA transcription. CQ inhibits late stages of autophagy and accelerates spontaneous neutrophil apoptosis (PS exposure, DNA fragmentation and caspase-3 activation). CQ downregulates Mcl-1 an antiapoptotic protein and prevents tissue injury by inhibiting lytic activity of metalloproteinases (MMPs).

The dose can vary within wide limits and is to be suited to the individual conditions in each individual case. The appropriate dosage will vary depending on the mode of administration, the particular condition to be treated and the effect desired.

Suitable dosage of N-Acetylcysteine can range from about 3 mM to about 10 mM. Suitable intravenous bolus dosages of N-Acetylcysteine can range from about 600 mg to about 2400. Suitable oral dosages of N-Acetylcysteine can range from about 600 mg to about 2400 mg.

Suitable dosage of an aminoquinoline can range from about 3 μM to about 50 μM.

In one aspect, the present disclosure is directed to a method for treating sterile injury due to foreign object use in a subject in need thereof. The method includes: administering to the subject a composition including N-Acetylcysteine and an aminoquinoline.

Suitable dosages of N-Acetylcysteine include those described herein.

Suitable aminoquinolines are described herein. Suitable dosages of aminoquinolines include those described herein.

The method can further include coating the foreign object with a composition comprising: N-Acetylcysteine and an aminoquinoline prior to use of the foreign object in the subject.

In one aspect, the present disclosure is directed to a composition comprising an endonuclease and an aminoquinoline.

A particularly suitable endonuclease is deoxyribonuclease I (DNase I). DNase I is secreted by exocrine glands, and found most abundantly in the pancreas and kidneys. It is also present in lower quantities in other tissues. DNase I cleaves DNA preferentially at phosphodiester linkages adjacent to a pyrimidine nucleotide.

Suitable dosages of an endonuclease range from about 3 µg/mL to about 30 µg/mL.

Suitable aminoquinolines include those described herein. Suitable dosages of aminoquinolines include those described herein.

In one aspect, the present disclosure is directed to a method for treating sterile injury due to foreign object use in a subject in need thereof. The method includes: administering a composition comprising: an endonuclease and an aminoquinoline.

Suitable endonucleases include those described herein. Suitable dosages of an endonuclease those described herein.

Suitable aminoquinolines include those described herein. Suitable dosages of aminoquinolines include those described herein.

The method can further include coating the foreign object with a composition comprising: an endonuclease and an aminoquinoline prior to use of the foreign object in the subject.

In one aspect, the present disclosure is directed to a medical device coated with a composition including N-Acetylcysteine, an aminoquinoline, an endonuclease, and combinations thereof.

Suitable endonucleases include those described herein. Suitable aminoquinolines include those described herein.

A particularly suitable composition for coating medical devices includes N-Acetylcysteine and an aminoquinoline.

Suitable medical devices for coating are those intended for use with mucosal tissue. Suitable medical devices include, for example, catheters (e.g., gastro-jejunostomy catheters, suprabubic catheters, thoracic catheters, ureteral catheters, urinary catheters, nephrostomy catheters, coronary catheters, central venous catheters, peripherally inserted catheters, Swan-Ganz hemodynamic catheters, dialysis catheters), tubes (e.g., endotracheal tubes, tracheostomy devices, brochiopulmonary stents, duodenal tubes, feeding tubes, rectal tubes, suction tubes, cardio-pulmonary bypass tubing), guidewires (e.g., urinary, cardio, interventional), urinary implantable devices, sutures, stents (e.g., ureteral, coronary), continence slings, electrosurgical cutting loops, stone retrieval snares, wound drains, ablation devices, cardiopulmonary devices, cardiothoracic devices, coronary balloons, embolic protection systems (e.g., vena cava filters), heart valves (e.g., surgical, transcatheter), endoscopes, mesh (e.g., hernia repair, dura mater), cranial fixation, and shunts (e.g., ventricular shunts).

Any suitable method known to those skilled in the art can be used to coat the medical device.

In one aspect, the present disclosure is directed to a method for diagnosing sterile injury due to foreign object use in a subject, the method comprising: obtaining a sample from the subject and analyzing the sample for mitochondrial DNA (mtDNA). The subject can further have sore throat pain. The subject can further have urethra pain. The subject can further have bladder pain.

The method can further include administering the subject a composition comprising N-Acetylcysteine, an aminoquinoline, an endonuclease, and combinations thereof to treat the sterile injury due to foreign object use in the subject.

In one aspect, the present disclosure is directed to a method for reducing neutrophil extracellular traps (NET) in a subject in need thereof. The method includes: administering a composition comprising N-Acetylcysteine, an aminoquinoline, an endonuclease, and combinations thereof.

Suitable aminoquinolines are disclosed herein. Suitable endonucleases are disclosed herein.

In one aspect, the present disclosure is directed to a method for reducing biofilm formation on a device. The method includes: contacting the device with a composition comprising N-Acetylcysteine, an aminoquinoline, an endonuclease, and combinations thereof.

Suitable devices include medical devices as disclosed herein.

Suitable aminoquinolines are disclosed herein. Suitable endonucleases are disclosed herein.

In one aspect, the present disclosure is directed to a method for promoting neutrophil phagocytosis of bacteria in response to mtDNA. The method includes: contacting the neutrophil with a composition comprising N-Acetylcysteine, an aminoquinoline, an endonuclease, and combinations thereof.

The bacteria can be gram positive bacteria, gram negative bacteria, and combinations thereof.

In one aspect, the present disclosure is directed to a method for reducing reactive oxygen species (ROS) production by a neutrophil. The method includes: contacting the neutrophil with a composition comprising N-Acetylcysteine, an aminoquinoline, an endonuclease, and combinations thereof.

In one aspect, the present disclosure is directed to a method for reducing pro-inflammatory protein production by a neutrophil. The method includes: contacting the neutrophil with a composition comprising N-Acetylcysteine, an aminoquinoline, an endonuclease, and combinations thereof.

The pro-inflammatory protein can be interleukin-1 beta (IL1β), interleukin-8 (IL-8), interleukin-6 (IL-6), interleukin-10 (IL-10), tumor necrosis factor alpha (TNF-α), toll-like receptor 9 (TLR-9), and combinations thereof.

In one aspect, the present disclosure is directed to a method for reducing tissue damage due to foreign object use in a subject in need thereof. The method includes: administering to the subject a composition including N-Acetylcysteine and an aminoquinoline.

The method can further include coating the foreign object with a composition comprising: N-Acetylcysteine, an endonuclease, an aminoquinoline prior, and combinations thereof, prior to use of the foreign object in the subject.

In one aspect, the present disclosure is directed to a method for reducing tissue damage due to foreign object use in a subject in need thereof. The method includes: administering to the subject a composition including an endonuclease and an aminoquinoline.

The method can further include coating the foreign object with a composition comprising: N-Acetylcysteine, an endonuclease, an aminoquinoline prior, and combinations thereof, prior to use of the foreign object in the subject.

EXAMPLES

Example 1

In this Example, presence of innate immune activators in the tracheal lavages of healthy human volunteers was determined to demonstrate a source of sterile injury.

Specifically, the presence of mitochondrial DNA (mtDNA) in the tracheal lavages of healthy human volunteers with clinical evidence of injury indicated by presence of sore throat was measured. Elevation of mtDNA was significant in the sore throat patients, when compared to those without injury as shown by PCR analysis. Furthermore, bacteriologic cultures showed normal tracheal flora and qPCR 16S RNA analysis indicated minimal bacteria presence in all positive and negative specimens.

Neutrophil cell response to mtDNA using Toll-Like Receptor-9 (TLR-9) activity and ROS production in neutrophils as indicators of activation was analyzed. Cocultures in vitro of human tracheal lavage samples from patients with sore throat and no sore throat with isolated neutrophils obtained from healthy blood donors reproduced neutrophil activity reminiscent of tracheal injury. Monoclonal antibodies (CD66b, CD16) specific for neutrophil identification, intracellular staining of TLR-9 and dihydrorhodamine 123 (ROS production) were utilized to stain cells prior to flow cytometry analysis. Once neutrophil injury was demonstrated, the addition of different concentrations of N-Acetylcysteine (NAC) 3 and 10 milliMoles/mL, and chloroquine (CQ) at concentrations of 50 micromoles/mL, resulted in a decrease in all indicators of neutrophil activation that were measured. Since sterile injury mediated neutrophil activation in the tracheal injury model, the injury was reproduced with mtDNA obtained from cultures of A549 cells, with a noticeable decrease in the neutrophil activation detected after exposing the activated neutrophil cells to NAC and CQ.

The synergistic activity of the compound including NAC and CQ relates to a dual level of action. First, NAC with a chemical formula $C_5H_9NO_3S$, increases the intracellular concentration of glutathione by reducing outside cystine to cysteine thus providing a substrate for GSH synthesis. NAC directly scavenges reactive radicals such as HOCl and reduces HO and $H_2O_2$ and indirectly provides a substrate for detoxification of peroxides. NAC is known to inhibit NF-κβ activation, and therefore, has a potential for modulation of inflammation and normal cell protection during certain stressful conditions (chemotherapy/radiation). The characteristics of NAC including low toxicity, augmentation of neutrophil capacity for phagocytosis, activity as a scavenger of toxic oxygen radicals (ROS) and inhibitor of NF-κβ activation make this medication an ideal neutrophil anti-inflammatory to prevent further tissue injury.

Because endosomal acidification is an essential step for TLR-9 activation, we used chloroquine (CQ) as a TLR-9 antagonist due to its weak base partition, and disruption of vesicular acidification of the endosomes, thus impairing their capacity to degrade and recycle molecules. CQ is an alkylated 4-amino quinoline, water-soluble compound that readily crosses cell membranes and decrease cytokine activity by interfering with mRNA and DNA transcription. CQ inhibits late stages of autophagy and accelerates spontaneous neutrophil apoptosis (PS exposure, DNA fragmentation and caspase-3 activation). CQ downregulates Mcl-1 an antiapoptotic protein and prevent tissue injury by inhibiting lytic activity of metallo-proteinases (MMPs). Without being bound by theory, it is believed that CQ intercalates into DNA, which may interfere with mtDNA binding to TLR-9.

Neutrophil elastases are a member of the chymotrypsin family of serine proteases that is stored in the azurophilic granules and are capable of degrading almost every extracellular protein inducing tissue destruction as seen in acute lung injury. We demonstrated that by using the combination of NAC/CQ the elastase concentration was greatly diminish in vitro, providing evidence for mitigation of neutrophil activity.

The use of NAC/CQ in synergy can provide a multi-level anti-neutrophil anti-inflammatory control at the extracellular and intracellular levels.

Example 2

In this Example, the effects ex vivo of a single dose DNase I and chloroquine on neutrophil activation was determined.

After approval by the IRB at Washington University St. Louis School of Medicine, consent from healthy humans admitted for short-stay surgery was obtained. Supernatants of tracheal lavages of sore throat and no sore throat subjects were co-cultured with PMN of healthy volunteers. Neutrophils were identified by flow cytometry using monoclonal antibody (mAb) CD66b/CD16. The ROS probe (DHR123) was used for assessment of ROS activity. IL-1β, TNF-α and IL-8 were measured by qPCR. Analysis was conducted in 18 subjects (6 with sore throat, 6 without sore throat and 6 controls). Each specimen was exposed to different concentrations of DNase I (3-30 μg/ml) and chloroquine 50 μM. MANOVA was utilized for statistical analysis with *p<0.05 considered statistically significant.

Figure 2:
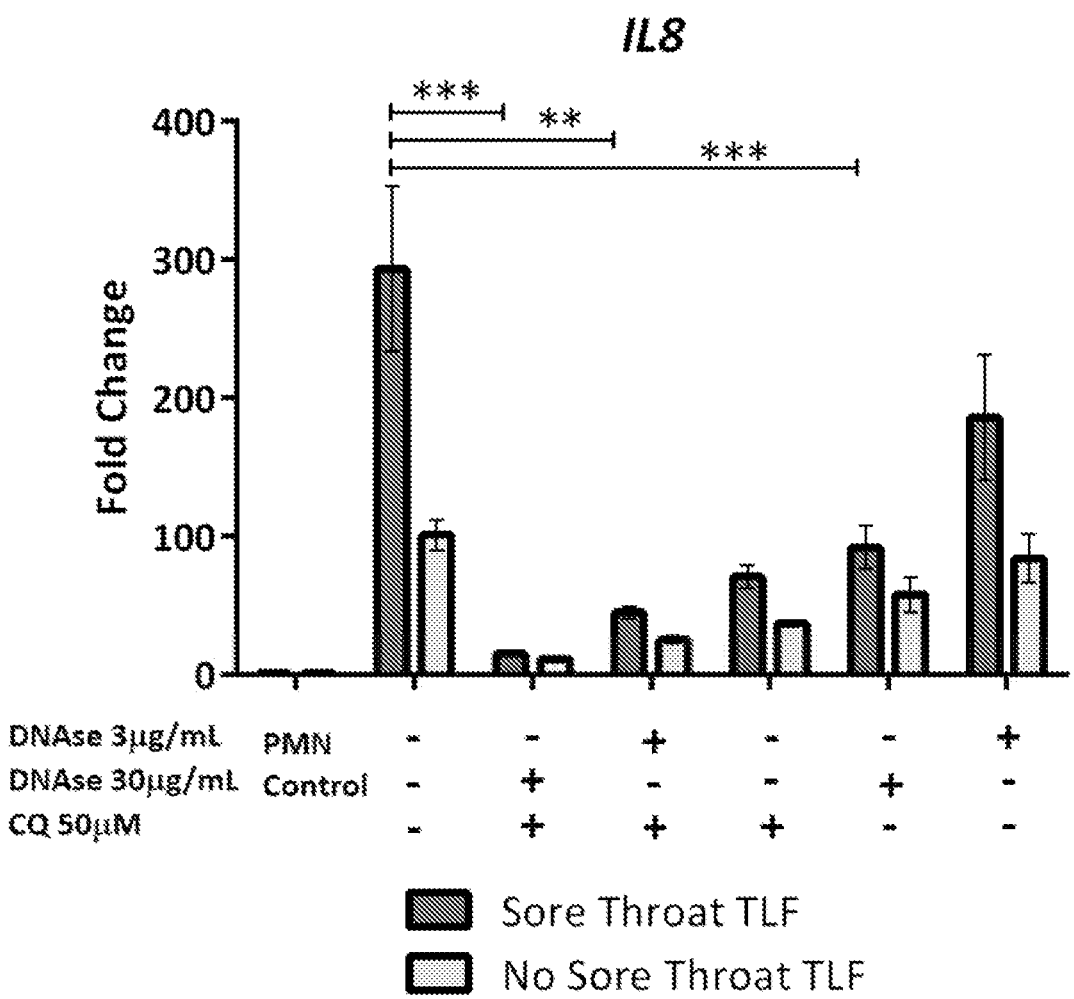
FIG. 2 is a graph depicting assessment of IL-8 in subjects administered DNase I and CQ as discussed in Example 2.
Figure 3:
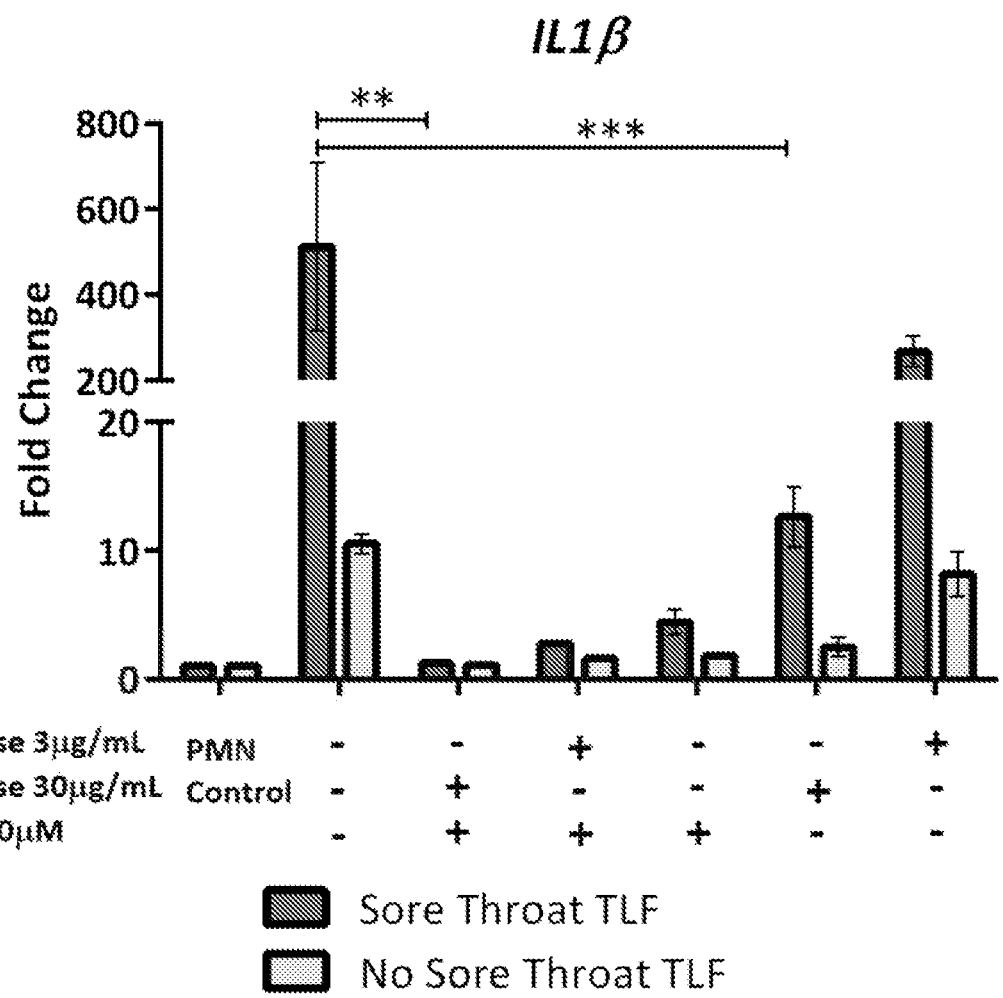
FIG. 3 is a graph depicting assessment of IL-1β in subjects administered DNase I and CQ as discussed in Example 2.
Figure 4:
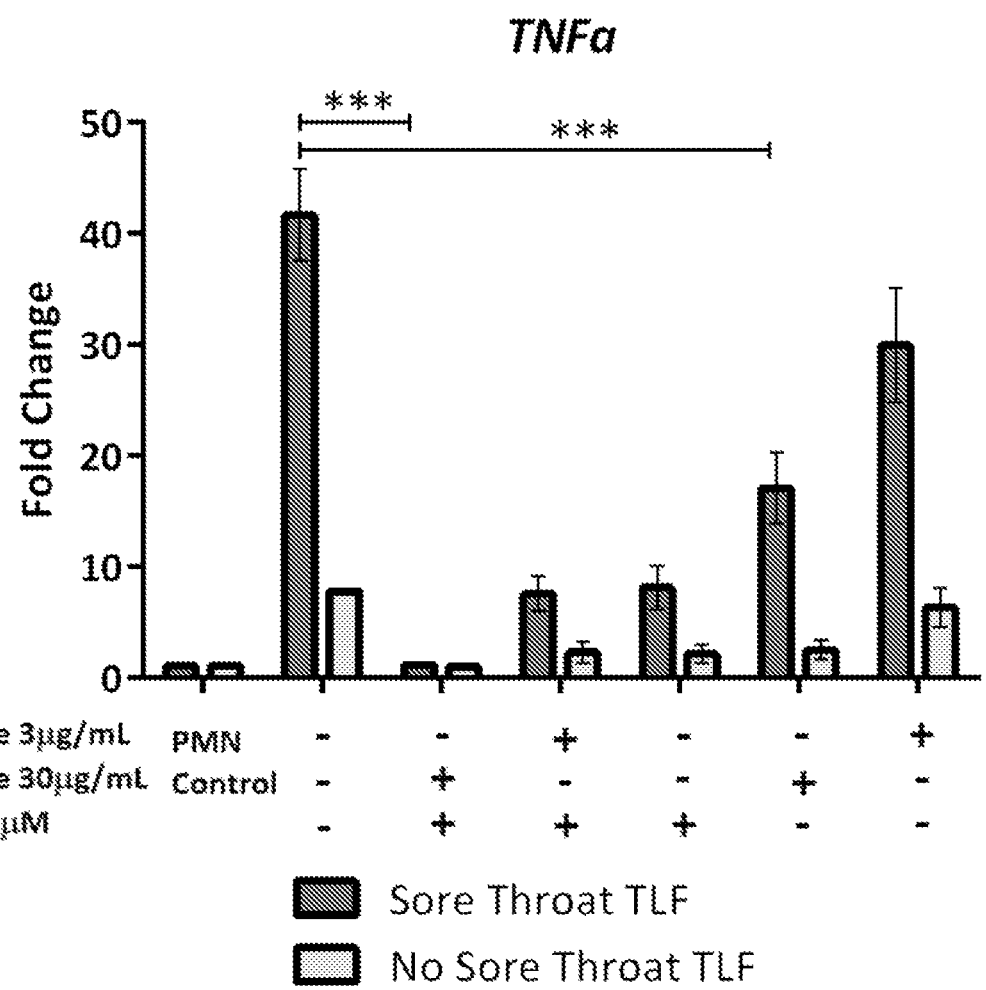
FIG. 4 is a graph depicting assessment of TNF-α in subjects administered DNase I and CQ as discussed in Example 2.

Compared to the no sore throat group, the sore throat group showed higher DHR-123 activity and elevated IL-1β, TNF-α, and IL-8. DNase I and chloroquine (CQ) noticeable decrease all variables analyzed: DHR123 p<0.0003 (FIG. 1), IL-1β p<0.007 (FIG. 2), TNF-α p<0.0000001 (FIG. 3), and IL-8 p<0.003 (FIG. 4). A single dose of DNase I/CQ ameliorated neutrophil activation as determined by evaluation of DHR123, TNF-α, IL-1β and IL-8. These results indicate potential benefit and possible tracheal protection with a single dose of DNase I/CQ.

Example 3

In this Example, the presence of sterile products such as damage associated molecular patterns (DAMPs) and in particular mitochondrial DNA (mtDNA) induction of local neutrophil activation was determined.

After approval by the IRB at Washington University St. Louis, consent was obtained from healthy humans. Supernatants of tracheal lavages of sore throat (n=6) and no sore throat (n=6) were analyzed for mtDNA. Cocultures of healthy donor neutrophils with tracheal lavage fluids (TLFs) of sore throat and uninjured subjects were analyzed for ROS (DHR-123), TLR-9 and human neutrophil elastase (ELANE). Flow cytometry was used to identify PMN with mAb CD66b/CD16PMN, and ROS activity, whereas qPCR was used for mtDNA, TLR-9 and ELANE identification. Each specimen was exposed to different concentrations of N-Acetylcysteine (NAC) (3-10 mM) and chloroquine (CQ) 50 μM. MANOVA was utilized for statistical analysis with *p<0.05; considered statistically significant.

Figure 5:
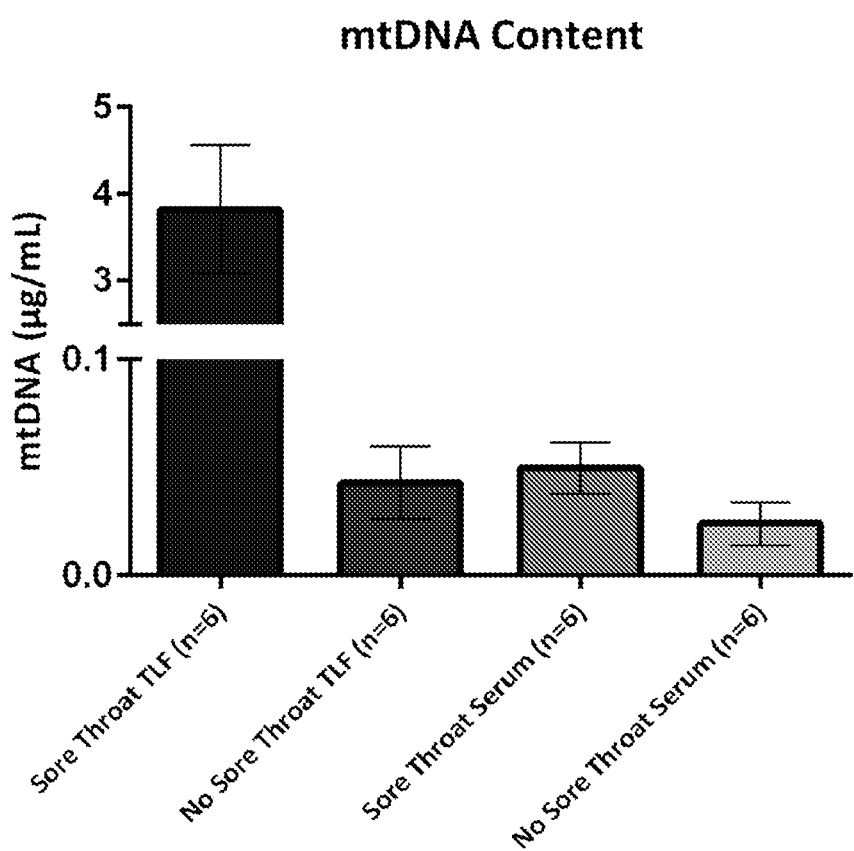
FIG. 5 is a graph depicting mtDNA content in tracheal lavage fluid (TLF) and serum from Sore Throat and No Sore Throat patients.
Figure 6:
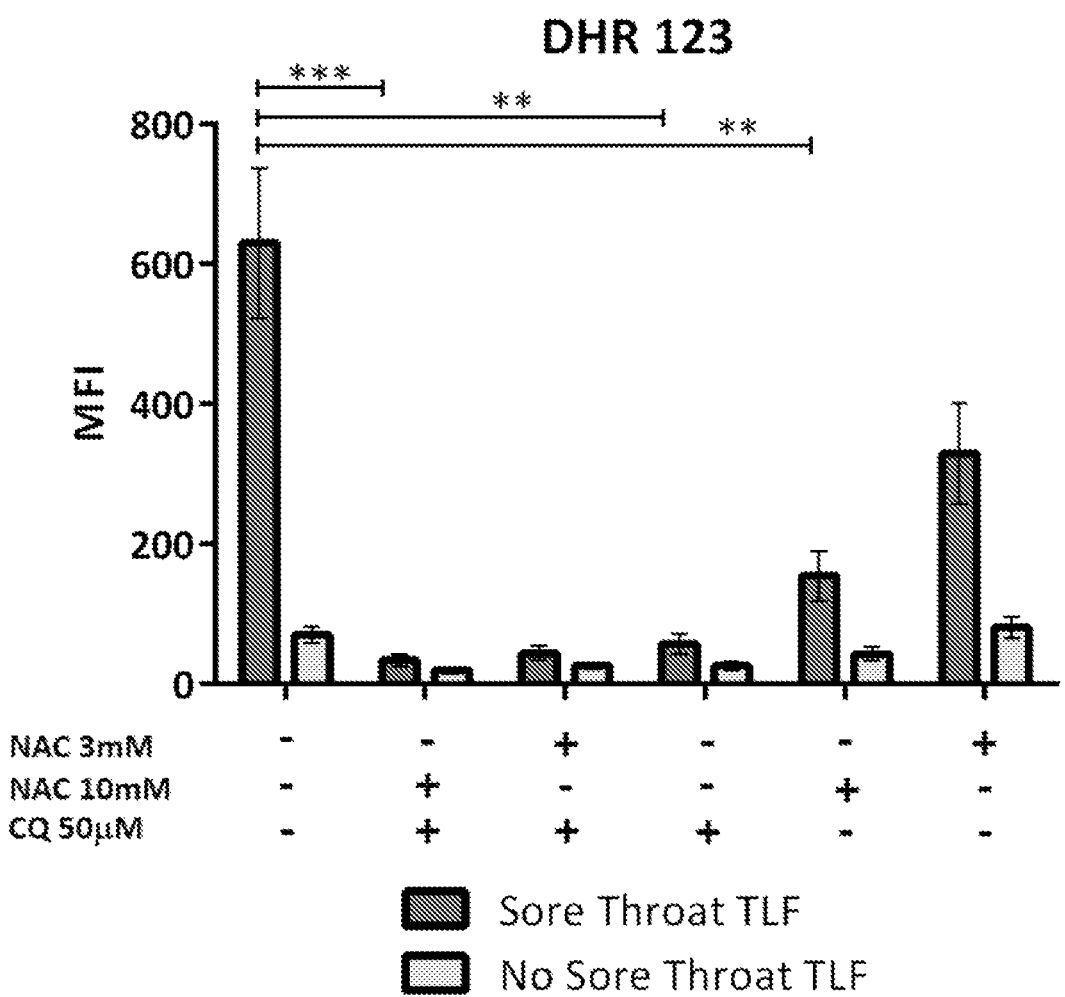
FIG. 6 is a graph depicting a decrease in DHR-123 after exposure to NAC/CQ. $p<0.0007$. Elevated levels of all parameters measured decreased, TLR-9 $p<0.009$ (FIG. 7) and elastase, neutrophil expressed (ELANE) $p<0.0002$ (FIG. 8), after exposure to NAC/CQ.
Figure 7:
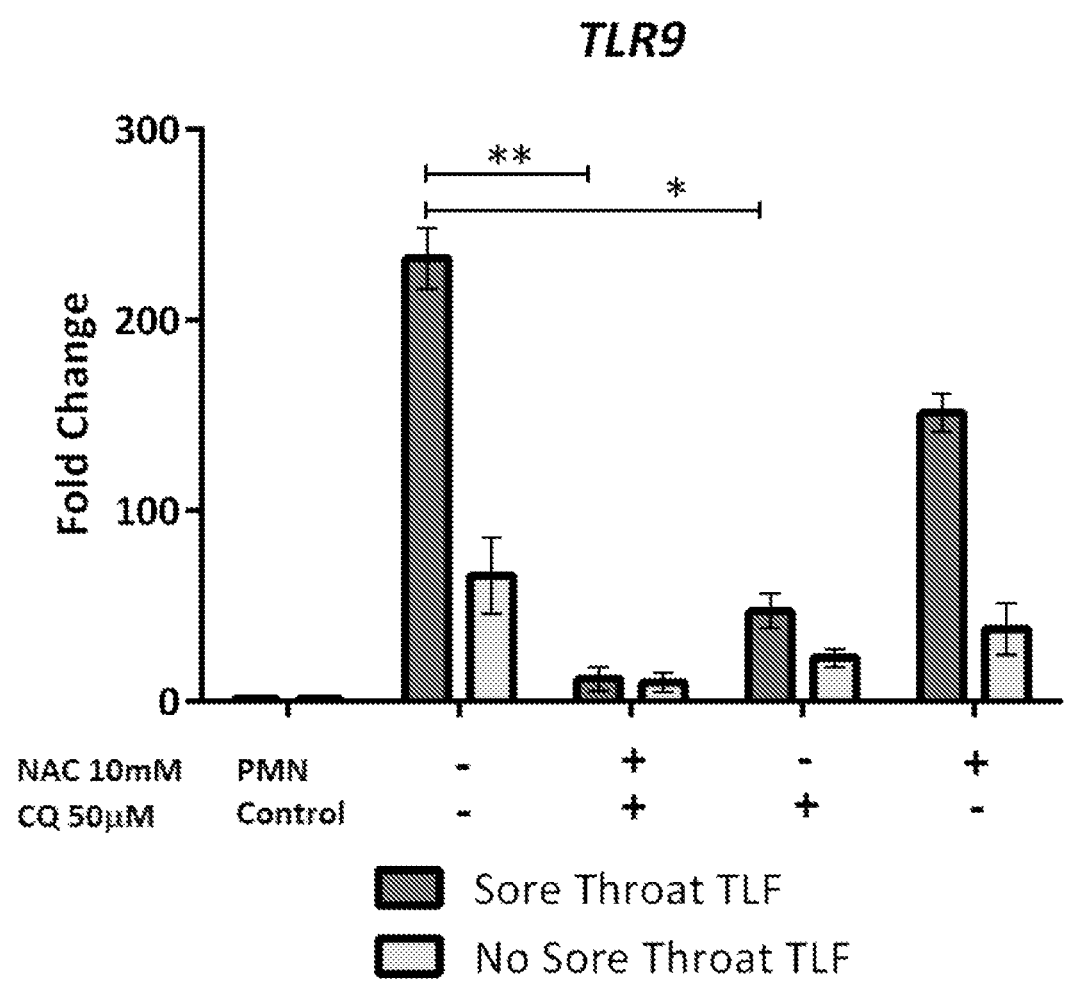
FIG. 7 is a graph depicting a decrease in TLR-9 after exposure to NAC/CQ. $p<0.009$. Elevated levels of all parameters measured decreased, TLR-9 $p<0.009$ (FIG. 7) and ELANE $p<0.0002$ (FIG. 8), after exposure to NAC/CQ.
Figure 8:
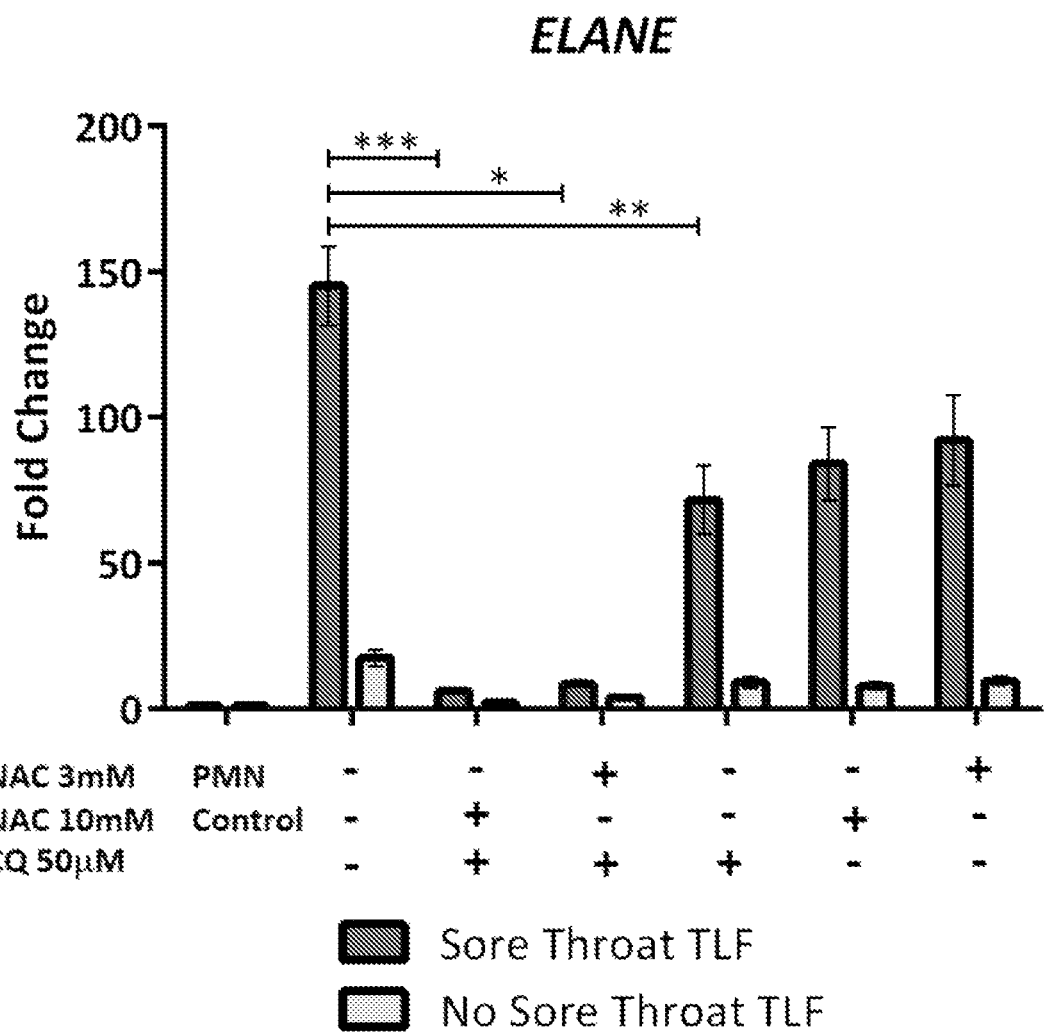
FIG. 8 is a graph depicting a decrease in ELANE after exposure to NAC/CQ. $p<0.0002$.

Elevated mtDNA level (3.29±0.73 μg/ml) detected in TLFs of sore throat patients were several fold higher than no sore throat (0.037±0.015 μg/ml (FIG. 5). Elevated levels of all parameters measured decreased: DHR-123 p<0.0007 (FIG. 6), TLR-9 p<0.009 (FIG. 7) and ELANE p<0.0002 (FIG. 8), after exposure to NAC/CQ.

These results demonstrated the presence of DAMPS (e.g., mtDNA) induced sterile tracheal inflammation and neutrophil activation as indicated by elevated ROS, TLR-9 and ELANE activity in sore throat injured patients. Neutrophil activation was reversed using the combination of NAC/CQ, which acted in a synergistic manner.

Example 4

In this Example, the effects ex vivo of a single dose DNase I and chloroquine on neutrophil activation was determined.

Subjects. After obtaining Washington University School of Medicine IRB approval for human studies, and informed written consent obtained, thirty-one adults aged 18-65, with American Society of Anesthesiologists health classification I/II requiring endotracheal intubation for same-day surgeries, were enrolled in the study. Any active autoimmune or pulmonary disease, hepatitis, cancer, previous tracheal surgery, surgery or endotracheal intubation within five days prior, smoking history less than six weeks prior, and immunosuppressive medication or azithromycin use excluded patients from participation in the study.

Specimen Collection. After placement of a MALLINCKRODT™ TaperGuard Evac ETT, two lavage samples were obtained from each patient using saline in a push/suction technique: one immediately following intubation, another prior to extubation. Wall suction was utilized to collect specimens in a sterile container (BARD® Medical, Covington, Ga., USA). 5 mL blood was collected at the end of surgery and processed. Two hours post-surgery the presence or absence of sore throat was documented.

Cell Isolation. TLF was washed in PBS +2% human AB serum and centrifuged at 1370 rpm for 7 minutes. Tracheal and blood cells were incubated for 30 minutes at room temperature with HETASEP™ (StemCell Technologies, Vancouver, BC, CA) and resuspended at 1×106 cells/mL for neutrophil isolation via negative selection with EASYSEP™ Neutrophil Enrichment Kits (StemCell Technologies) per manufacturer's instructions.

Flow Cytometry. After isolation, cells were stained with anti-human mAbs for CD16 (clone B73.1) and CD66b (clone G10F5) for neutrophil identification, and CD11b (clone ICRF44), CD54 (clone HA58), and TLR-9 (clone eB72-1665) as adhesion and activity markers, and subsequently characterized by fluorescence activated cell sorting (FACS; FACScan D×P10, BD Biosciences, San Jose, Calif., USA). Neutrophil respiratory burst was analyzed by priming cells with 1 μM PMA for 10 minutes followed by addition of 1 μM DHR-123 for 10 seconds and characterized by FACS. Thirty thousand events were analyzed with FLOWJO® X software (Tree Star, Ashland, Oreg., USA).

Functional Neutrophil Assay. To replicate neutrophil characteristics of both groups, neutrophils were isolated from 20 mL blood of healthy volunteers using the EASYSEP™ Neutrophil Enrichment Kits. Neutrophils were co-cultured with the following: TLF from subjects with or without sore throat and one of either 3 μg/mL DNase I, 30 μg/mL DNase I, or 1 μM inhibitory oligodeoxynucleotide ("iODN") (ODN TTAGGG A151; Invivogen, San Diego, Calif., USA); then incubated at 37° C.+5% $CO_2$ for 6 hours. Neutrophils were then stained for FACS and analyzed as previously described.

Supernatants from these co-cultures were incubated with human neutrophil elastase (HNE)-specific chromogenic substrate N-methoxysuccinyl-Ala-Ala-Pro-Val p-nitroanilide (MeO-SucAAPVpNA; Sigma Aldrich, St. Louis, Mo., USA) at 37° C.+5% $CO_2$ for one hour. After incubation, HNE activity was analyzed via spectrophotometry with a NanoDrop 2000 (ThermoFisher Scientific, Waltham, Mass., USA).

Quantitative PCR (qPCR). Primers for human MT-CYB and bacterial 16S rRNA (Integrated DNA Technologies, Coralville, Iowa, USA) were used to identify extracellular mtDNA in subject TLF and serum samples and exclude bacterial contamination. Primers for human IL1β, IL8, TNF-α, and TLR-9 were used to evaluate transcription of these markers in neutrophils co-cultured with TLF. MtDNA purified from human mitochondria and unstimulated healthy neutrophils were used to quantify extracellular mtDNA and inflammatory marker transcription. All experiments were run on a Bio-Rad CFX 96 thermocycler and analyzed with provided software (Bio-Rad Laboratories Inc., Hercules, Calif., USA). Conditions were 95° C. for 5 minutes, then 50 cycles of 95° C. for 30 seconds, 58° C. for 30 seconds, and 68° C. for 10 seconds and plate read; followed by melt curve analysis from 65-95° C.

TLR-9 Reporter Assay. HEK-BLUE™ hTLR-9 (Invivogen) cell line with transfected human TLR-9 and NF-κB/AP-1 alkaline phosphatase transgene were grown per manufacturer instructions. Cells were co-cultured at 37° C.+5% $CO_2$ for 6 hours in flat bottom 96 well plates with TLF as described previously. After incubation TLR-9 activation was analyzed by alkaline phosphatase release, measured using QUANTI-BLUE™ calorimetric detection medium (Invivogen) and spectrophotometry.

Statistical Analysis. All data was non-randomized and analyzed using SPSS v.17.0 (SPSS Inc., Chicago, Ill., USA). The continuous variables for neutrophil counts and median fluorescence intensity (MFI) data for identifying activation phenotypes in the two independent groups "Sore Throat" and "No Sore Throat" were compared between groups using student's t and Mann-Whitney U tests, respectively. Categorical variables—including mean age, gender, BMI, hypertension, hypercholesterolemia, sleep apnea, and intubation time in both groups—were compared using Fisher's exact test for contingency tables. Analyses of nonparametric qPCR data from TLF and blood serum in patients with and without sore throat for determining mtDNA and bacterial DNA concentrations were performed with a Kruskal-Wallis test, and subsequently tested post-hoc via Dunn's methods. Parametric pro-inflammatory transcript qPCR data from both groups treated with DNase I and iODN were analyzed via two-way MANOVA and tested post-hoc using Bonferroni sequential corrections.

Thirty-one patients admitted for same day surgery at Barnes Jewish Hospital without evidence of upper respiratory infection meeting the American Society of Anesthesiologists health classification I/II were asked for a 'yes' or 'no' response to whether they had sore throat 2 hours after extubation. Shown in Table 1, nearly half of all patients reported throat pain. Risk for sore throat was unrelated to gender, age, BMI, hypertension, serum cholesterol, obstructive sleep apnea, or intubation time. However, in line with previous studies, there was a non-significant bias in female patients with 61.5% reporting sore throat.

TABLE 1

Patient reported sore throat pain.

| Variable | Sore Throat | No Sore Throat | P |
|---|---|---|---|
| Number of patients, n | 13 | 18 | — |
| Age, years, mean (range) | 40.92 (26-56) | 40.78 (19-61) | 0.361 |
| Female, n (%) | 8 (61.64%) | 7 (38.89%) | 0.292 |
| Male, n (%) | 5 (38.46%) | 11 (61.11%) | 0.313 |
| BMI, n ± SEM | 30.46 ± 7.35 | 33.25 ± 12.45 | 0.442 |
| Hypertension, n (%) | 5 (38.46%) | 4 (22.22%) | 0.433 |
| Hypercholesterolemia, n (%) | 3 (23.08%) | 2 (11.11%) | 0.625 |
| Sleep apnea, n (%) | 2 (15.38%) | 1 (5.55%) | 0.558 |
| Intubation time, mins (range) | 213.38 (123-354) | 174.78 (55-363) | 0.395 |

Figure 9:
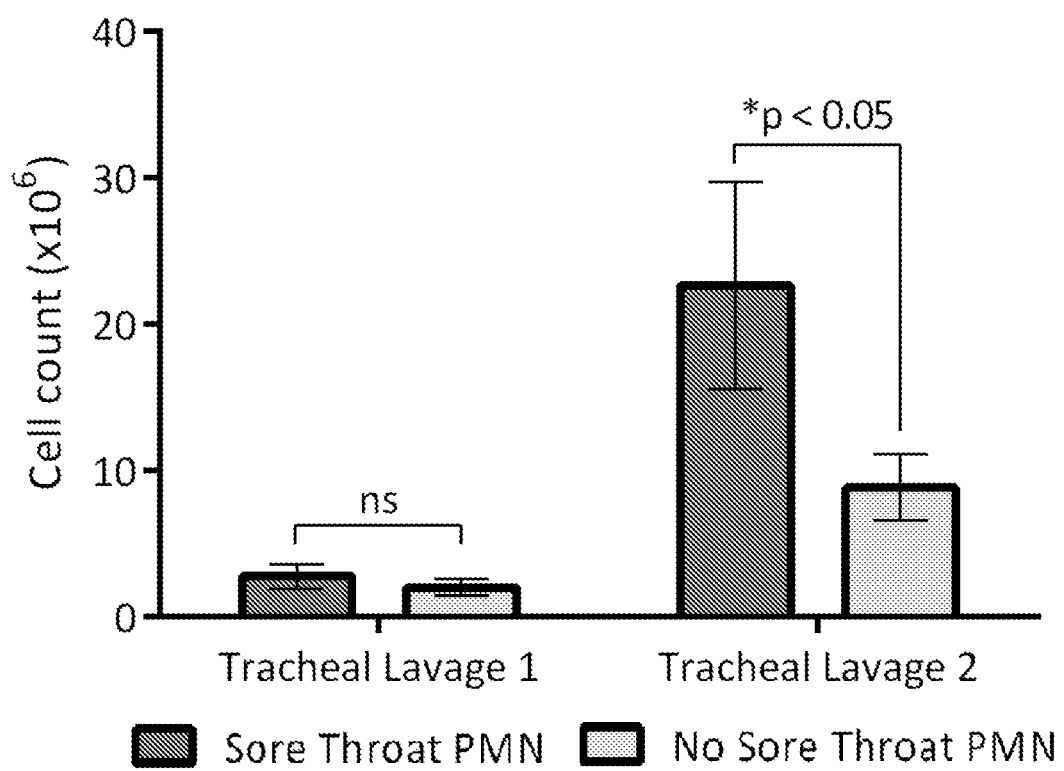
FIG. 9 is a graph depicting high numbers of TLF neutrophils found in sore throat patients at the time extubation. Total live cells in TLF were counted by trypan blue exclusion and neutrophils numbers were calculated by product of live cells and percent abundance of neutrophils as determined by fluorescence-activated cell sorting (FACS) analysis using a neutrophils Annexin V-SCC$^{hi}$ CD66b$^{lo-hi}$ CD16$^{lo-hi}$ gate for both tracheal lavages. Results are shown as a mean±SD derived from sore patients (N=13) and non-sore throat (N=18) patients.

TLFs from sore throat and non-sore throat patients at the time of intubation had low and comparable numbers of neutrophils (FIG. 9). In contrast, sore throat patients prior to extubation had significantly more neutrophils in their TLF when compared to non-sore throat patients. Neutrophils in sore throat TLF were also highly activated as they constitutively produced ROS (FIG. 10A) and had higher adhesion molecule expression involved in granulocyte trafficking into extracellular spaces as evident by higher plasma membrane levels of CD16, CD54 and CD66b (FIGS. 10B-10E).

Figure 11A:
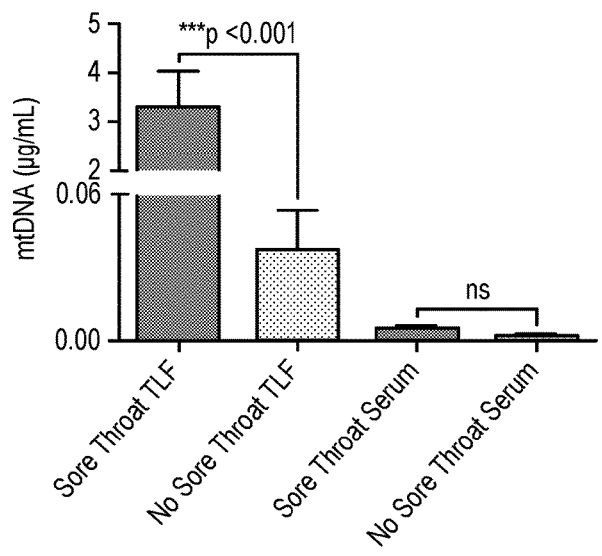
FIGS. 11A-11C are graphs depicting elevated mitochondrial DNA concentration observed in sore throat patient TLF.
Figure 11B:
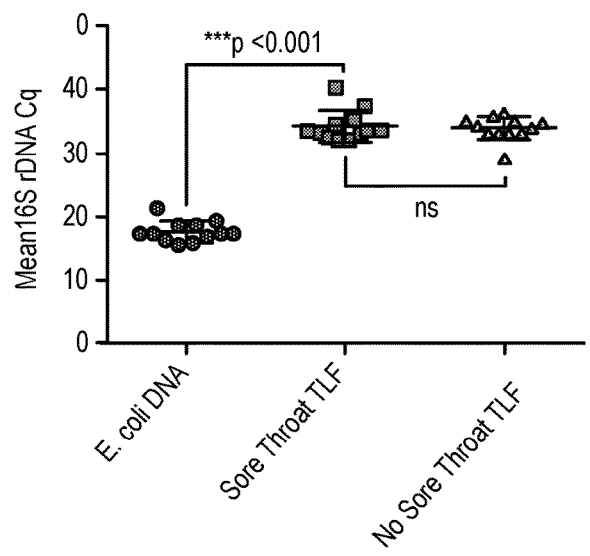
Figure 11C:
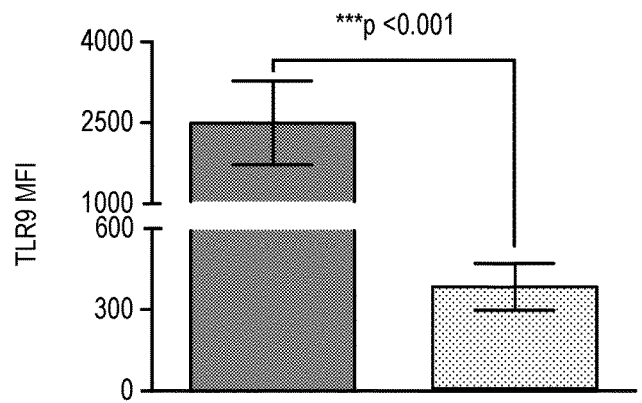

Unlike in the circulating blood TLF mtDNA levels were sharply elevated in sore throat patients when compared to patients who did not report throat pain (FIG. 11A). Importantly, mtDNA concentrations in the peripheral blood and TLF of non-sore throat patients were also similar indicating that surgery itself was not a cause of mtDNA release. The gene for 16S ribosomal RNA, a commonly used indicator for the presence of bacteria, was nearly undetectable in the TLF of both subject groups, indicating the absence of infection in the upper airway (FIG. 11B). TLR-9, a PRR that recognizes hypomethylated CpG DNA motifs found in mitochondria, expression was significantly elevated in TLF neutrophils of sore throat patients compared to those without sore throat (FIG. 11C).

Figure 12:
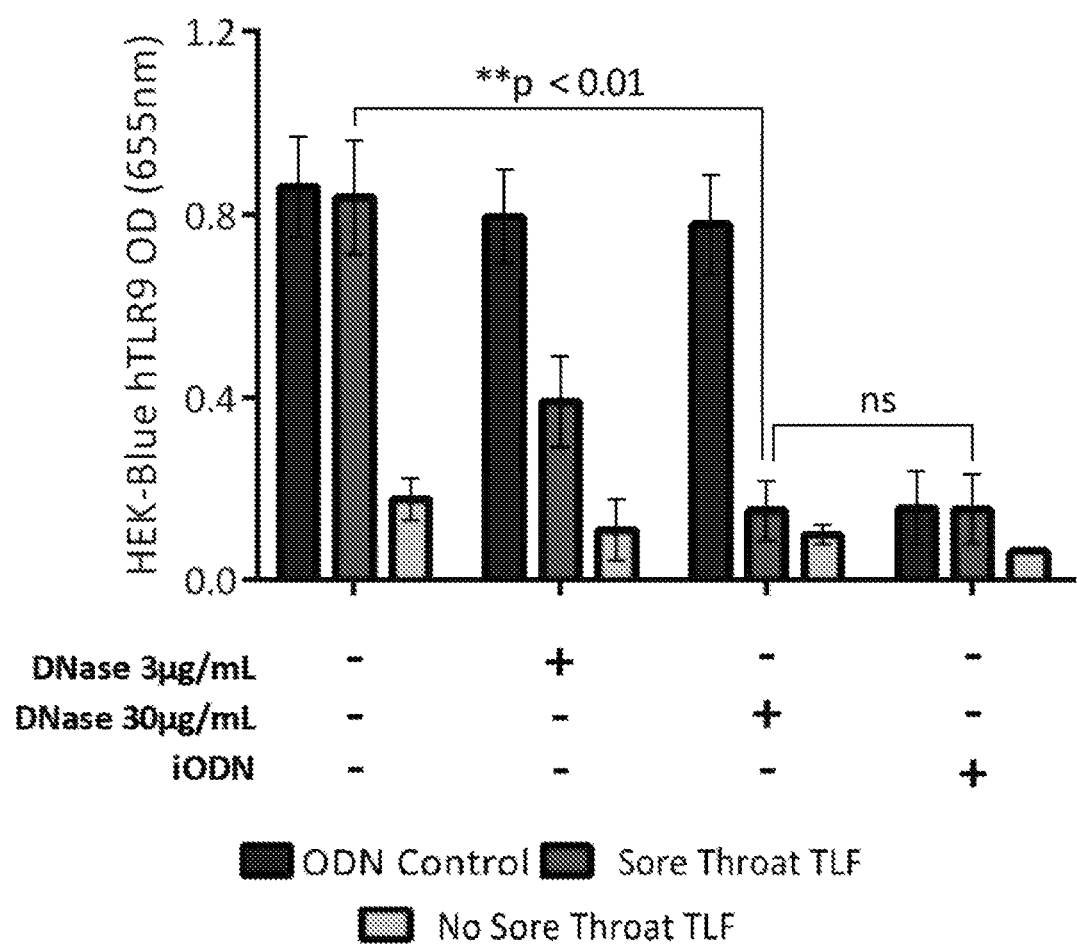
FIG. 12 is a graph depicting that mitochondrial DNA in sore throat TLF stimulated TLR-9 signaling. HEK293 TLR-9 reporter cell line was cultured alone or co-incubated with indicated TLFs left untreated or treated with graded amounts of DNase I or TLR-9 iODN. An ODN control was also included alongside the TLF samples. Six hours later supernatant was evaluated for target transgene NF-κB/AP-1 alkaline phosphatase activity by fluorescence spectroscopy. Data shown as a representative result from three independent experiments where mean alkaline phosphatase activity±SD is calculated from 8 sore throat and 8 non-sore throat patients.
Figure 13A:
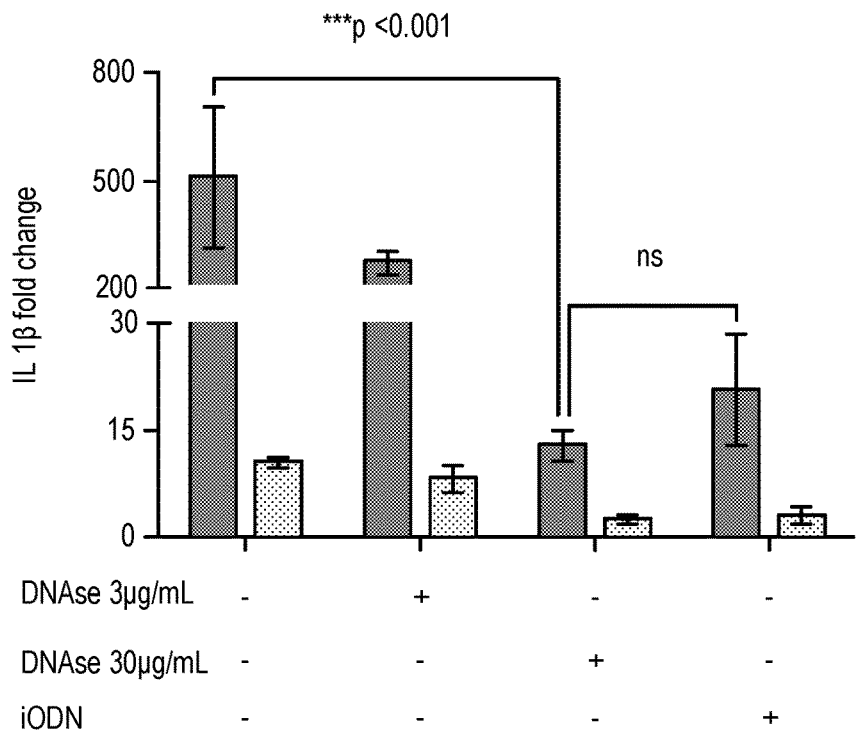
FIGS. 13A-13D are graphs depicting that sore throat TLF promoted neutrophil cytokine transcript accumulation in a TLR-9 dependent manner. Peripheral blood neutrophils isolated from healthy human volunteers were incubated with indicated TLF left untreated or treated with grade amounts of DNase I or TLR-9 iODN and three hours later neutrophils were fractionated for RNA and assessed for IL1β (FIG. 13A), TNF-α (FIG. 13B), IL8 (FIG. 13C), and TLR-9 (FIG. 13D) gene expression by qPCR. Data shown as a representative result from at least four independent experiments where mean levels±SD were normalized to uncultured freshly isolated neutrophils and were derived from 8 sore throat and 8 non-sore throat patients.
Figure 13B:
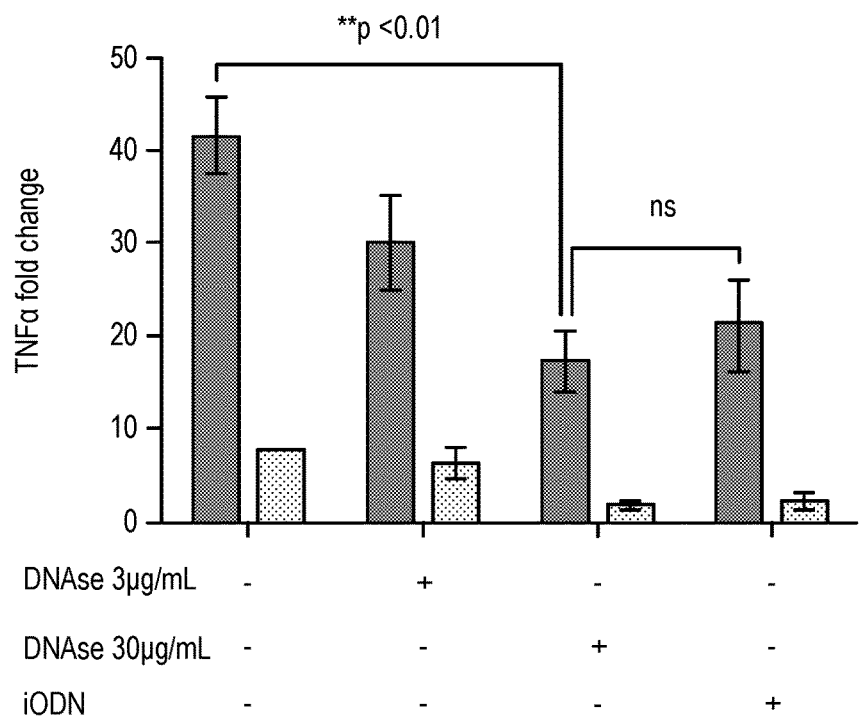
Figure 13C:
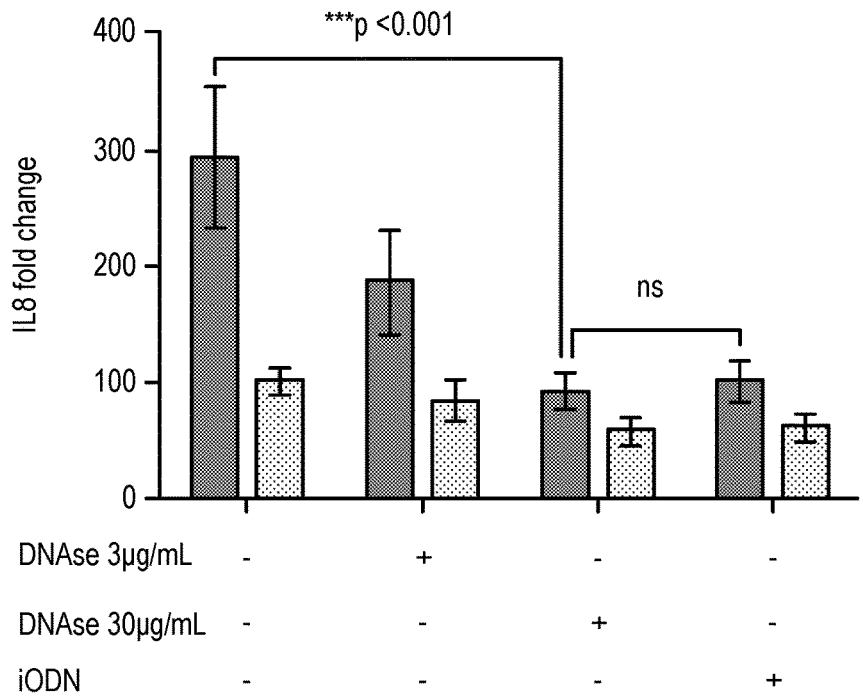
Figure 13D:
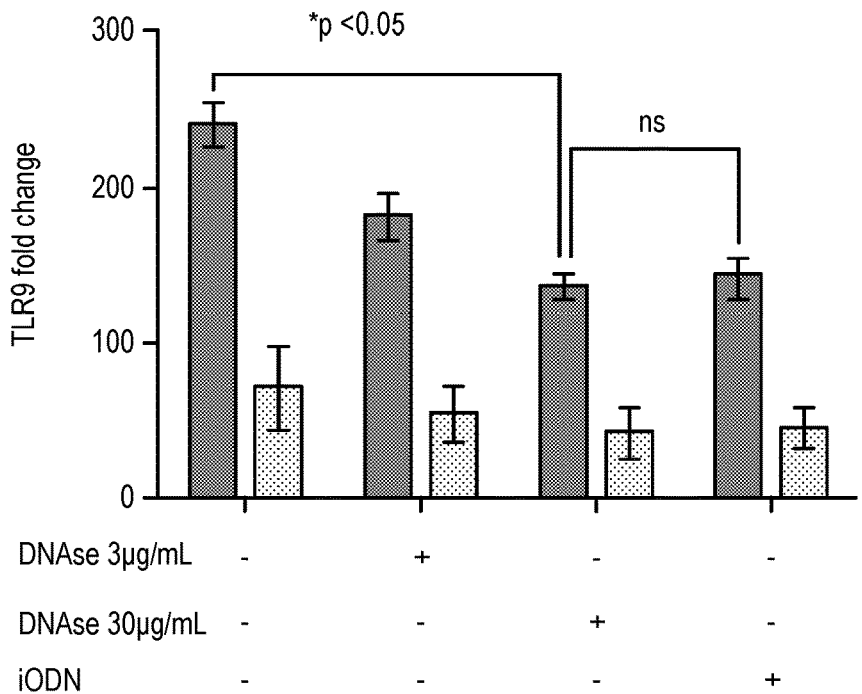
Figure 14A:
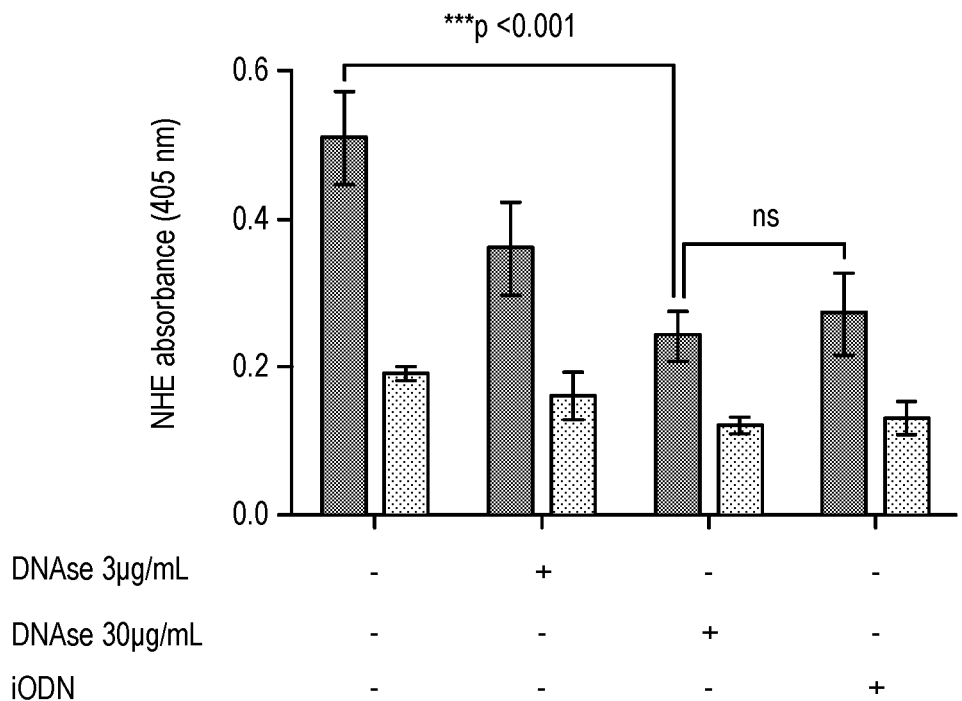
FIGS. 14A & 14B are graphs depicting that sore throat TLF drives TLR-9-mediated generation of ROS and elastase activity from neutrophils. Peripheral blood neutrophils isolated from healthy human volunteers were incubated with indicated TLF left untreated or treated with graded amounts of DNase I or TLR-9 iODN. One hour later neutrophils were assessed for human neutrophil elastase (HNE) activity by spectrophotometric assay (FIG. 14A) and ROS by DHR-123 dye staining (FIG. 14B). Data shown as a representative result from at least three independent experiments where mean levels±SD were derived from 8 sore throat and 8 non-sore throat patients.
Figure 14B:
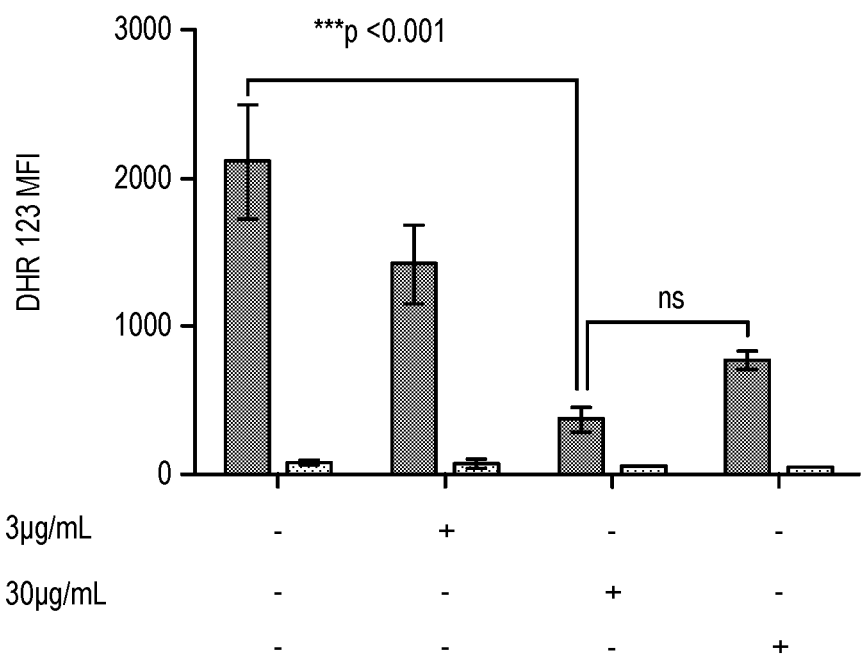

To assess the activity of mtDNA in TLF, sore throat and non-sore throat TLF was co-cultured with a HEK-293 reporter cell line with transfected human TLR-9 that measures engagement of CpG DNA through stimulating alkaline phosphatase transgene expression driven by the transcription factors NF-κB and AP-1 (FIG. 12). Sore throat TLF was nearly five-fold better at stimulating TLR-9-mediated reporter activity when compared to non-sore throat TLF. Pre-treatment of sore throat TLF with DNase I or blockade with inhibitory oligodeoxynucleotide (iODN) that inhibits human TLR-9 sharply reduced reporter activity. Sore and non-sore throat TLF was also co-cultured with neutrophils from healthy human volunteer peripheral blood (FIGS. 13A-13D). Sore throat TLF sharply induced the accumulation of IL1β, IL8, TNF-α, and TLR-9 mRNA transcripts. Notably, accumulation of these transcripts could also be largely reversed by pre-treatment of sore throat TLF with DNase I or iODN. Similar patterns of TLR-9-mediated neutrophil elastase release and ROS generation were also observed (FIGS. 14A & 14B). Taken together, these data demonstrated that extracellular mtDNA in sore throat patients stimulated neutrophil activation in a TLR-9 dependent manner.

The trachea is highly innervated with a subepithelial network of peripheral nerves that express transient receptor potential vanilloid calcium ion channels (TRPVs), which are well-established molecular sensors of pain. Accordingly, neutrophilia was significantly greater in patients that reported sore throat when compared to patients without sore throat. Sore throat patient neutrophils also constitutively produced higher levels of ROS. Several studies have shown that ROS directly promotes hyperalgesia in both acute and inflammatory settings. Additionally, sore throat patient TLF induced the release of human neutrophil elastase, a mediator of neuropathic pain. Recent work has revealed that neutrophil elastase generates pain through the activation of protease-activated TRPV4 receptors on nociceptive neurons. Finally, higher levels of IL-1β and TNF-α gene transcription were observed in sore throat TLF treated neutrophils. IL-1β and TNF-α increase sensitivity of nociceptors by promoting TRPV1 activation. Taken together, these data show that TLF from sore throat patients induce neutrophils to release significantly higher amounts of pro-inflammatory mediators known to trigger peripheral nerve pain.

Neutrophils from patients with ETT-mediated sore throat had a distinct activation phenotype, which was distinguishable from patients without sore throat by higher mean plasma membrane expression of the adhesion molecules CD66b, CD11b and CD54. High mean neutrophil adhesion molecule expression has been observed in many disease states. High mean CD66b expression has been reported in the synovium of rheumatoid arthritis patients, while elevated CD11b and CD54 levels have been noted in infiltrating neutrophils of infectious or ischemically injured tissue. In particular, elevated CD11b expression may play a critical role in neutrophil recruitment to the tracheal lumen as it is required for both transendothelial and transepithelial migration. CD54, otherwise known as I-CAM1, binds to CD11b, suggesting that sore throat neutrophils may additionally promote inflammation by binding to each other or to CD11b expressing myeloid cells such as macrophages. Therefore, these data indicate that ETT-mediated sore throat is linked to the generation of a neutrophil phenotype with augmented ability to transmigrate tissue barriers.

Neutrophil activation has primarily been described in the context of infection. However, in sore throat patients at time of extubation high levels of mtDNA was detected in their TLF indicating that neutrophil inflammation was generated by sterile injury. As mitochondria encode genes that share considerable homology with their bacterial ancestors, the possibility that bacterial infection could be triggering neutrophil activation in sore throat patients was considered. TLF cultures revealed only normal flora in the throat irrespective of whether or not they were derived from sore throat patients. Additionally, there were nearly undetectable levels of DNA that encode for the bacterial 16S ribosomal RNA in both sore throat and non-sore throat patient TLF.

Two independent approaches were used to determine if TLR-9 played a role in triggering inflammatory gene expression in neutrophils from patients with sore throat. First, TLR-9 signaling activity was tested in a HEK-293 reporter cell line and demonstrated that sore throat TLF triggered NF-κβ and AP-1 driven gene expression. These results were in line with observations showing that both transcription factors are activated by CpG DNA stimulation of TLR-9 on neutrophils. DNase I and iODN treatment of sore throat TLF prevented TLR-9 signaling, further confirming these results. Moreover, that this latter method also inhibited sore throat TLF-mediated inflammatory gene transcription, ROS, and elastase release.

Example 5

In this Example, the effect of N-acetylcysteine was determined on human neutrophils from healthy volunteers exposed to sore throat and no sore throat tracheal lavage fluid (TLF).

Approximately 20 mL peripheral blood from healthy volunteers was collected and incubated for 30 minutes at room temperature with HETASEP™ (Stem Cell Technologies, Vancouver, BC, CA) at a 5:1 blood:HETASEP™ ratio. After this incubation, the upper white blood cell layer was transferred to a new 15 mL conical tube, 10 mL PBS +2% FBS was added, and centrifuged again at 1370 rpm for 7 minutes. The cells were then resuspended at $1 \times 10^6$ cells/mL in 2 mL PBS +2% FBS for neutrophil isolation via negative selection with EASYSEP™ Neutrophil Enrichment Kits (Stem Cell Technologies) per manufacturer's instructions. Neutrophils were then resuspended at $1 \times 10^6$ cells/mL Human Neutrophil Media (RPMI-1640/-$Ca^{2+}$ $Mg^{2+}$/+10% FBS/+2 mM EDTA/+1 µg L-glutamine) and prepared for downstream applications.

Figure 15A:
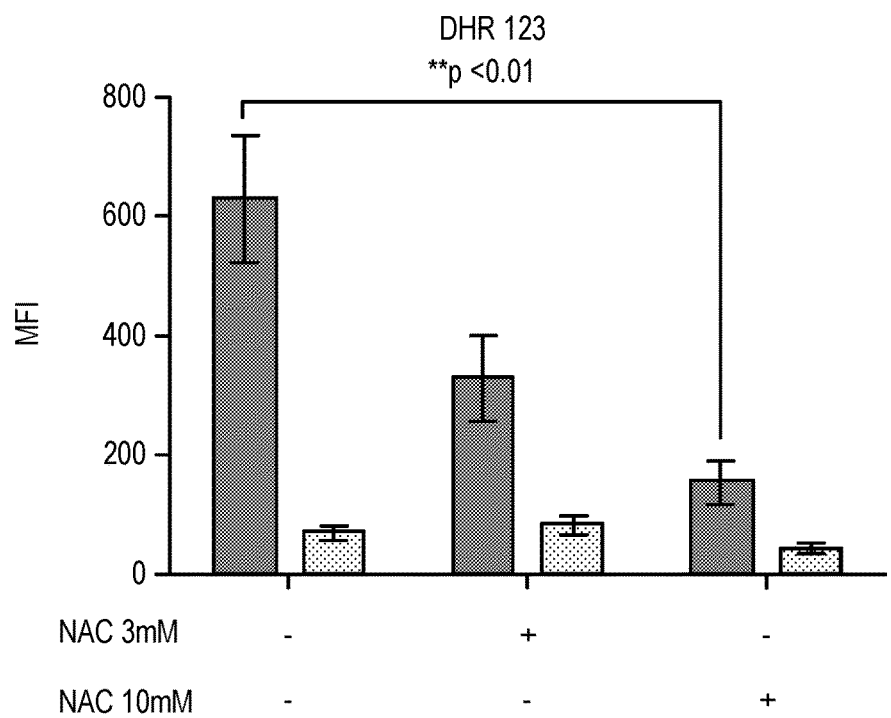
FIGS. 15A & 15B are graphs depicting staining of human neutrophils isolated from a healthy donor and co-treated with NAC and tracheal lavage fluid from individuals with or without a sore throat.
Figure 15B:
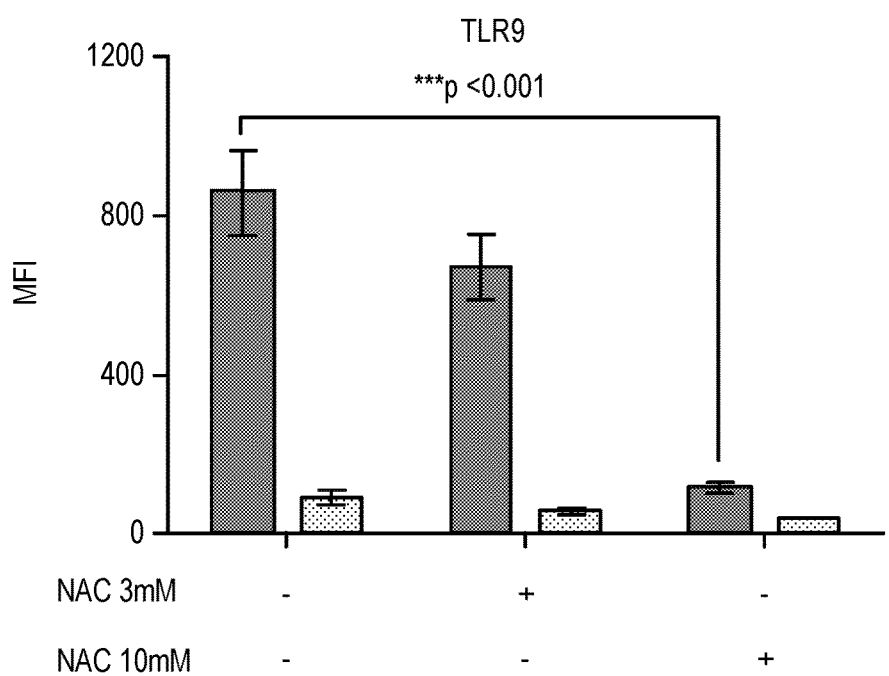
Figure 16A:
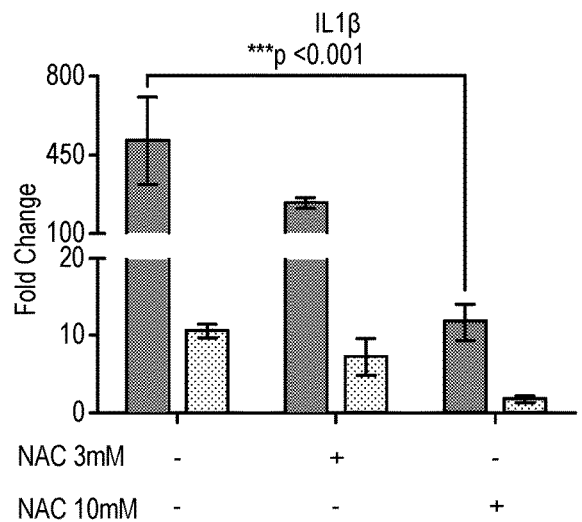
FIGS. 16A-16D are graphs depicting qPCR analysis of human IL1β (FIG. 16A), TNF-α (FIG. 16B), IL8, (FIG. 16C), and TLR-9 (FIG. 16D) messenger ribonucleic acid (mRNA) from human neutrophils isolated from a healthy donor and co-treated with NAC and tracheal lavage fluid from individuals with or without a sore throat.
Figure 16B:
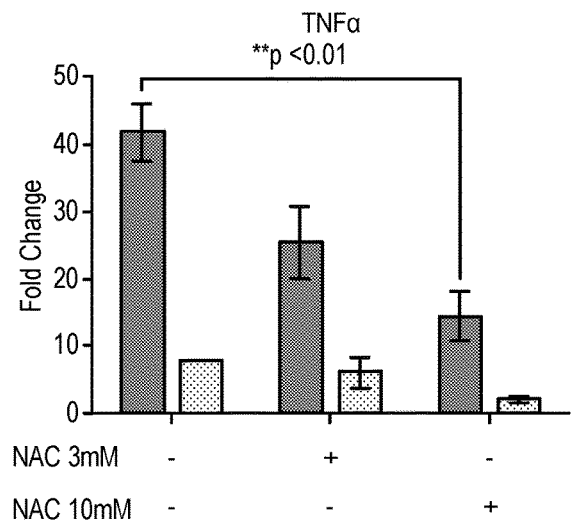
Figure 16C:
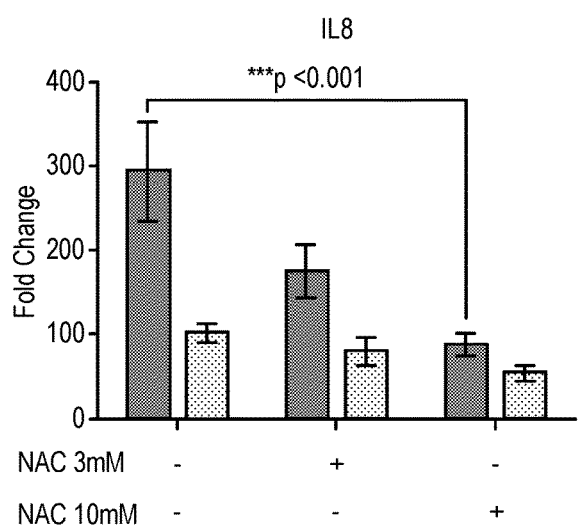
Figure 16D:
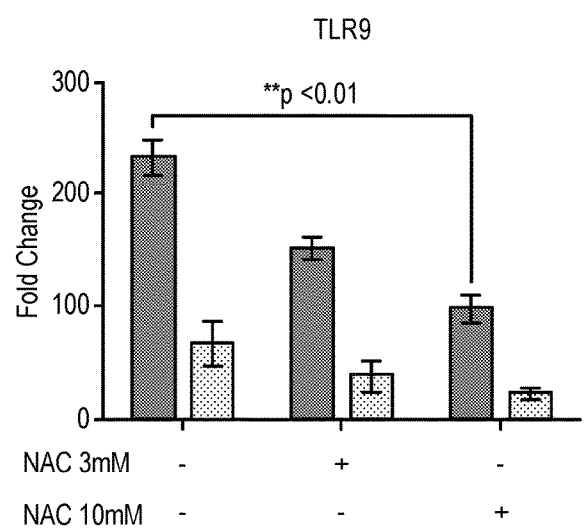

Approximately $2.5 \times 10^5$ human neutrophils from a healthy volunteer were added to each well of a 24-well plate, exposed sore throat and no sore throat tracheal lavage fluid (TLF) and concentration of 3 mM and 10 mM N-acetylcysteine (NAC), and incubated at 37° C.+5% $CO_2$ for 6 hours. After incubation, neutrophils were stained with anti-human monoclonal antibodies (eBioscience, San Diego, Calif., USA) for CD16 (clone B73.1) and CD66b (clone G10F5) for neutrophil population and activity identification (DHR-123, FIG. 15A), and also TLR-9 (FIG. 15B; clone eB72-1665) as an activity marker. These neutrophils were then subsequently characterized by fluorescence activated cell sorting (FACS; FACScan D×P10, BD Biosciences, San Jose, Calif., USA). Respiratory burst (FIG. 15A) was analyzed by priming CD16/CD66b-stained neutrophils with 1 µM phorbol 12-myristate 13-acetate (PMA) for 10 minutes at 37° C. followed by addition of 1 µM dihydrorhodamine 123 (DHR-123) for 10 seconds and characterized by FACS. Twenty thousand events were analyzed with the FLOWJO® X software (Tree Star, Ashland, Oreg., USA) and compared for differences using a Kruskal-Wallis test, and Dunn's post hoc test. **$p<0.01$.

Approximately $2.5 \times 10^5$ human neutrophils from a healthy volunteer were added to each well of a 24-well plate, exposed to sore throat and no sore throat tracheal lavage fluid (TLF) and concentration of 3 mM and 10 mM N-acetylcysteine (NAC), and incubated at 37° C.+5% $CO_2$ for 6 hours. After incubation, neutrophil mRNA was isolated via TRIzol® extraction and reverse transcribed into cDNA. Primers for human IL1β (FIG. 16A), TNF-α (FIG. 16B), IL8 (FIG. 16C), and TLR9 (FIG. 16D) (ThermoFisher Scientific, Waltham, Mass., USA) were used to evaluate transcription of these markers in neutrophils (FIGS. 16A-16D). Unstimulated healthy human peripheral blood neutrophils were used to quantify fold change in inflammatory marker transcription. All experiments were run on a Bio-Rad CFX 96 thermocycler and analyzed with the provided Bio-Rad CFX Manager software. Results were compared for differences using a Kruskal-Wallis test, and Dunn's post hoc test. $p<0.01$, *$p<0.001$.

Figure 17A:
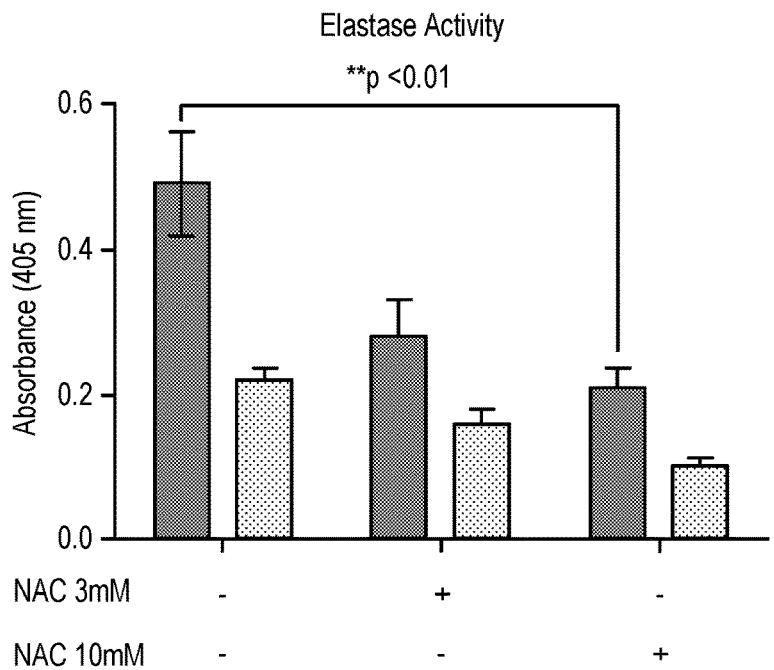
FIGS. 17A & 17B are graphs depicting human neutrophil elastase functional activity and gene expression (qPCR analysis of mRNA) of human neutrophils isolated from a healthy donor and co-treated with NAC and tracheal lavage fluid from individuals with or without a sore throat.
Figure 17B:
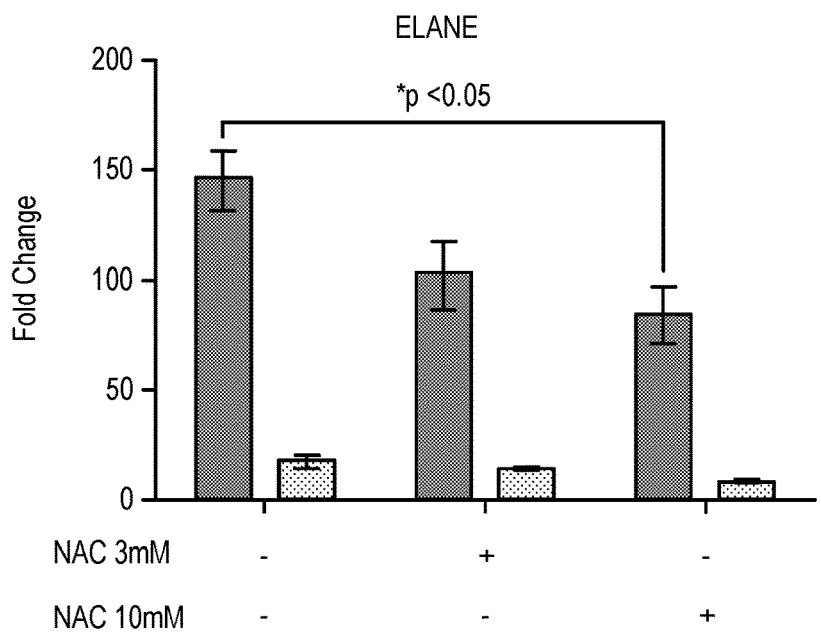

Approximately $2.5 \times 10^5$ human neutrophils from a healthy volunteer were added to each well of a 24-well plate, exposed to sore throat and no sore throat tracheal lavage fluid (TLF) and concentration of 3 mM and 10 mM N-acetylcysteine, and incubated at 37° C.+5% $CO_2$ for 6 hours. After incubation, neutrophil mRNA was isolated via TRIzol® extraction and reverse transcribed into cDNA. Human neutrophil elastase (FIG. 17A) activity was then measured by the enzymatic hydrolysis of the HNE-specific chromogenic substrate N-methoxysuccinyl-Ala-Ala-Pro-Val p-nitroanilide (MeO-SucAAPVpNA; Sigma Aldrich, St. Louis, Mo., USA) into 4-nitroaniline. 100 µL of the neutrophil co-culture supernatants were incubated with 200 µL 1 mM MeO-SucAAPVpNA in 0.1 M HEPES (pH 7.5) buffer at 37° C.+5% $CO_2$ for one hour. After incubation, substrate cleavage into 4-nitroaniline by HNE in the supernatants was measured by absorbance at 405 nm via spectrophotometry (NanoDrop 2000, ThermoFisher Scientific, Waltham, Mass., USA). Primers for human neutrophil elastase (ELANE; ThermoFisher Scientific) were used to evaluate transcription of this marker in neutrophils (FIG. 17B). Unstimulated healthy human peripheral blood neutrophils were used to quantify fold change in marker transcription. qPCR experiments were run on a Bio-Rad CFX 96 thermocycler and analyzed with the provided Bio-Rad CFX Manager software. Results were compared for differences using a Kruskal-Wallis test, and Dunn's post hoc test. *$p<0.05$, **$p<0.01$.

Example 6

In this Example, dose response for chloroquine was determined for human embryonic kidney cell line and human neutrophils.

Figure 18:
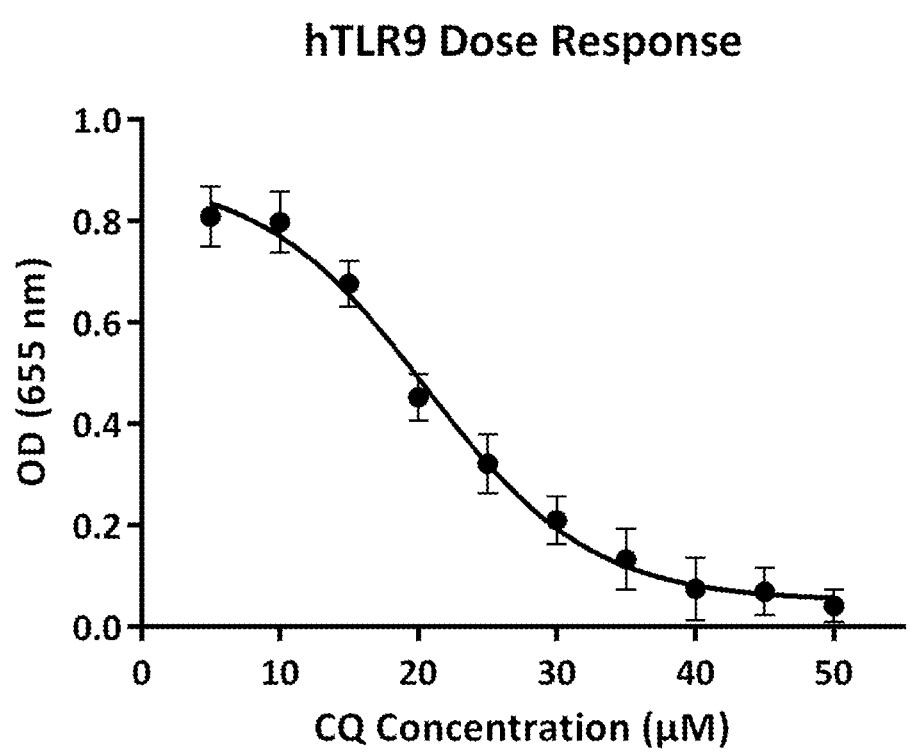
FIG. 18 is a graph depicting a dose response curve for human embryonic kidney (HEK293) cell line transfected with human TLR-9 (hTLR-9) and exposed to pro-inflammatory 5'-C-phosphate-G-3' (CpG) ODN and treated with chloroquine (CQ).

A human embryonic kidney (HEK293) cell line transfected with human TLR-9 and NF-κB/AP-1 alkaline phosphatase transgenes (HEK-Blue™ hTLR-9; Invivogen, San Diego, Calif., USA) was grown per manufacturer instructions. After three passages, cells were transferred to 48-well plates at approximately $1 \times 10^5$ cells/well and incubated at 37° C.+5% $CO_2$ for 30 minutes to adhere. Cells were then exposed to 3 µM pro-inflammatory 5'-C-phosphate-G-3' (CpG) ODN and concentrations between 0-50 µM of chloroquine (CQ) in 5 µM increments, and incubated at 37° C.+5% $CO_2$ for 6 hours. After incubation, TLR-9 activation was analyzed by alkaline phosphatase release, as measured using QUANTI-Blue™ calorimetric detection medium (Invivogen) via spectrophotometry (NanoDrop 2000; ThermoFisher Scientific, Waltham, Mass., USA). (FIG. 18 corrected from log(OD) responses for visual purposes).

Approximately 20 mL peripheral blood from healthy volunteers was collected and incubated for 30 minutes at room temperature with HETASEP™ (Stem Cell Technologies, Vancouver, BC, CA) at a 5:1 blood:HETASEP™ ratio. After this incubation, the upper white blood cell layer was transferred to a new 15 mL conical tube, 10 mL PBS +2% FBS was added, and centrifuged again at 1370 rpm for 7 minutes. The cells were then resuspended at $1 \times 10^6$ cells/mL in 2 mL PBS +2% FBS for neutrophil isolation via negative selection with EASYSEP™ Neutrophil Enrichment Kits (Stem Cell Technologies) per manufacturer's instructions. Neutrophils were then resuspended at $1 \times 10^6$ cells/mL Human Neutrophil Media (RPMI-1640/-$Ca^{2+}$ $Mg^{2+}$/+10% FBS/+2 mM EDTA/+1 µg L-glutamine) and prepared for downstream applications. mRNA was immediately isolated from approximately $1 \times 10^6$ neutrophils via TRIzol® (ThermoFisher Scientific) extraction and frozen at −70° C. for use as a baseline in downstream qPCR applications.

Figures 19A, 19B:
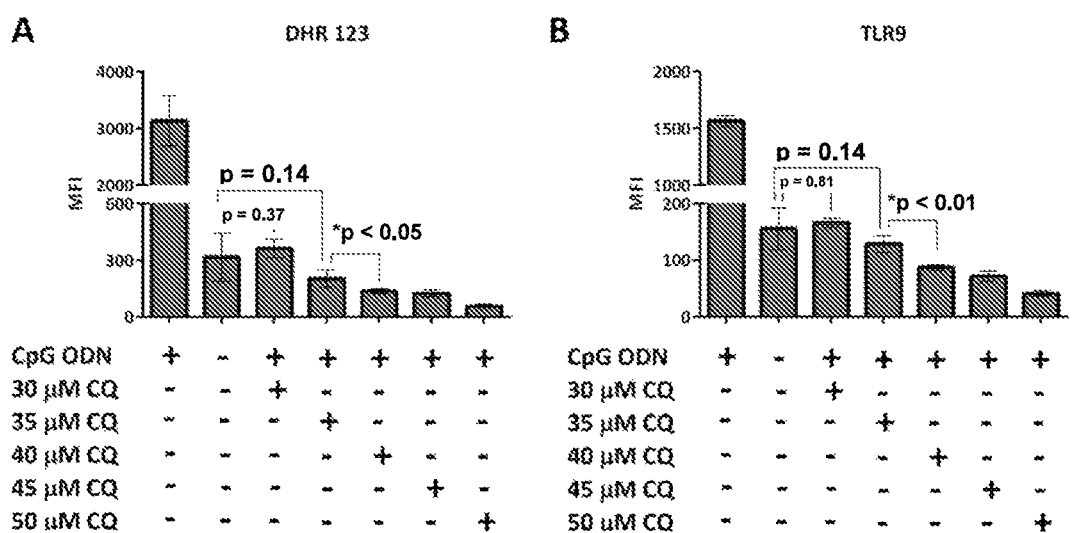
FIGS. 19A & 19B are graphs depicting DHR-123 for respiratory burst (FIG. 18A) and TLR-9 (FIG. 18B) in human neutrophils exposed to pro-inflammatory 5'-C-phosphate-G-3' (CpG) ODN and treated with varying concentrations of chloroquine (CQ).

Approximately $2.5 \times 10^5$ human neutrophils from a healthy volunteer were added to each well of a 24-well plate, exposed to 3 µM pro-inflammatory 5'-C-phosphate-G-3' (CpG) ODN and concentrations between 30-50 µM of chloroquine (CQ) in 5 µM increments, and incubated at 37° C.+5% $CO_2$ for 6 hours. After incubation, neutrophils were stained with anti-human monoclonal antibodies (eBioscience, San Diego, Calif., USA) for CD16 (clone B73.1) and CD66b (clone G10F5) for neutrophil population and activity identification (DHR-123, FIG. 19A), and also TLR-9 (FIG. 19B; clone eB72-1665) as an activity marker. These neutrophils were then subsequently characterized by fluorescence activated cell sorting (FACS; FACScan DxP10, BD Biosciences, San Jose, Calif., USA). Respiratory burst (FIG. 19A) was analyzed by priming CD16/CD66b-stained neutrophils with 1 μM phorbol 12-myristate 13-acetate (PMA) for 10 minutes at 37° C. followed by addition of 1 μM dihydrorhodamine 123 (DHR-123) for 10 seconds and characterized by FACS. Twenty thousand events were analyzed with the FLOWJO® X software (Tree Star, Ashland, Oreg., USA) and compared for differences using a Kruskal-Wallis test, and Dunn's post hoc test. *p<0.05, **p<0.01.

Figures 20A, 20B, 20C, 20D:
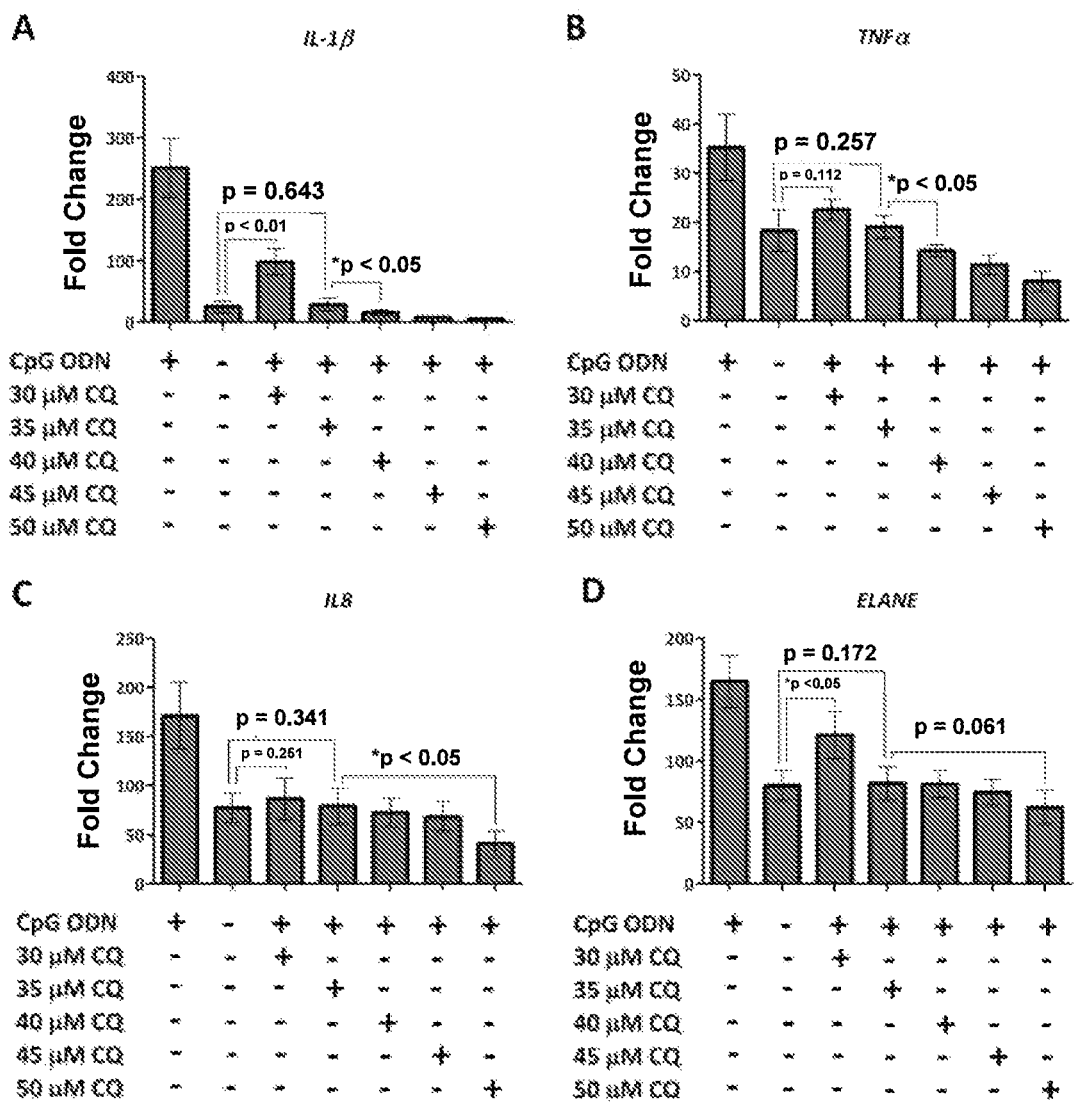
FIGS. 20A-20D are graphs depicting human neutrophils from a healthy volunteer exposed to pro-inflammatory 5'-C-phosphate-G-3' (CpG) ODN and chloroquine (CQ) analyzed for expression of human IL1β (FIG. 20A), TNF-α (FIG. 20B), IL8 (FIG. 20C), and ELANE (FIG. 20D).

Approximately $2.5 \times 10^5$ human neutrophils from a healthy volunteer were added to each well of a 24-well plate, exposed to 3 μM pro-inflammatory 5'-C-phosphate-G-3' (CpG) ODN and concentrations between 30-50 μM of chloroquine (CQ) in 5 μM increments, and incubated at 37° C.+5% $CO_2$ for 6 hours. After incubation, mRNA was isolated via TRIzol® extraction and reverse-transcribed into cDNA. Primers for human IL1β (FIG. 20A), TNF-α (FIG. 20B), IL8 (FIG. 20C), and ELANE (FIG. 20D) (ThermoFisher Scientific) were used to evaluate transcription of these markers against mRNA from neutrophils immediately isolated from peripheral blood as a baseline. All experiments were run on a Bio-Rad CFX 96 thermocycler and analyzed with the provided Bio-Rad CFX Manager software. Results were compared for differences using a Kruskal-Wallis test, and Dunn's post hoc test. *p<0.05, **p<0.01.

Example 7

In this Example, porcine neutrophils isolated from tracheal lavage fluid (TLF) were analyzed from animals with untreated and N-acetylcysteine/chloroquine-treated endotracheal tubes.

After placement of untreated and N-acetylcysteine/chloroquine-treated size 7.0 mm I.D. endotracheal tubes in pig tracheae, approximately 10 mL tracheal lavage fluid (TLF) from both groups was collected and centrifuged at 1370 rpm for 7 minutes to separate cells from unwanted extracellular material. TLF supernatants were then aliquoted and frozen at −20° C. The resulting cell pellets were then resuspended in 5 mL PBS +2% FBS and incubated at room temperature for 5 minutes. The cells were then incubated for 30 minutes at room temperature with HETASEP™ (Stem Cell Technologies, Vancouver, BC, CA) at a 5:1 TLF cells:HETASEP™ ratio. After this incubation, the upper cell layer was transferred to a new 15 mL conical tube and centrifuged again at 1370 rpm for 7 minutes. The cells were then resuspended at $1 \times 10^5$ cells/mL in 2 mL PBS +2% FBS for neutrophil isolation via negative selection with EASYSEP™ Neutrophil Enrichment Kits (Stem Cell Technologies) per manufacturer's instructions. Neutrophils were then prepared for downstream applications (i.e., FACS, qPCR, functional assays). This was done at time points 0, 3, and 6 hours.

Figure 21A:
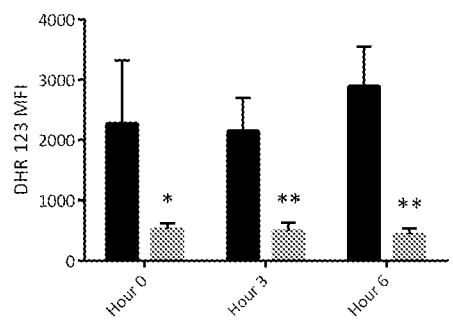
FIGS. 21A-21F are graphs depicting staining of porcine neutrophils isolated from tracheal lavage fluid for DHR-123 (FIG. 21A), CD11a (FIG. 21B), CD11b (FIG. 21C), CD54 (FIG. 21D), CD62L (FIG. 21E), and cell count (FIG. 21F). $*p<0.05$, $p<0.01$, $*p<0.001$.
Figure 21B:
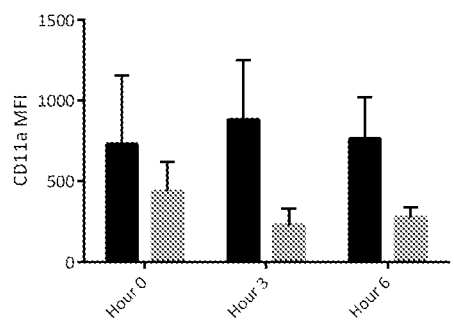
Figure 21C:
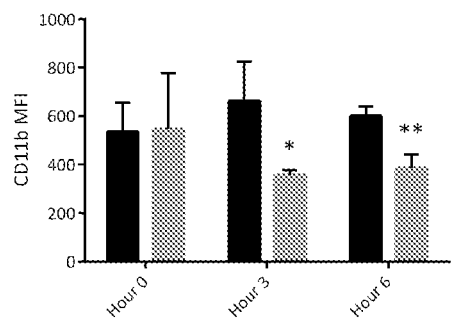
Figure 21D:
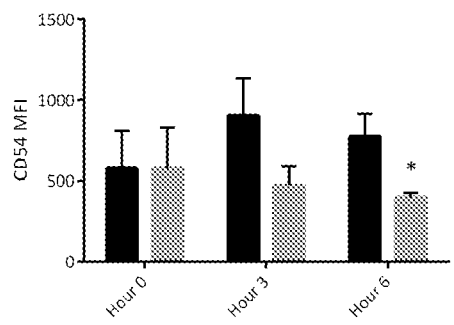
Figure 21E:
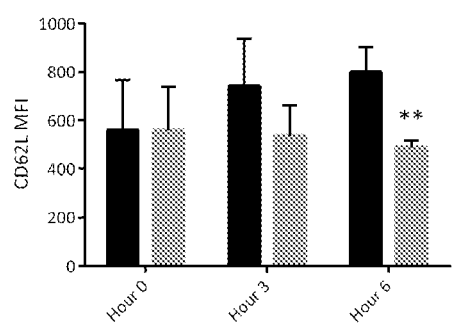
Figure 21F:
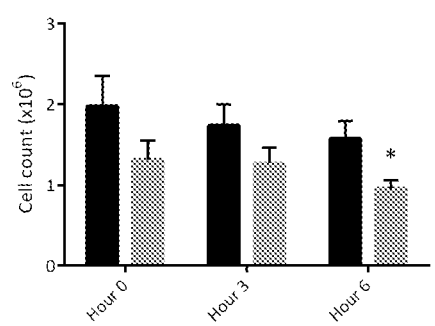

After isolation, TLF and peripheral blood neutrophils were stained with anti-human monoclonal antibodies (each cross-reactive with pigs; eBioscience, San Diego, Calif., USA) for CD16 (clone B73.1) and CD18 (clone TS1/18) for neutrophil population and activity identification, and also CD11a (clone HI111), CD11b (clone ICRF44), CD54 (clone HA58), and CD62L (clone DREG-56) as adhesion and activity markers. These neutrophils were then subsequently characterized by fluorescence activated cell sorting (FACS; FACScan DxP10, BD Biosciences, San Jose, Calif., USA). Respiratory burst was analyzed by priming CD16/CD18-stained neutrophils with 1 μM phorbol 12-myristate 13-acetate (PMA) for 10 minutes at 37° C. followed by addition of 1 μM dihydrorhodamine 123 (DHR-123) for 10 seconds and characterized by FACS. Twenty thousand events were analyzed with the FLOWJO® X software (Tree Star, Ashland, Oreg., USA) and compared for differences via Mann-Whitney U test. Neutrophils were counted via Trypan Blue exclusion and compared using student's t test. FIGS. 20A-20F are graphs depicting staining of porcine neutrophils isolated from tracheal lavage fluid for DHR-123 (FIG. 21A), CD11a (FIG. 21B), CD11b (FIG. 21C), CD54 (FIG. 21D), CD62L (FIG. 21E), and cell count (FIG. 21F). *p<0.05, p<0.01, *p<0.001.

Figure 22A:
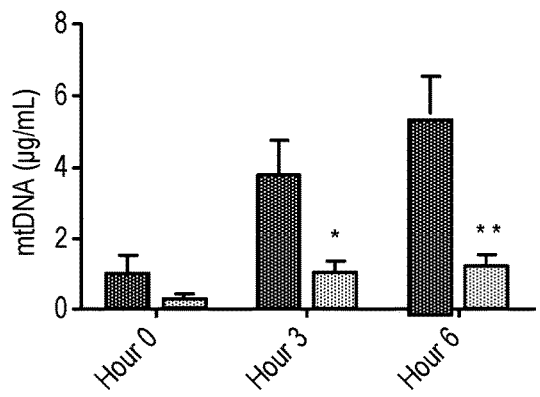
FIGS. 22A-22H are graphs depicting quantitative PCR (qPCR) of mRNAs from porcine neutrophils isolated from tracheal lavage fluid from animals with untreated and N-acetylcysteine/chloroquine-treated endotracheal tubes. The qPCR analysis determined levels for mtDNA (FIG. 22A), TLR-9 (FIG. 22B), IL1β (FIG. 22C), IL6 (FIG. 22D), IL8 (FIG. 22E), TNF-α (FIG. 22), IL10 (FIG. 22G) and bacterial 16S rDNA (FIG. 22H). $*p<0.05$, $p<0.01$, $*p<0.001$.
Figure 22B:
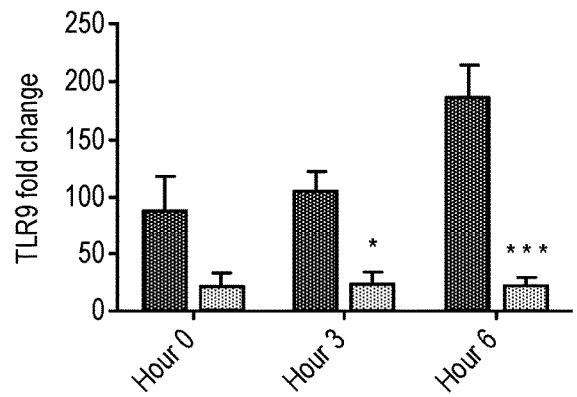
Figure 22C:
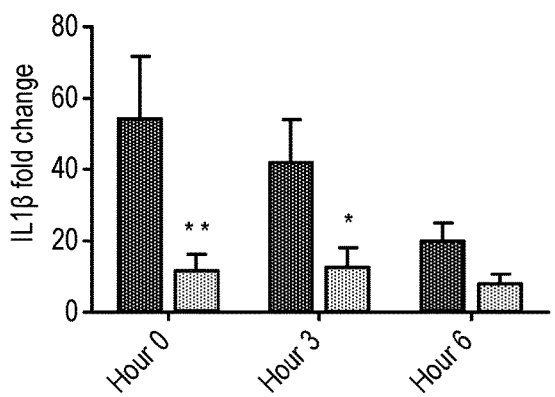
Figure 22D:
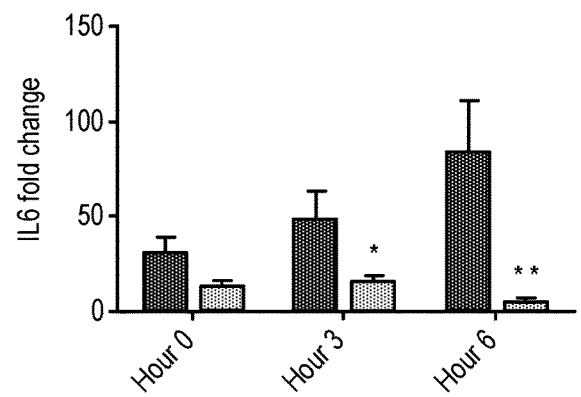
Figure 22E:
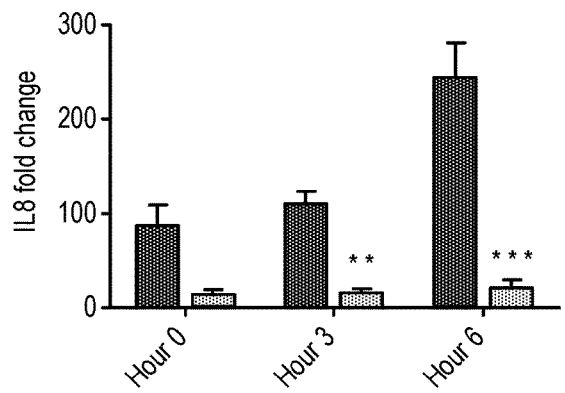
Figure 22F:
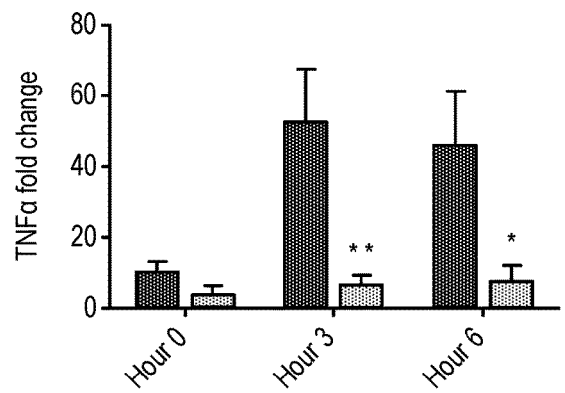
Figure 22G:
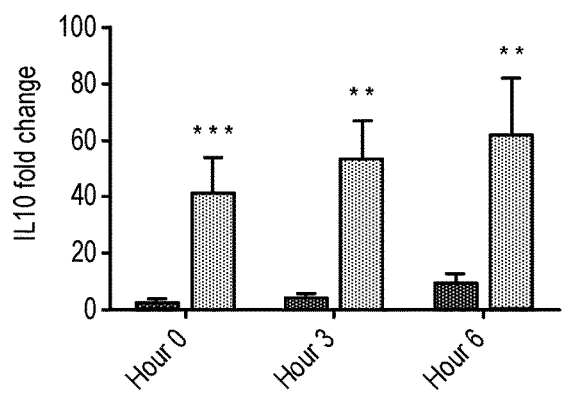
Figure 22H:
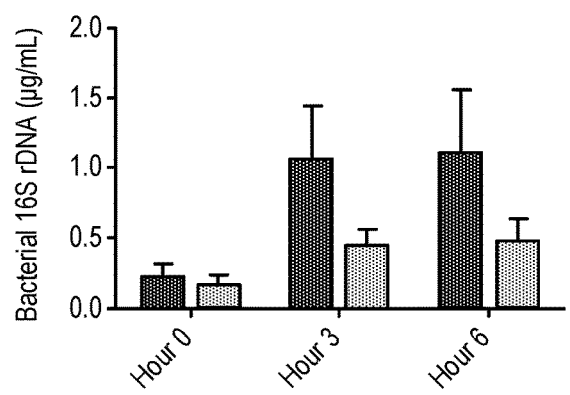

Primers for pig MT-CYB (Bio-Rad Laboratories Inc, Hercules, Calif., USA) and bacterial 16S rDNA (Integrated DNA Technologies, Coralville, Iowa, USA) were used to identify extracellular mtDNA (FIG. 22A) and bacterial DNA (FIG. 22H) concentrations in TLF samples (~10 mL) from pigs with untreated and N-acetylcysteine/chloroquine-treated endotracheal tubes, respectively. Neutrophil mRNA from both groups was isolated via TRIzol extraction and reverse transcribed into cDNA. Primers for pig IL1β, IL6, IL8, IL10, TNF-α, and TLR-9 (ThermoFisher Scientific, Waltham, Mass., USA) were used to evaluate transcription of these markers in neutrophils from both groups (FIGS. 22B-22G). Purified pig mtDNA (Bio-Rad Laboratories Inc., Hercules, Calif., USA) and unstimulated healthy pig peripheral blood neutrophils were used to quantify extracellular mtDNA concentration and fold change in inflammatory marker transcription, respectively. Purified *Escherichia coli* DNA (Invivogen, San Diego, Calif., USA) was used to quantify bacterial contamination via free bacterial DNA concentration. All experiments were run on a Bio-Rad CFX 96 thermocycler and analyzed with the provided Bio-Rad CFX Manager software. Results were compared for differences using a Kruskal-Wallis test, and Dunn's post hoc test. *p<0.05, p<0.01, *p<0.001.

Figures 23A, 23B, 23C, 23D:
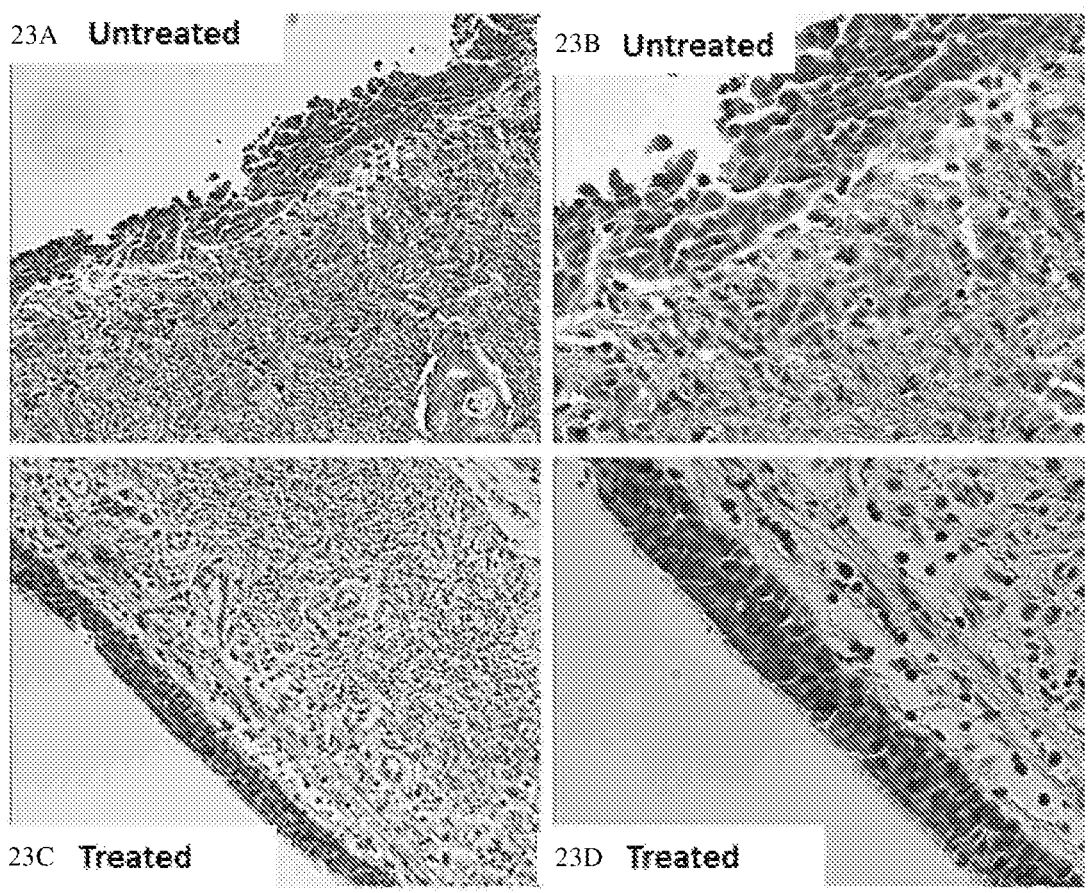
FIGS. 23A-23D are microscopic images of porcine trachea at point of contact with untreated (FIGS. 23A at 10× & 23B at 20×) and treated (FIGS. 23C at 10× & 23D at 20×) endo-tracheal tubes.
Figures 24A, 24B, 24C, 24D:
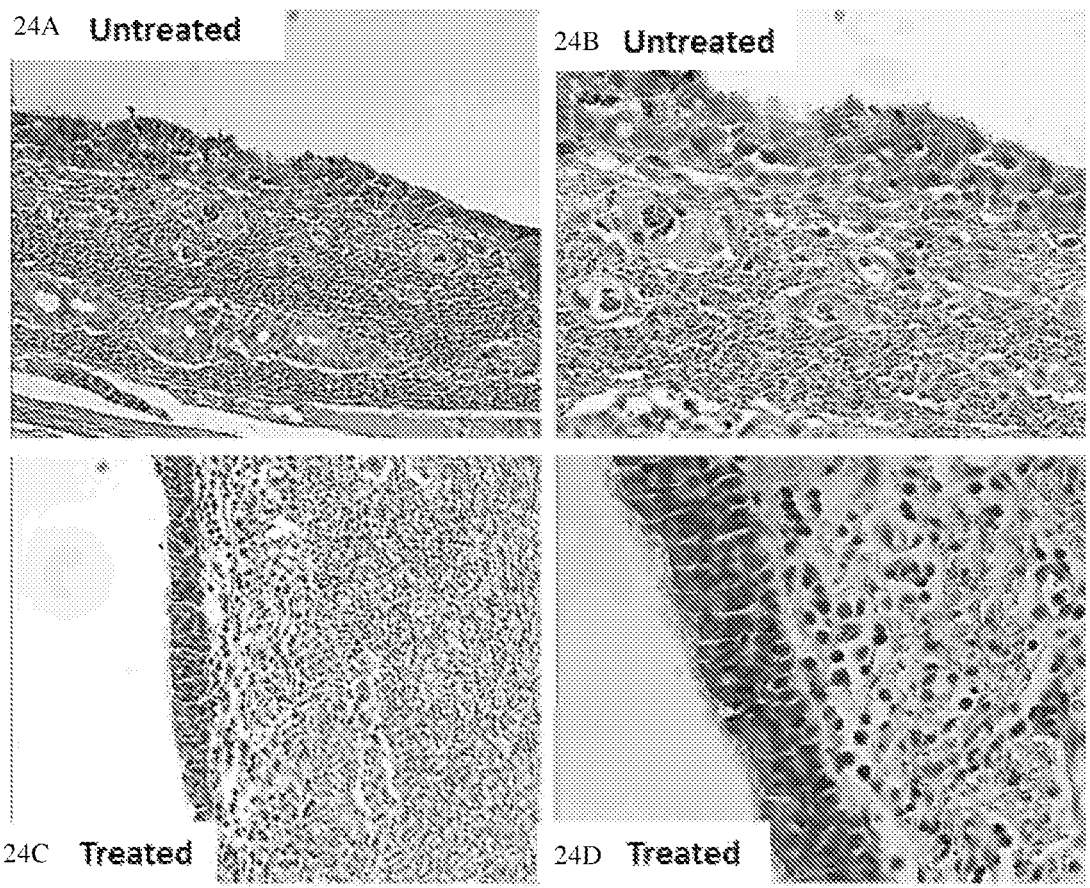
FIGS. 24A-24D are microscopic images of porcine trachea below the point of contact with untreated (FIG. 24A at 10× & 24B at 20×) and treated (FIGS. 24C at 10× & 24D at 20×) endo-tracheal tubes.
Figures 25A, 25B, 25C, 25D, 25E, 25F, 25G, 25H:
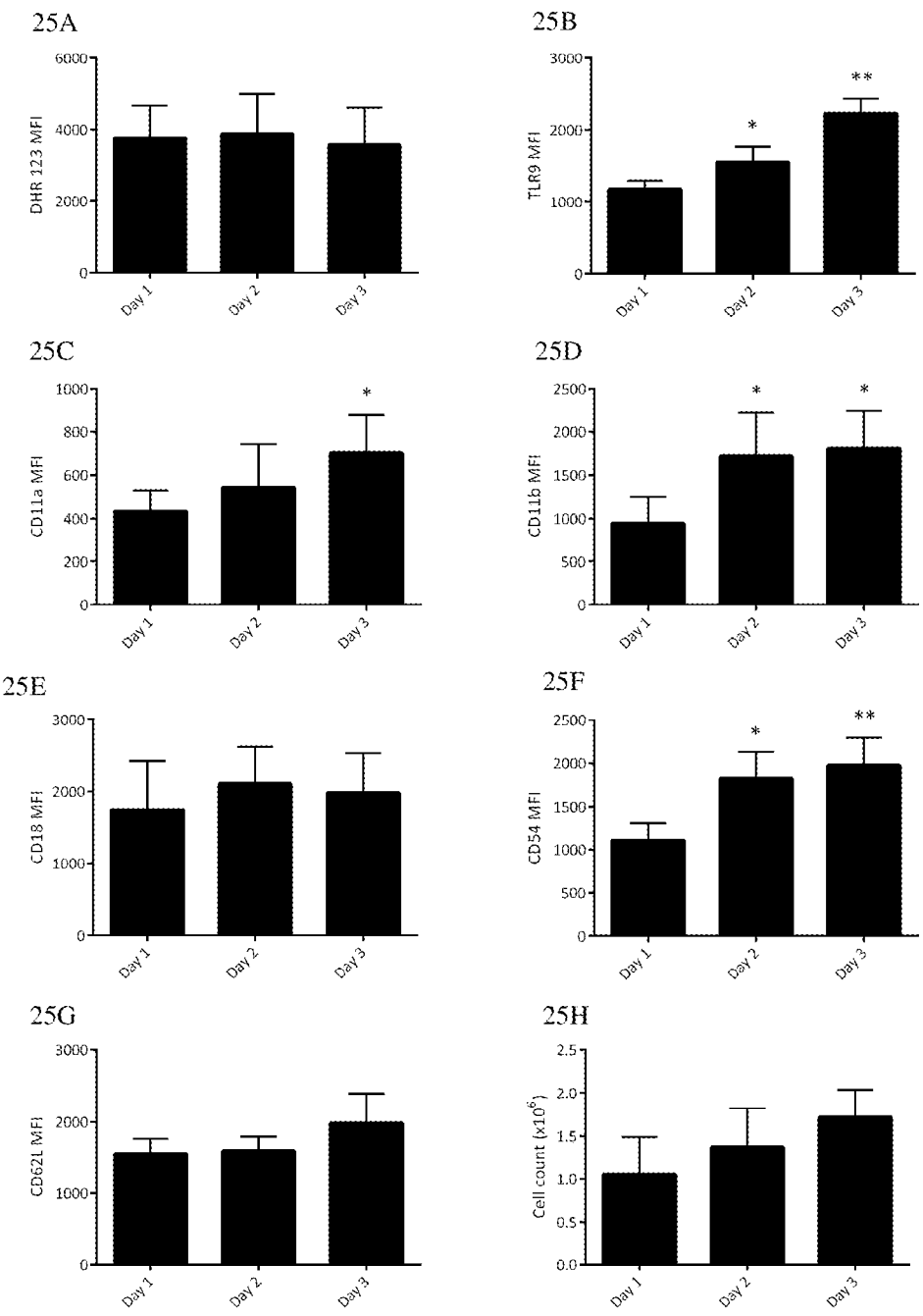
FIGS. 25A-25H are graphs depicting DHR-123 (FIG. 25A), TLR-9 (FIG. 25B), CD11A (FIG. 25C), CD11b (FIG. 25D), CD18 (FIG. 25E), CD54 (FIG. 25F), CD62L (FIG. 25G), and cell count (FIG. 25H) in human urine. $*p<0.05$, $**p<0.01$.

After 6 hours, untreated and N-acetylcysteine/chloroquine-treated endotracheal tubes were carefully removed and pigs were sacrificed. The tracheae were excised and biopsies of the trachea at point of contact with the endotracheal tubes (FIG. 23), and of the trachea below the endotracheal tube (FIG. 24) were taken and fixed in 10% formalin for approximately 72 hours. The biopsy samples were then dehydrated in 70% ethanol, paraffin-embedded, and then stained with hematoxylin and eosin for histopathological examination under light microscopy.

Example 8

In this Example, human neutrophils were analyzed from Foley catheters in human urethrae/bladders.

After placement of untreated size 14 Fr/Ch Foley catheters in human urethrae/bladders, approximately 20 mL urine was collected and centrifuged at 1370 rpm for 7 minutes to separate cells from unwanted extracellular material. Urine supernatants were then aliquoted and frozen at −20° C. The resulting cell pellets were then resuspended in 5 mL PBS +2% FBS and incubated at room temperature for 5 minutes. The cells were then incubated for 30 minutes at room temperature with HETASEP™ (Stem Cell Technologies, Vancouver, BC, CA) at a 5:1 urine cells:HETASEP™ ratio. After this incubation, the upper cell layer was transferred to a new 15 mL conical tube and centrifuged again at 1370 rpm for 7 minutes. The cells were then resuspended at $1 \times 10^5$ cells/mL in 2 mL PBS +2% FBS for neutrophil isolation via negative selection with EASYSEP™ Neutrophil Enrichment Kits (Stem Cell Technologies) per manufacturer's instructions. Neutrophils were then prepared for downstream applications (i.e., FACS, qPCR, functional assays). This was done for three days.

After isolation, urine and peripheral blood neutrophils were stained with anti-human monoclonal antibodies (eBioscience, San Diego, Calif., USA) for CD16 (clone B73.1) and CD66b (clone G10F5) for neutrophil population and activity identification, and also CD11a (clone HI111), CD11b (clone ICRF44), CD18 (clone TS1/18) CD54 (clone HA58), and CD62L (clone DREG-56) as adhesion and activity markers. These neutrophils were then subsequently characterized by fluorescence activated cell sorting (FACS; FACScan DxP10, BD Biosciences, San Jose, Calif., USA). Respiratory burst was analyzed by priming CD16/CD66b-stained neutrophils with 1 µM phorbol 12-myristate 13-acetate (PMA) for 10 minutes at 37° C. followed by addition of 1 µM dihydrorhodamine 123 (DHR-123) for 10 seconds and characterized by FACS. Twenty thousand events were analyzed with the FLOWJO® X software (Tree Star, Ashland, Oreg., USA) and compared for differences via Mann-Whitney U test. Urine-derived neutrophils were counted via Trypan Blue exclusion and compared using student's t test. FIGS. 25A-25H are graphs depicting DHR-123 (FIG. 25A), TLR-9 (FIG. 25B), CD11A (FIG. 25C), CD11b (FIG. 25D), CD18 (FIG. 25E), CD54 (FIG. 25F), CD62L (FIG. 25G), and cell count (FIG. 25H). *$p<0.05$, **$p<0.01$.

Figure 26A:
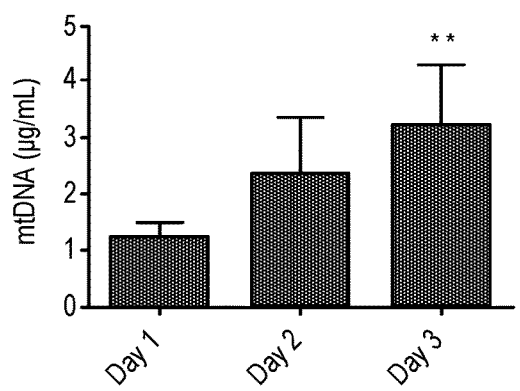
FIGS. 26A-26H are graphs depicting quantitative PCR (qPCR) of mtDNA (FIG. 26A), human TLR-9 (FIG. 26B), IL1β (FIG. 26C), IL6 (FIG. 26D), IL8 (FIG. 26E), TNF-α (FIG. 26F), IL10 (FIG. 26G) mRNA and bacterial 16S rDNA (FIG. 26H). RNA purified from neutrophils isolated from human urine whereas mtDNA and bacterial 16S rDNA were measured from human urine.
Figure 26B:
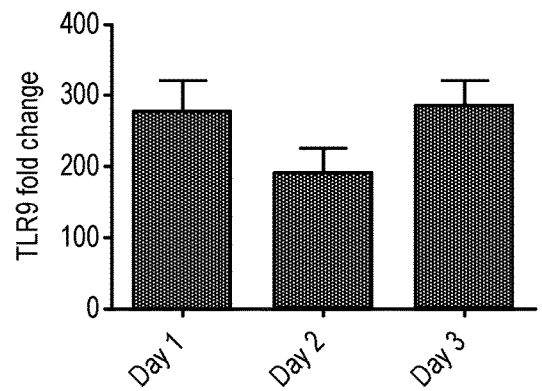
Figure 26C:
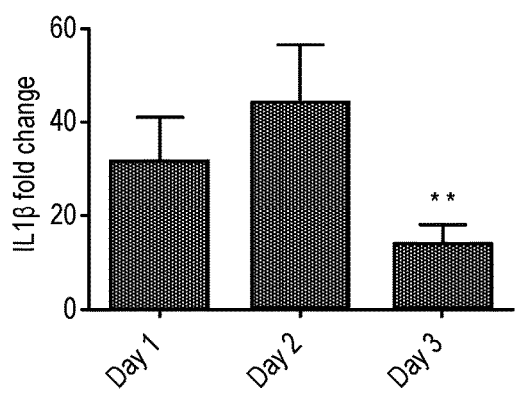
Figure 26D:
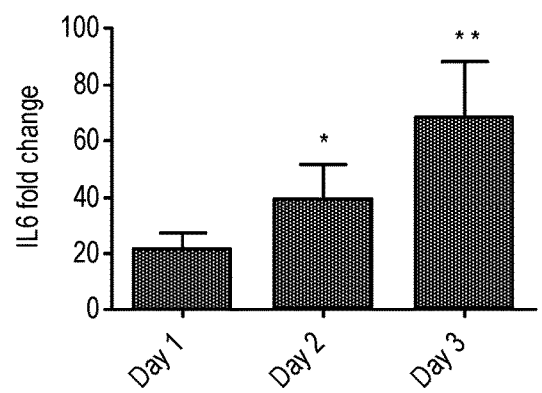
Figure 26E:
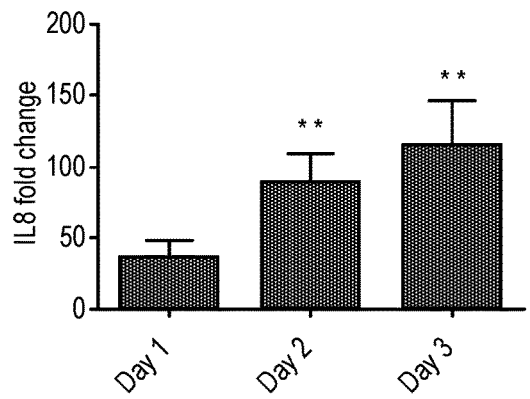
Figure 26F:
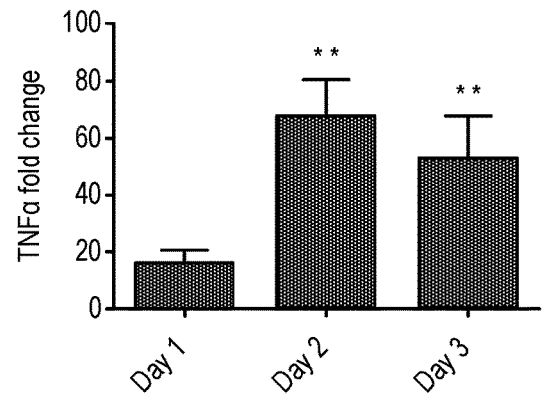
Figure 26G:
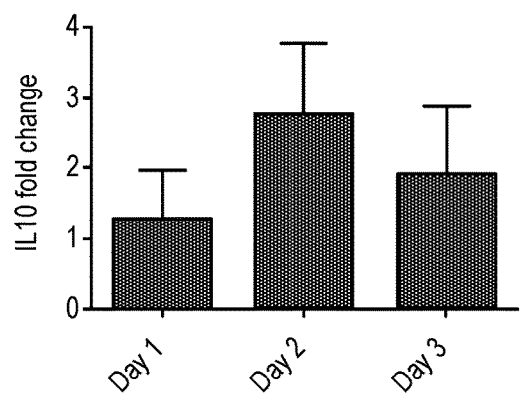
Figure 26H:
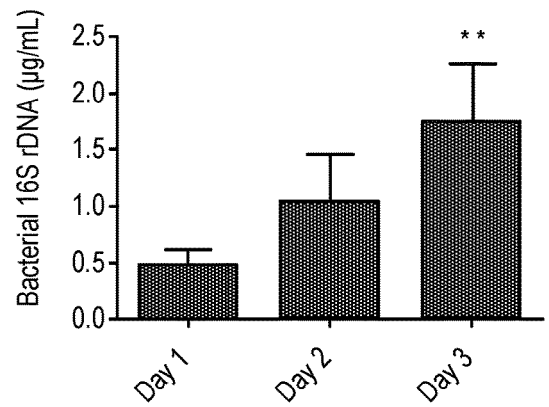

Primers for human MT-CYB (Bio-Rad Laboratories Inc, Hercules, Calif., USA) and bacterial 16S rDNA (Integrated DNA Technologies, Coralville, Iowa, USA) were used to identify extracellular mtDNA (FIG. 26A) and bacterial DNA (FIG. 26H) concentrations in urine samples (~20 mL) from humans with untreated Foley catheters. Neutrophil mRNA was isolated from the urine via TRIzol® extraction and reverse transcribed into cDNA. Primers for human TLR-9 (FIG. 26B), IL1β (FIG. 26C), IL6 (FIG. 26D), IL8 (FIG. 26E), TNF-α (FIG. 26F), and IL10 (FIG. 26G) (ThermoFisher Scientific, Waltham, Mass., USA) were used to evaluate transcription of these markers in neutrophils (B-G). Purified human mtDNA from an A549 cell line and unstimulated healthy human peripheral blood neutrophils were used to quantify extracellular mtDNA concentration and fold change in inflammatory marker transcription, respectively. Purified *Escherichia coli* DNA (Invivogen, San Diego, Calif., USA) was used to quantify bacterial contamination via free bacterial DNA concentration. All experiments were run on a Bio-Rad CFX 96 thermocycler and analyzed with the provided Bio-Rad CFX Manager software. Results were compared for differences using a Kruskal-Wallis test, and Dunn's post hoc test. *$p<0.05$, **$p<0.01$.

Figure 27:
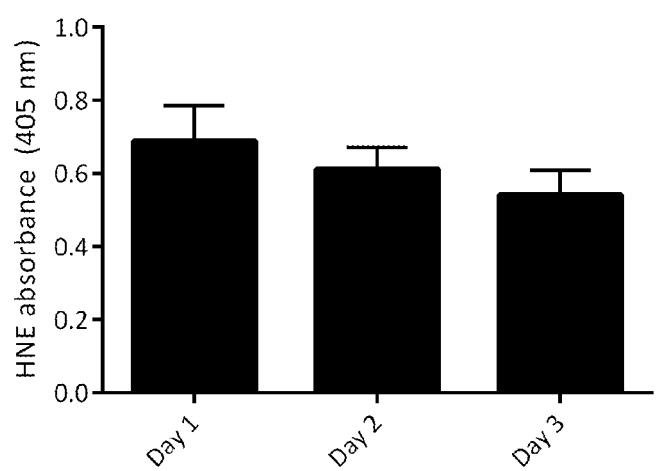
FIG. 27 is a graph depicting human neutrophil elastase (HNE) activity in human urine.
Figures 28A, 28B, 28C, 28D, 28E, 28F:
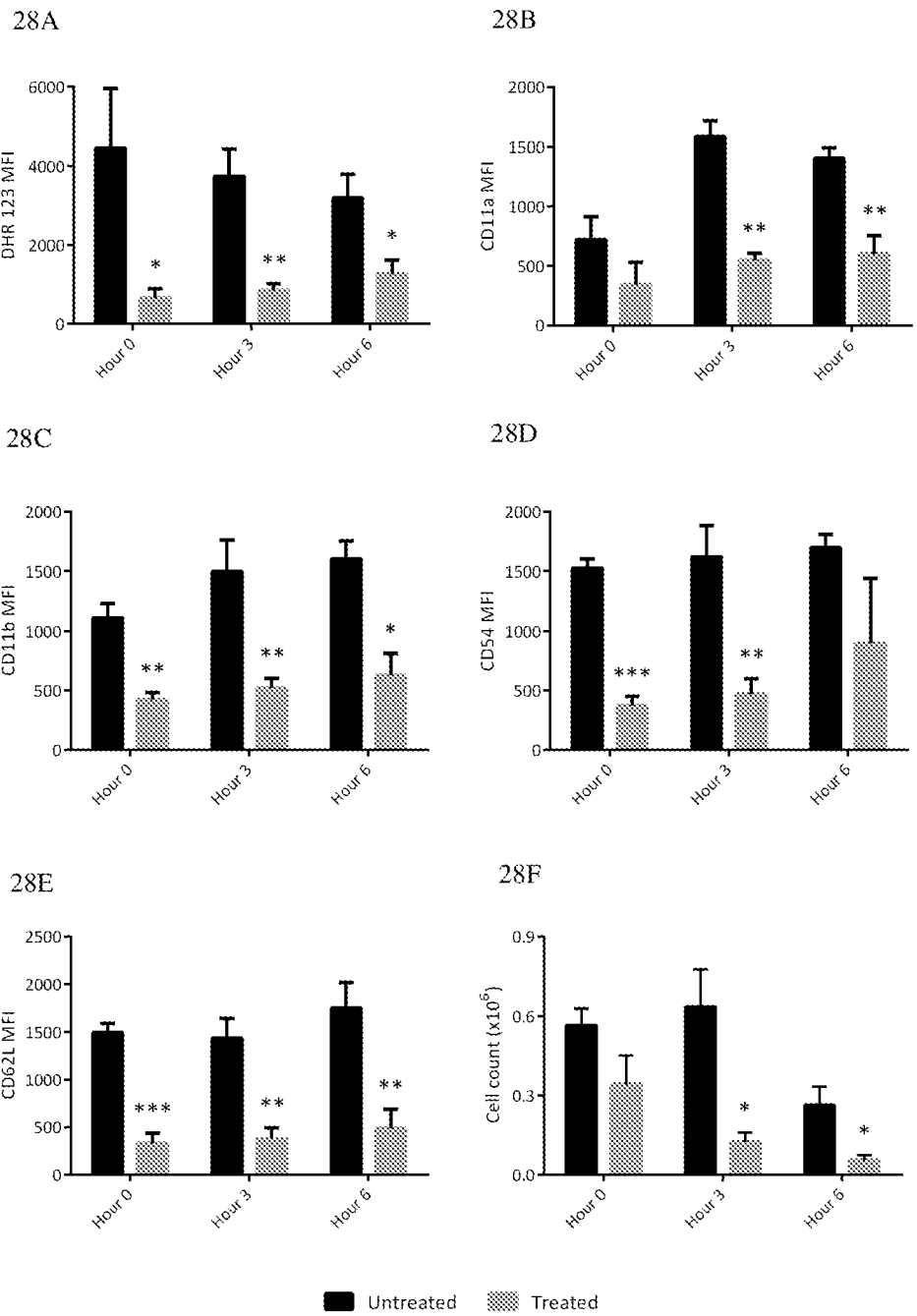
FIGS. 28A-28F are graphs depicting porcine neutrophils isolated from urine and analyzed by FACS for DHR-123 (FIG. 28A), CD11a (FIG. 28B), CD11b (FIG. 28C), CD54 (FIG. 28D), CD62L (FIG. 28E), and cell count (FIG. 28F). $*p<0.05$, $p<0.01$, $*p<0.001$.

Human neutrophil elastase (HNE) activity was then measured by the enzymatic hydrolysis of the HNE-specific chromogenic substrate N-methoxysuccinyl-Ala-Ala-Pro-Val p-nitroanilide (MeO-SucAAPVpNA; Sigma Aldrich, St. Louis, Mo., USA) into 4-nitroaniline. 100 µL of the urine supernatants were incubated with 200 µL 1 mM MeO-SucAAPVpNA in 0.1 M HEPES (pH 7.5) buffer at 37° C.+5% $CO_2$ for one hour. After incubation, substrate cleavage into 4-nitroaniline by HNE in the supernatants was measured by absorbance at 405 nm via spectrophotometry (NanoDrop 2000, ThermoFisher Scientific, Waltham, Mass., USA) (FIG. 27).

Example 9

In this Example, porcine neutrophils were analyzed from Foley catheters in porcine urethrae/bladders.

After placement of untreated and N-acetylcysteine/chloroquine-treated size 10 Fr/Ch Foley catheters in pig urethrae/bladders, approximately 20 mL urine from both groups was collected and centrifuged at 1370 rpm for 7 minutes to separate cells from unwanted extracellular material. Urine supernatants were then aliquoted and frozen at −20° C. The resulting cell pellets were then resuspended in 5 mL PBS +2% FBS and incubated at room temperature for 5 minutes. The cells were then incubated for 30 minutes at room temperature with HETASEP™ (Stem Cell Technologies, Vancouver, BC, CA) at a 5:1 urine cells:HETASEP™ ratio. After this incubation, the upper cell layer was transferred to a new 15 mL conical tube and centrifuged again at 1370 rpm for 7 minutes. The cells were then resuspended at $1\times10^5$ cells/mL in 2 mL PBS +2% FBS for neutrophil isolation via negative selection with EASYSEP™ Neutrophil Enrichment Kits (Stem Cell Technologies) per manufacturer's instructions. Neutrophils were then prepared for downstream applications (i.e., FACS, qPCR, functional assays). This was executed at time points 0, 3, and 6 hours.

After isolation, urine and peripheral blood neutrophils were stained with anti-human monoclonal antibodies (each cross-reactive with pigs; eBioscience, San Diego, Calif., USA) for CD16 (clone B73.1) and CD18 (clone TS1/18) for neutrophil population and activity identification, and also CD11a (clone HI111), CD11b (clone ICRF44), CD54 (clone HA58), and CD62L (clone DREG-56) as adhesion and activity markers. These neutrophils were then subsequently characterized by fluorescence activated cell sorting (FACS; FACScan DxP10, BD Biosciences, San Jose, Calif., USA). Respiratory burst was analyzed by priming CD16/CD18-stained neutrophils with 1 µM phorbol 12-myristate 13-acetate (PMA) for 10 minutes at 37° C. followed by addition of 1 µM dihydrorhodamine 123 (DHR-123) for 10 seconds and characterized by FACS. Ten thousand events were analyzed with the FLOWJO® X software (Tree Star, Ashland, Oreg., USA) and compared for differences via Mann-Whitney U test. Neutrophils were counted via Trypan Blue exclusion and compared using student's t test. FIGS. 28A-28F are graphs depicting porcine neutrophils isolated from urine and stained for DHR-123 (FIG. 28A), CD11a (FIG. 28B), CD11b (FIG. 28C), CD54 (FIG. 28D), CD62L (FIG. 28E), and cell count (FIG. 28F). *$p<0.05$, $p<0.01$, *$p<0.001$.

Figure 29A:
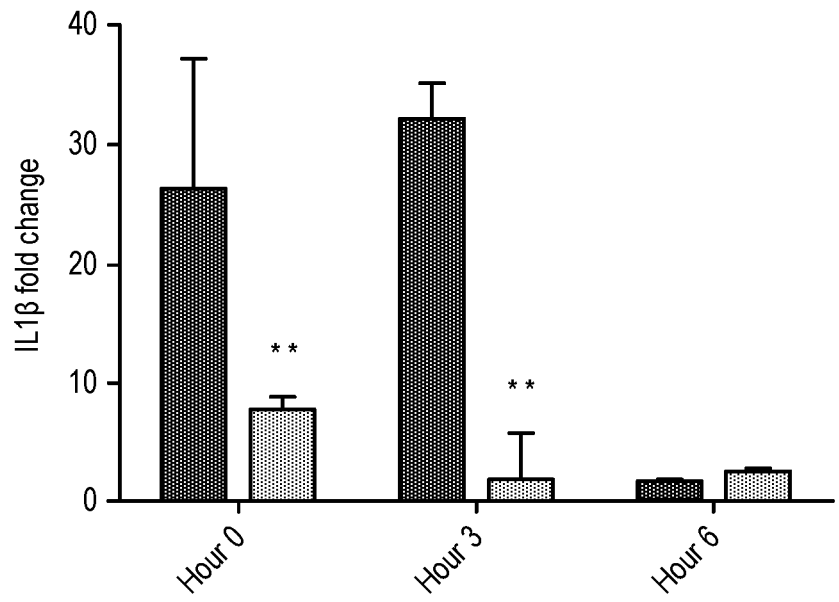
FIGS. 29A-29F are graphs depicting quantitative PCR (qPCR) analysis of porcine urine and neutrophils isolated from porcine urine showing gene expression levels of IL1β (FIG. 29A), IL6 (FIG. 29B), IL8 (FIG. 29C), IL10 (FIG. 29D), TNF-α (FIG. 29E), TLR-9 (FIG. 29F) mRNA from neutrophils and mtDNA (FIG. 29G) and bacterial 16S rDNA (FIG. 29H) from urine.$*p<0.05$, $p<0.01$, $*p<0.001$.
Figure 29B:
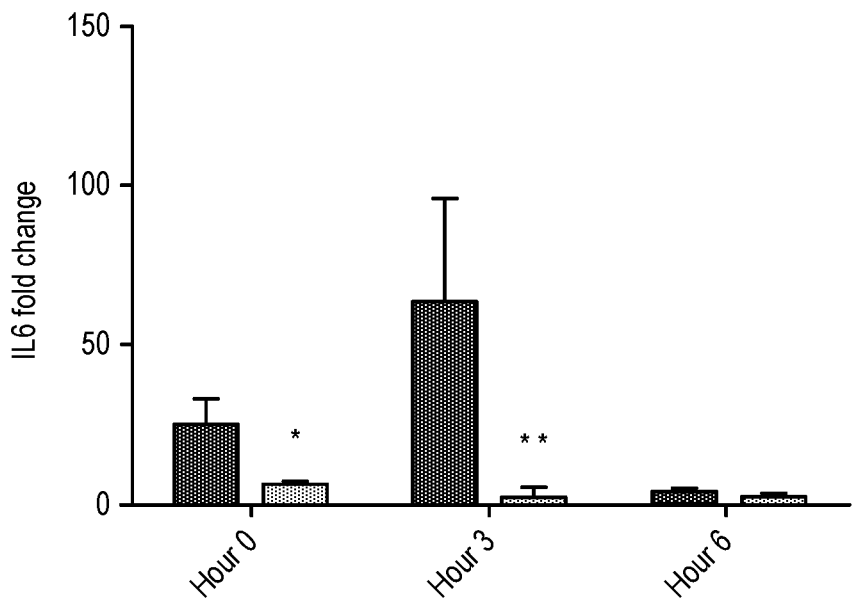
Figure 29C:
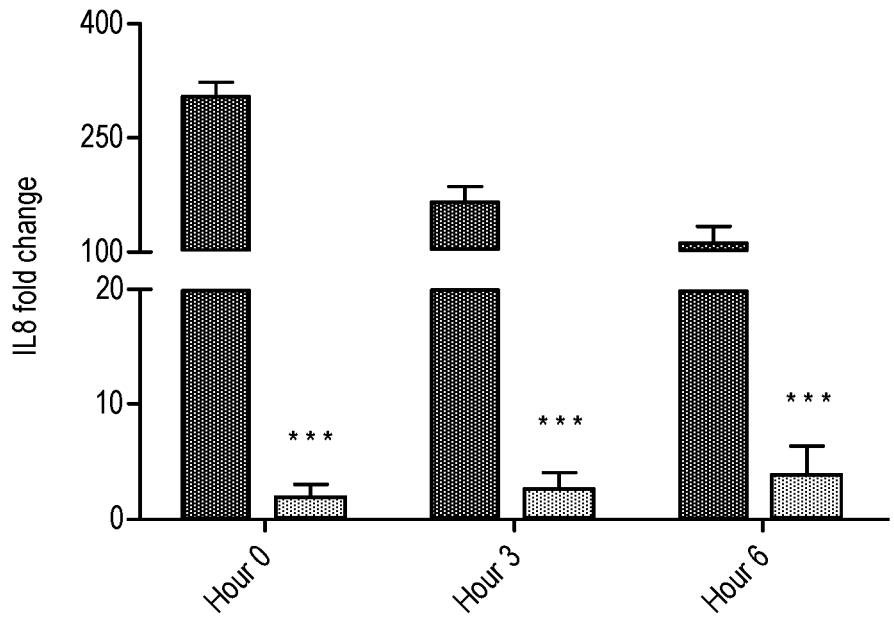
Figure 29D:
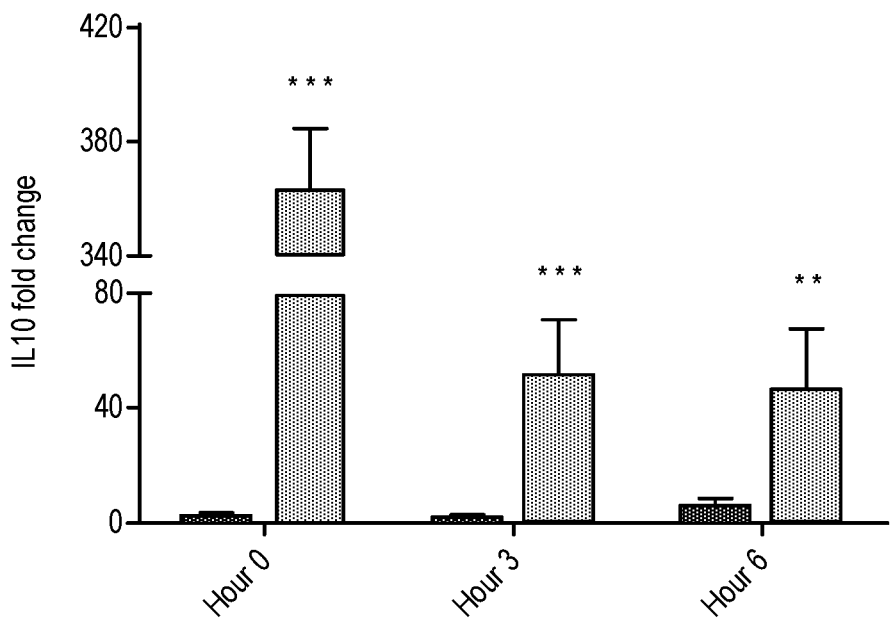
Figure 29E:
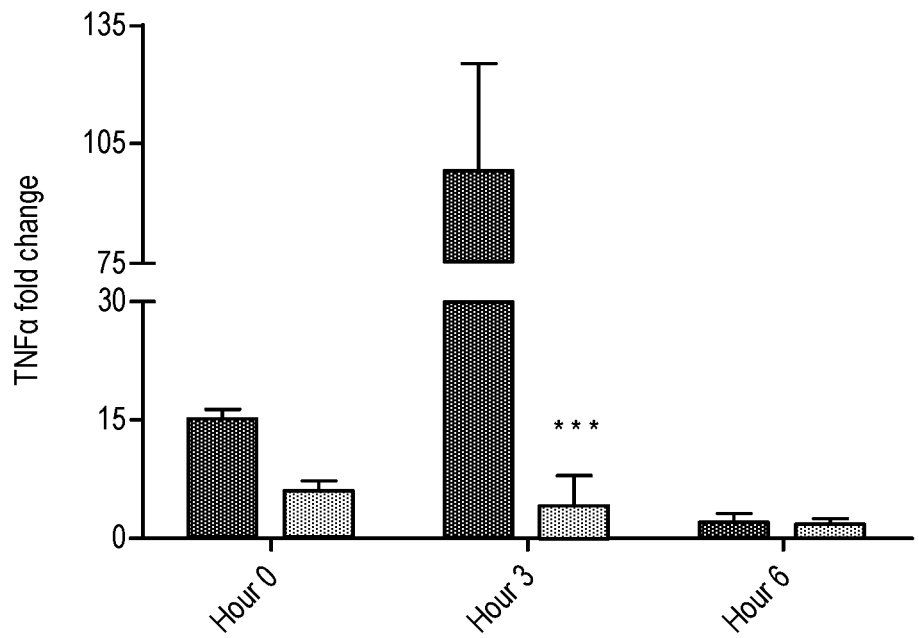
Figure 29F:
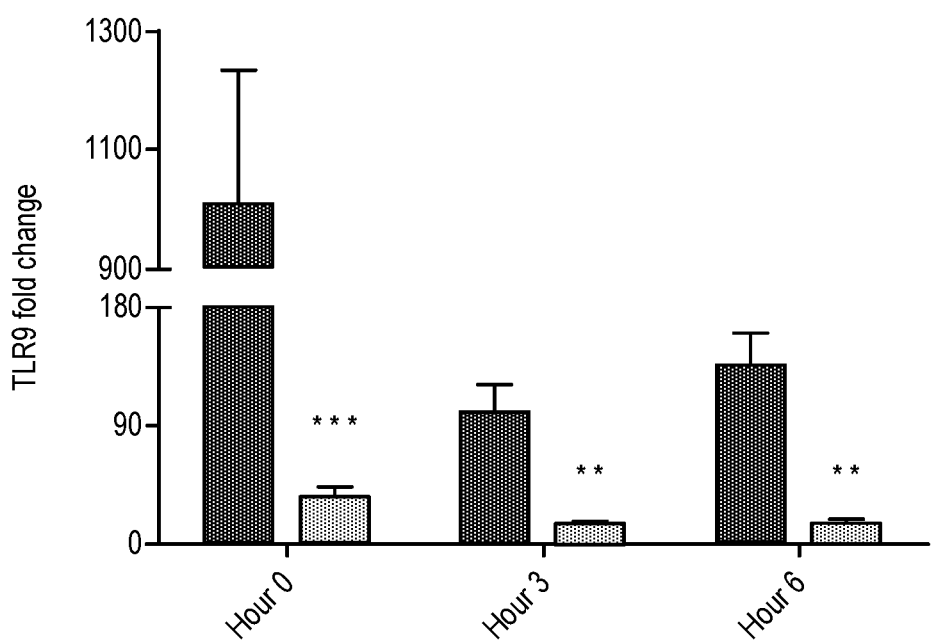
Figure 29G:
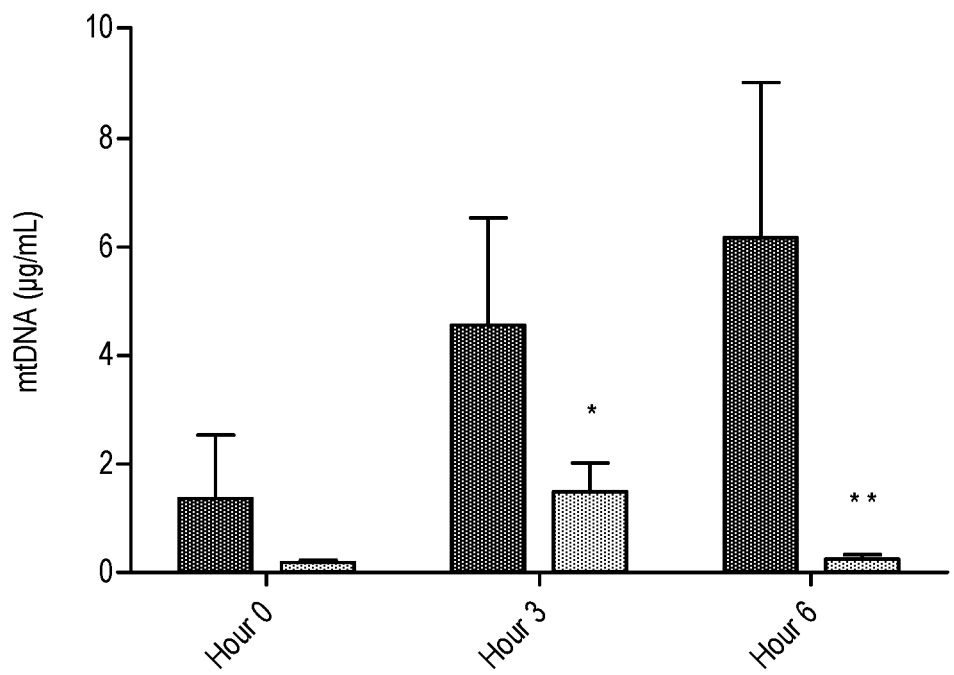
Figure 29H:
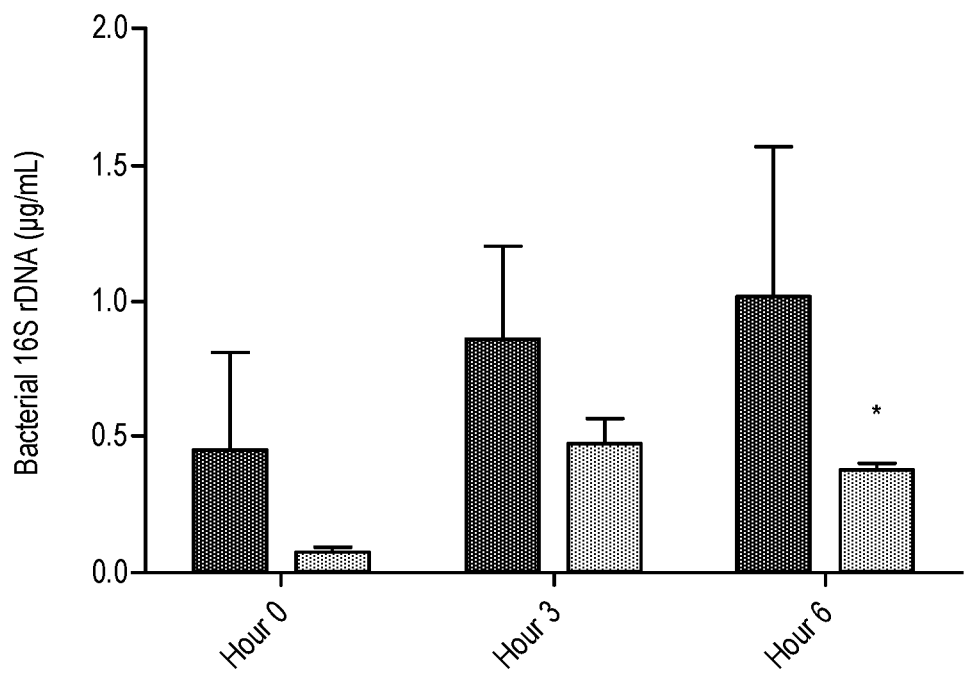
Figure 31A:
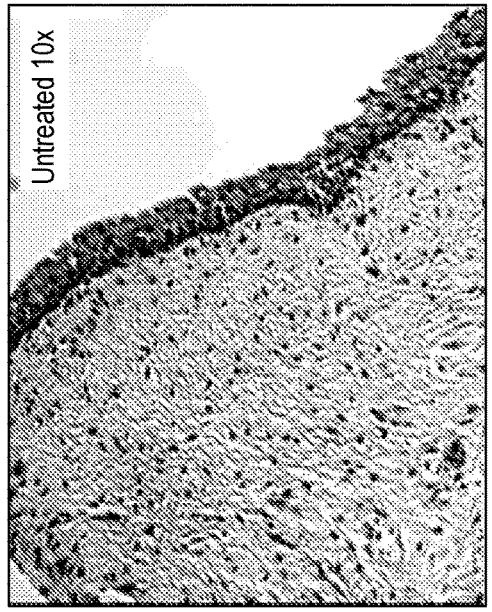
FIGS. 31A-31D are of the lower half of the bladder in animals with untreated Foley catheters (FIGS. 31A & 31B) and treated Foley catheters (FIGS. 31C & 31D).
Figure 31B:
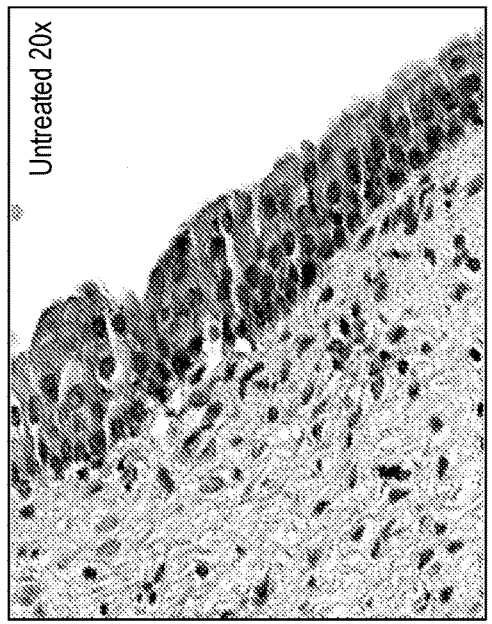
Figure 31C:
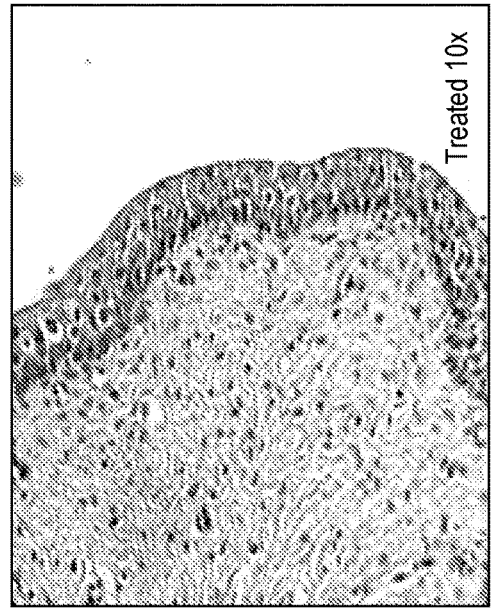
Figure 31D:
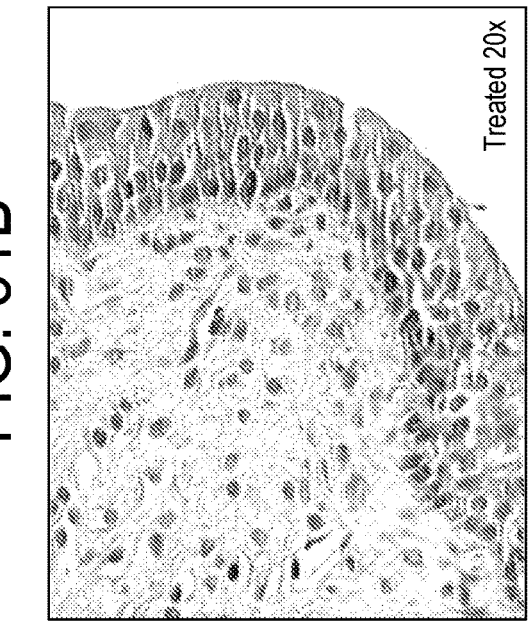

Primers for pig MT-CYB (Bio-Rad Laboratories Inc, Hercules, Calif., USA) and bacterial 16S rDNA (Integrated DNA Technologies, Coralville, Iowa, USA) were used to identify extracellular mtDNA (FIG. 29G) and bacterial DNA (FIG. 29H) concentrations in urine samples (~20 mL) from pigs with untreated and N-acetylcysteine/chloroquine-treated Foley catheters, respectively. Neutrophil mRNA from both groups was isolated via TRIzol extraction and reverse transcribed into cDNA. Primers for pig IL1β (FIG. 29A), IL6 (FIG. 29B), IL8 (FIG. 29C), IL10 (FIG. 29D), TNF-α (FIG. 29E), and TLR-9 (FIG. 29F) (ThermoFisher Scientific, Waltham, Mass., USA) were used to evaluate transcription of these markers in neutrophils from both groups. Purified pig mtDNA (Bio-Rad Laboratories Inc, Hercules, Calif., USA) and unstimulated healthy pig peripheral blood neutrophils were used to quantify extracellular mtDNA concentration and fold change in inflammatory marker transcription, respectively. Purified *Escherichia coli* DNA (Invivogen, San Diego, Calif., USA) was used to quantify bacterial contamination via free bacterial DNA concentration. All experiments were run on a Bio-Rad CFX 96 thermocycler and analyzed with the provided Bio-Rad CFX Manager software. Results were compared for differences using a Kruskal-Wallis test, and Dunn's post hoc test. FIGS. 29A-29H are graphs depicting quantitative PCR (qPCR) analysis of porcine urine and urine-derived neutrophils. FIGS. 29A-29F show gene expression levels of several transcripts from neutrophil RNA and FIGS. 29G & 29H show mtDNA and bacterial DNA levels in urine.*p<0.05, p<0.01, *p<0.001.

After 6 hours, untreated and N-acetylcysteine/chloroquine-treated Foley catheters were carefully removed and pigs were sacrificed. The bladders and connected urethrae were excised and biopsies of the urethra at point of contact with the Foley catheters (FIGS. 30A-30D), of the lower half of the bladder (FIGS. 31A-31D), and the upper half of the bladder (FIGS. 32A-32D) were taken and fixed in 10% formalin for approximately 72 hours. The biopsy samples were then dehydrated in 70% ethanol, paraffin-embedded, and then stained with hematoxylin and eosin for histopathological examination under light microscopy.

Example 10

In this Example, human neutrophils were analyzed for neutrophil extracellular trap (NET) activity.

Approximately 10 mL peripheral blood from healthy volunteers was collected and incubated for 30 minutes at room temperature with HETASEP™ (Stem Cell Technologies, Vancouver, BC, CA) at a 5:1 blood:HETASEP™ ratio. After this incubation, the upper white blood cell layer was transferred to a new 15 mL conical tube, 10 mL PBS +2% FBS was added, and centrifuged again at 1370 rpm for 7 minutes. The cells were then resuspended at $1\times10^6$ cells/mL in 2 mL PBS +2% FBS for neutrophil isolation via negative selection with EASYSEP™ Neutrophil Enrichment Kits (Stem Cell Technologies) per manufacturer's instructions. Neutrophils were then resuspended at $1\times10^6$ cells/mL Human Neutrophil Media (RPMI-1640/-$Ca^{2+}$ $Mg^{2+}$/+10% FBS/+2 mM EDTA/+1 μg L-glutamine) and prepared for downstream applications.

Approximately $1\times10^5$ neutrophils isolated from healthy volunteer peripheral blood were seeded on 12 mm 0.001% polylysine glass cover slips in 12-well-plates supplemented with 0.5 mL Human Neutrophil Media and incubated at 37° C.+5% $CO_2$ for 30 minutes. Four (4) μg mtDNA was added to cover slips with approximately $1\times10^5$ adherent neutrophils (FIGS. 33A & 33B); and with (FIG. 33B) or without (FIG. 33A) N-acetylcysteine/chloroquine and then incubated at 37° C.+5% $CO_2$ for 4 hours to allow for neutrophil extracellular trap (NET) activity. After incubation, 0.5 mL 4% paraformaldehyde was added to the wells and cooled at 4° C. for 18 hours. Afterwards, 0.5 mL PBS was added to each well and subsequently stained with 0.3 mL goat anti-mouse neutrophil elastase primary antibody (cross-reactive with humans; ThermoFisher Scientific, Waltham, Mass., USA) 1:400 dilution in MAXBLOCK™ (Active Motif, Carlsbad, Calif., USA) blocking reagent, and then stained with 0.3 mL donkey anti-goat ALEXAFLUOR® 488 (ThermoFisher Scientific) 1:400 dilution in MAXBLOCK™. After incubation at room temperature for one hour, one drop of NUCBLUE® Fixed Cell READYPROBES™ Reagent (Hoechst33342 dye [DAPI]; ThermoFisher Scientific) was added to each well and left at room temperature for 15 minutes, then mounted on slides with SLOWFADE™ Gold anti-fade reagent (ThermoFisher Scientific) for confocal microscopy.

Example 11

In this Example, human neutrophils were analyzed for neutrophil phagocytosis of gram positive and gram negative activity.

Fluorescein isothiocyanate (FITC) dye (0.01 mg) in 0.5 mL bicarbonate buffer was added to approximately $1.2\times10^7$ methicillin-sensitive *Staphylococcus aureus* (MSSA, gram-positive; FIG. 34) and *Escherichia coli* (gram-negative; FIG. 35) bacteria and incubated at 37° C.+5% $CO_2$ for one hour. Then, approximately $1\times10^5$ neutrophils isolated from healthy volunteer peripheral blood were seeded on 12 mm 0.001% polylysine glass cover slips in 12-well-plates supplemented with 0.5 mL Human Neutrophil Media and incubated at 37° C.+5% $CO_2$ for 30 minutes.

Figure 35A:
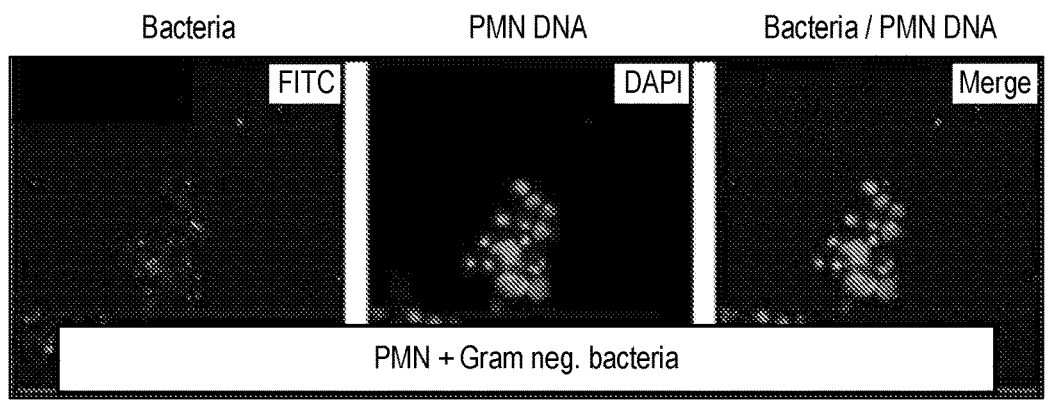
FIGS. 35A-35D are fluorescent micrographs depicting human PMNs (neutrophils) co-cultured with gram-negative bacteria. Human PMNs (neutrophils) engulfed gram-negative bacteria when co-cultured (FIG. 35A). When mtDNA was included, the PMNs failed to engulf (phagocytosis) the gram-negative bacteria (FIG. 35B). However, when both N-acetylcysteine/chloroquine and mtDNA were included (FIG. 35C), the PMNs were again able to respond normally to the gram-negative bacteria by engulfing them once again. When only N-acetylcysteine/chloroquine was included with the PMNs and the gram-negative bacteria (FIG. 35D), there was no effect, as the PMNs displayed a normal phagocytosis response to the gram-negative bacteria.
Figure 35B:
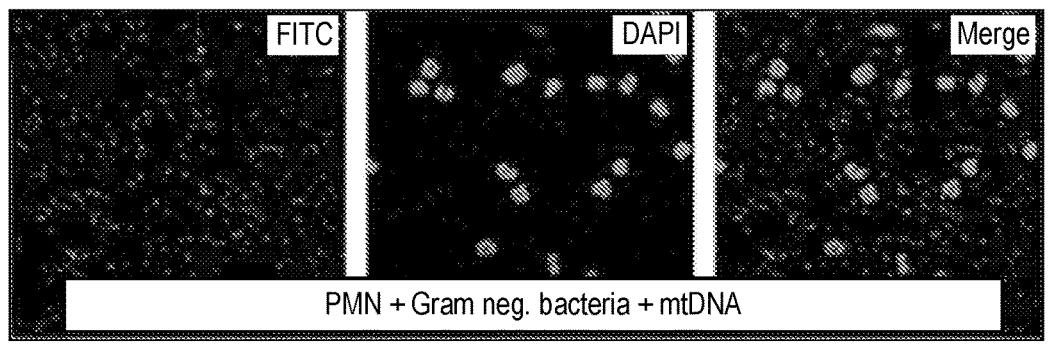
Figure 35C:
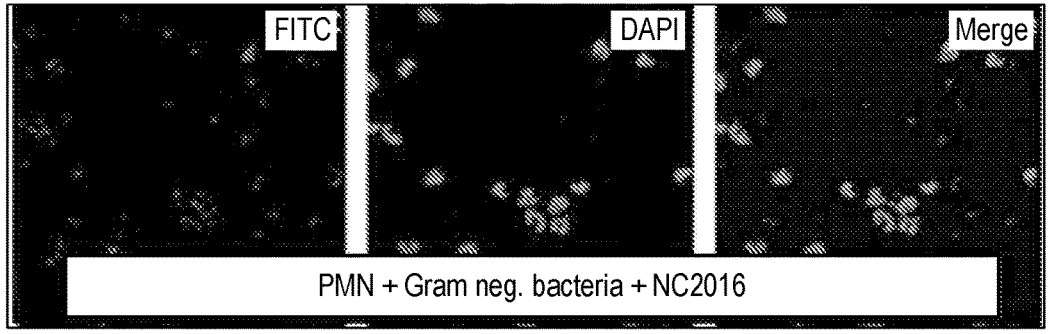
Figure 35D:
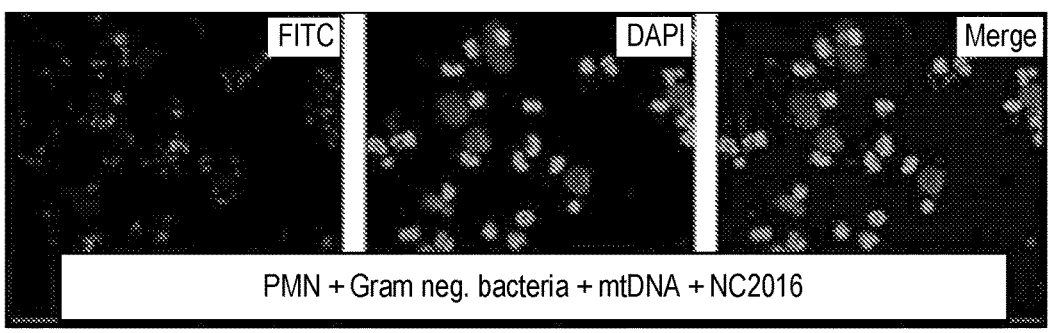

For co-treatments and co-incubations, 4 μg mtDNA was added to cover slips with approximately $1\times10^5$ adherent neutrophils and with N-acetylcysteine/chloroquine or without N-acetylcysteine/chloroquine. These were incubated at 37° C.+5% $CO_2$ for 4 hours to allow for neutrophil extracellular trap (NET) activity. Next, MSSA or *E. coli* was added to neutrophil-adherent cover slips at a ratio of $1\times10^6$ bacteria: $1\times10^5$ neutrophils with or without 4 μg mtDNA, and with or without N-acetylcysteine/chloroquine and incubated at 37° C.+5% $CO_2$ for 30 minutes to allow for phagocytic activity. After incubation 0.5 mL 4% paraformaldehyde was added to the wells and cooled at 4° C. for 18 hours to prepare for staining. Then, NUCBLUE® Fixed Cell READYPROBES™ Reagent (Hoechst33342 dye [DAPI]; ThermoFisher Scientific) was applied and left at room temperature for 15 minutes before mounting on slides with SLOWFADE™ Gold anti-fade reagent (ThermoFisher Scientific) for confocal microscopy. The human PMNs (neutrophils) engulfed gram-positive (FIG. 34A) and gram-negative (FIG. 35A) bacteria when co-cultured as expected. When mtDNA was included, the PMNs failed to engulf (phagocytosis) the gram-positive (FIG. 34B) and gram-negative bacteria (FIG. 35B). However, when both N-acetylcysteine/chloroquine and mtDNA were included (FIG. 34C and FIG. 35C), the PMNs were again able to respond normally to either type of bacteria by engulfing them once again. When only N-acetylcysteine/chloroquine was included with the PMNs and bacteria (FIG. 34D and FIG. 35D), there was no effect, as the PMNs displayed a normal phagocytosis response to both types of bacteria.

Figure 33:
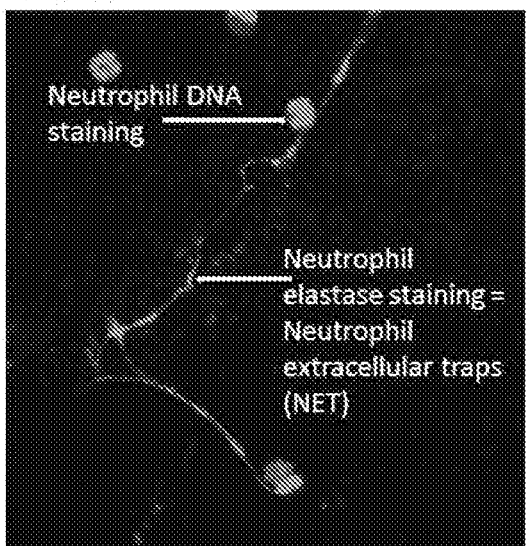
FIGS. 33A & 33B are fluorescent micrographs depicting neutrophil extracellular trap (NET) activity adherent neutrophils incubated with mtDNA and with (FIG. 33B) or without (FIG. 33A) N-acetylcysteine/chloroquine.
Figure 33:
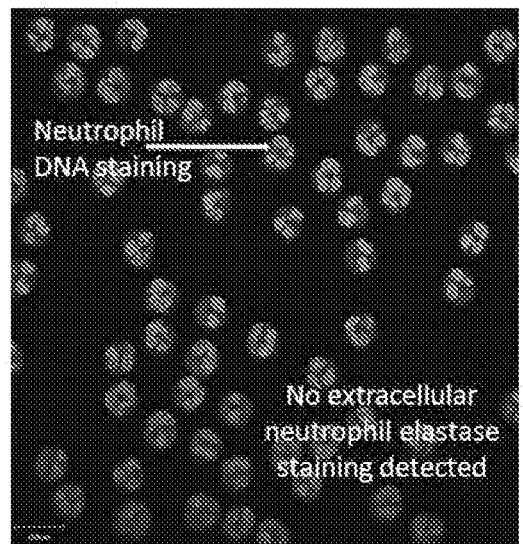
Figure 34A:
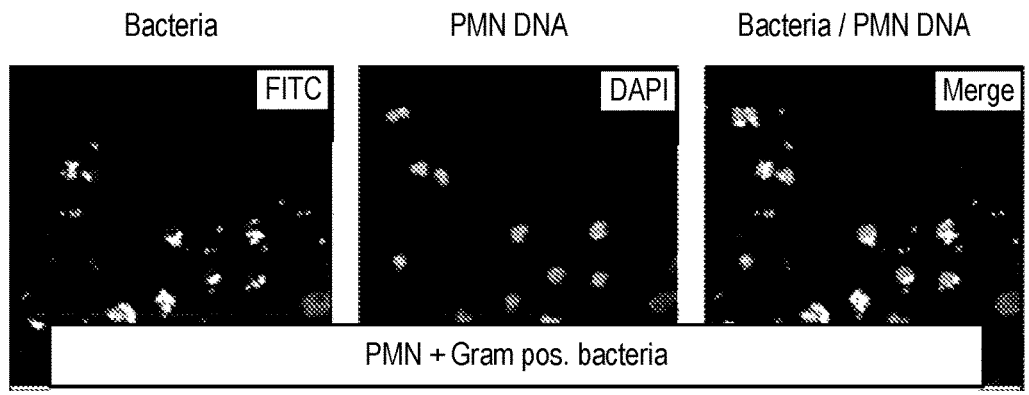
FIGS. 34A-34D are fluorescent micrographs depicting human PMNs (neutrophils) co-cultured with gram-positive bacteria. Human PMNs (neutrophils) engulfed gram-positive bacteria when co-cultured (FIG. 34A). When mtDNA was included, the PMNs failed to engulf (phagocytosis) the gram-positive bacteria (FIG. 34B). However, when both N-acetylcysteine/chloroquine and mtDNA were included (FIG. 34C), the PMNs were again able to respond normally to gram-positive bacteria by engulfing them once again. When only N-acetylcysteine/chloroquine was included with the PMNs and gram-positive bacteria (FIG. 34D), there was no effect, as the PMNs displayed a normal phagocytosis response to gram-positive bacteria.
Figure 34B:
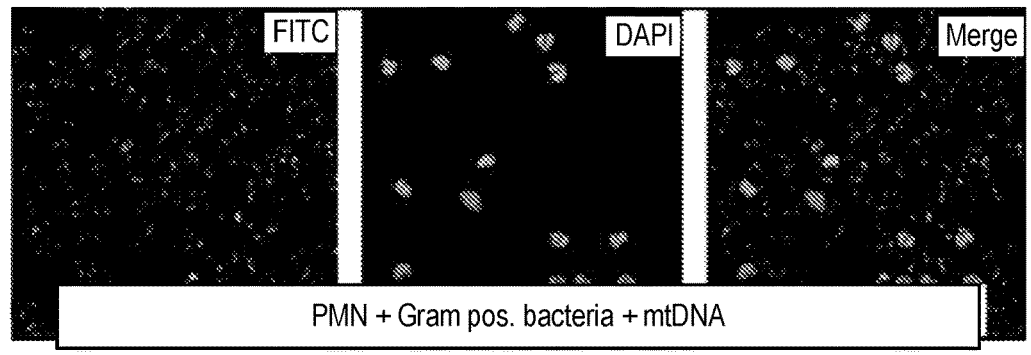
Figure 34C:
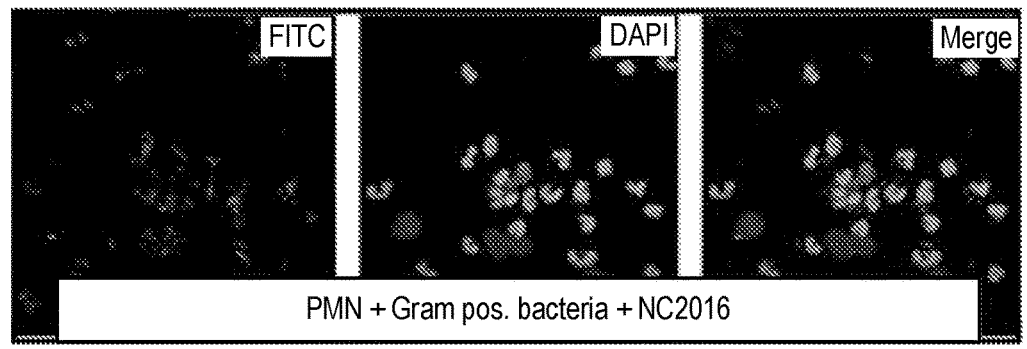
Figure 34D:
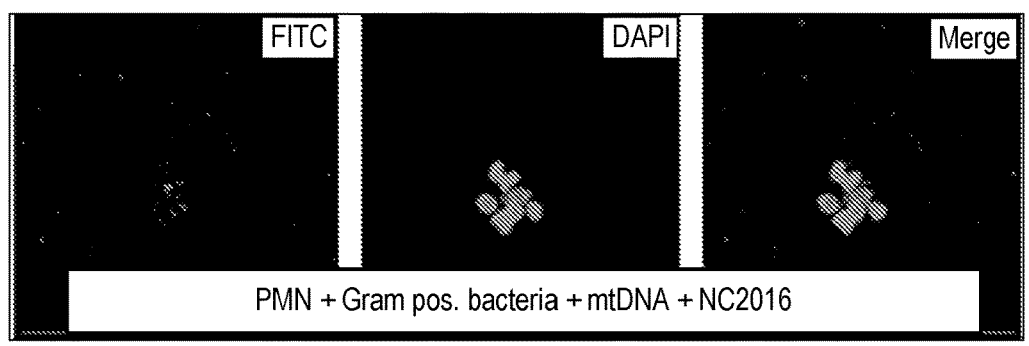

These results demonstrate that N-acetylcysteine/chloroquine selectively blocks mtDNA-induced activation of TLR-9 activation while sparing TLR2 activation in response to gram-positive bacteria (FIG. 33). These results also demonstrate that N-acetylcysteine/chloroquine selectively blocks mtDNA-induced activation of TLR-9 activation while sparing TLR4 activation in response to gram-negative bacteria (FIG. 34).

Example 12

In this Example, an exemplary method for coating medical device with the compositions of the disclosure is described.

Materials. Magnesium stearate powder (Sigma Aldrich, St. Louis, Mo.); polyvinylpyrrolidone (PVP) (Sigma Aldrich, St. Louis, Mo.); Chloroquine Diphosphate Salt (MP Biomedicals); Acetylcysteine Injection (6 g/30 mL) (Perrigo); ethyl alcohol (EtOH), 190 proof, USP grade (synthetically derived (Pharmo-Aaper).

Method. 20 g PVP and 0.5 g Mg stearate were separately measured and added to a 300 mL Erlenmeyer flask. 100 mL of 10% EtOH was added to the flask and stirred constantly for approximately 2 minutes. The flask and its contents to was heated to approximately 100° C. for 15-30 seconds, then heating was immediately stopped followed by constant stirring in room temperature for 10-15 minutes to allow for complete dissolution of PVP and Mg stearate. If any undissolved amounts persisted, the mixture was heated again for 30 seconds and stirred continuously in room temperature for another 10-15 minutes. After cooling, approximately 816 µL of 1.2255 M conc. N-acetylcysteine was added under constant stirring. Approximately 1.81 mg of chloroquine diphosphate salt was then added to the solution with constant stirring. The mixture was heated to approximately 90° C. with constant stirring for 10 minutes to ensure all products dissolved. After cooling to room temperature, the solution was transferred to conical tubes and place at 4° C. until use.

Tubes were carefully removed from their packages in a sterile hood and dipped into the N-acetylcysteine/chloroquine solution for 15 minutes. Coated tubes were dried at 37° C.+5% $CO_2$ for 15 minutes. Tubes were dipped and dried observing aseptic procedures 3 times and dried at 37° C.+5% $CO_2$ until use in the animal model.

The results provided in the Examples demonstrate that neutrophil activation was induced by mtDNA in vivo and subsequently elevated TLR-9 expression and the production of reactive oxygen species (ROS). Sterile injury was replicated in vitro as demonstrated with endotracheal tubes and catheters followed by reversal of the injury with the synergistic use of the pharmacological agents including NAC+ aminoquinolines and pharmacological agents including endonuclease+aminoquinolines. Neutrophil activation was controlled by mitigating TLR-9 expression and by decreasing reactive oxygen species (ROS) activity. Mitigating neutrophil activity to prevent further inflammation, tissue injury, and pain of the mucosal tissues due to sterile injury as a result of foreign body use was achieved.

What is claimed is:

1. A method for treating sterile injury selected from the group consisting of inflammation, necrosis, pain, sore throat and a combination thereof, in a subject in need thereof, the method comprising: administering to the subject, wherein the subject has the sterile injury in the absence of a microorganism, a composition comprising N-Acetylcysteine and an aminoquinoline, wherein the sterile injury results from the trauma due to the presence of a medical device in the subject in need thereof.

2. The method of claim 1, wherein the aminoquinoline is selected from the group consisting of 4-amino quinoline (quinolin-4-amine), chloroquine ((RS)—N'-(7-chloroquinolin-4-yl)-N,N-diethyl-pentane-1,4-diamine), amodiaquine (4-[(7-chloroquinolin-4-yl)amino]-2-[(diethylamino) methyl]phenol), and hydroxychloroquine ((RS)-2-[{4-[(7-chloroquinolin-4-yl)amino]pentyl}(ethyl)amino]ethanol).

3. The method of claim 1, wherein the administration is selected from the group consisting of oral, rectal, bronchial, nasal, topical, buccal, sub-lingual, transdermal, vaginal, parenteral, inhalation, insufflation, sustained release, and combinations thereof.

4. The method of claim 1, comprising coating the medical device with the composition prior implanting the medical device in the subject in need thereof.

5. The method of claim 1, wherein the medical device is selected from the group consisting of a catheter, a tube, a guidewire, a urinary implantable device, a suture, a stent, a continence sling, an electrosurgical cutting loop, a stone retrieval snare, a wound drain, an ablation device, a cardiopulmonary device, a cardiothoracic device, a coronary balloon, an embolic protection system, a heart valve, an endoscope, a mesh, a cranial fixation, and a shunt.

6. The method of claim 1 further comprising detecting mitochondrial DNA (mtDNA) level in at least one sample obtained from the subject prior to administration and detecting mitochondrial DNA (mtDNA) level in at least one sample obtained from the subject following administration.

7. The method of claim 6, wherein the sample is selected from the group consisting of tracheal lavage fluid, blood, urine, and combinations thereof.

8. The method of claim 1 further comprising detecting TLR-9 level, IL1β level, IL6 level, IL8, TNF-α level, IL10 level, and combinations thereof in at least one sample obtained from the subject prior to administration and detecting TLR-9 level, IL1β level, IL6 level, IL8, TNF-α level, IL10 level, and combinations thereof in at least one sample obtained from the subject following administration.

9. The method of claim 8, wherein the sample is selected from the group consisting of tracheal lavage fluid, blood, urine, and combinations thereof.

* * * * *